(12) United States Patent
Penning et al.

(10) Patent No.: US 8,546,368 B2
(45) Date of Patent: Oct. 1, 2013

(54) PYRAZOLOQUINOLONES ARE POTENT PARP INHIBITORS

(75) Inventors: Thomas D. Penning, Elmhurst, IL (US);
Gui-Dong Zhu, Gurnee, IL (US);
Virajkumar B. Gandhi, Gurnee, IL (US); Jianchun Gong, Deerfield, IL (US); Vincent L. Giranda, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 464 days.

(21) Appl. No.: 11/675,570

(22) Filed: Feb. 15, 2007

(65) Prior Publication Data
US 2007/0249597 A1 Oct. 25, 2007

Related U.S. Application Data

(60) Provisional application No. 60/773,513, filed on Feb. 15, 2006.

(51) Int. Cl.
*A01N 43/00* (2006.01)
*A61K 31/33* (2006.01)
*C07D 413/00* (2006.01)
*C07D 401/00* (2006.01)

(52) U.S. Cl.
USPC ............................ 514/183; 544/128; 544/363

(58) Field of Classification Search
USPC .................................. 514/183; 544/128, 363
See application file for complete search history.

(56) References Cited

U.S. PATENT DOCUMENTS

| | | | |
|---|---|---|---|
| 4,612,318 A * | 9/1986 | Winters | 514/293 |
| 5,212,310 A | 5/1993 | Albaugh et al. | |
| 5,677,309 A | 10/1997 | Chen et al. | |
| 6,589,947 B1 | 7/2003 | Chen et al. | |
| 6,949,648 B2 * | 9/2005 | Uchikawa et al. | 546/82 |
| 7,169,926 B1 | 1/2007 | Burgess et al. | |
| 2003/0004180 A1 | 1/2003 | Collins et al. | |
| 2003/0078277 A1 | 4/2003 | Hibi et al. | |
| 2003/0176698 A1 | 9/2003 | Kusaka et al. | |
| 2007/0207998 A1 | 9/2007 | Schrattenholz | |
| 2007/0265251 A1 | 11/2007 | Schrattenholz | |

FOREIGN PATENT DOCUMENTS

| | | |
|---|---|---|
| EP | 0104522 A2 | 4/1984 |
| EP | 0103422 B1 | 7/1987 |
| EP | 1566380 A1 | 8/2005 |
| JP | 2000319278 A | 11/2000 |
| WO | 0142247 A1 | 6/2001 |
| WO | 03063874 A1 | 8/2003 |
| WO | 2005087775 A1 | 9/2005 |
| WO | 2006107771 A2 | 10/2006 |
| WO | 2006112331 A1 | 10/2006 |
| WO | 2007032466 A1 | 3/2007 |

OTHER PUBLICATIONS

Burkhart, V., et al., "Mice lacking the poly(ADP-ribose) polymerase gene are resistant to pancreatic beta-cell destruction and diabetes development induced by streptozocin", Nature Medicine, pp. 5314-5319, 1999.
Chen, G., et al., "Potentiation of the antitumor activity of cisplatin in mice by 3-aminobenzamide and nicotinamide", Cancer Chemotherapy and Pharmacology, vol. 22, pp. 303-307, 1988.
Cuzzocrea, S., et al., "Protective effects of 3-aminobenzamide, an inhibitor of poly (ADP-ribose) synthase in a carrageenan-induced model of local inflammation", European Journal of Pharmacology, vol. 342, pp. 67-76, 1998.
Ehrlich, W., et al., "Inhibition of the induction of collagenase by interleukin-1β in cultured rabbit synovial fibroblasts after treatment with the poly(ADP-ribose)-polymerase inhibitor 3-aminobenzamide", Rheumatol Int, vol. 15, pp. 171-172, 1995.
IUPAC 1974 Recommendations for Section E, Fundamental Stereochemistry, Pure and Applied Chemistry, vol. 45, pp. 13-30, 1974.
Kröger, H., et al., "Synergistic effects of thalidomide and poly(ADP-ribose) polymerase inhibition on Type II of collagen-induced arthritis in mice", Inflammation, vol. 20, pp. 203-215, 1996.
Szabo, C., et al., "Protection against peroxynitrite-induced fibroblast injury and arthritis development by inhibition of poly(ADP-ribose) synthase", Proc Natl Acad Sci USA, vol. 95, pp. 3867-3872, Mar. 1998.
Thiemermann, C., et al., "Inhibition of the activity of poly(ADP ribose) synthetase reduces ischemia-reperfusion injury in the heart and skeletal muscle", Proc Natl Acad Sci USA, vol. 94, pp. 679-683, 1997.
Weltin, D. et al. "Immunosuppressive activities of 6(5H)-phenanthridinone, a new poly(ADP-Ribose)polymerase inhibitor", International Journal of Immunopharmacology, vol. 17, pp. 265-271, 1995.
Winters, G., et al., "Easy Synthesis of New Ring-Fused Pyridones from Heteroaromatic β-Vinylamines", Synthesis, pp. 1052-1054, 1984.
ISR for PCT/US2007/062260 dated Jul. 30, 2007.
IPRP for PCT/US2007/062260 dated Aug. 19, 2008.

* cited by examiner

Primary Examiner — Marcos Sznaidman
(74) Attorney, Agent, or Firm — Susan L. Steele

(57) ABSTRACT

Compounds of Formula (I)

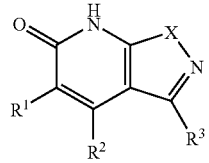

Formula (I)

inhibit the PARP enzyme and are useful for treating a disease or a disorder associated with PARP. Also disclosed are pharmaceutical compositions comprising compounds of Formula (I), methods of treatment comprising compounds of Formula (I), and methods of inhibiting the PARP enzyme comprising compounds of Formula (I).

1 Claim, No Drawings

PYRAZOLOQUINOLONES ARE POTENT PARP INHIBITORS

This application claims priority from U.S. Provisional Patent Application Ser. No. 60/773,513, filed Feb. 15, 2006, incorporated herein by reference.

TECHNICAL FIELD

The present invention relates to pyrazoloquinolones, their preparation, and their use as inhibitors of the enzyme poly (ADP-ribose)polymerase for the preparation of drugs.

BACKGROUND

Poly(ADP-ribose)polymerase (PARP) or poly(ADP-ribose)synthase (PARS) has an essential role in facilitating DNA repair, controlling RNA transcription, mediating cell death, and regulating immune response. These actions make PARP inhibitors targets for a broad spectrum of disorders. PARP inhibitors have demonstrated efficacy in numerous models of disease, particularly in models of ischemia reperfusion injury, inflammatory disease, degenerative diseases, protection from adverse effects of cytoxic compounds, and the potentiation of cytotoxic cancer therapy. PARP has also been indicated in retroviral infection and thus inhibitors may have use in antiretroviral therapy. PARP inhibitors have been efficacious in preventing ischemia reperfusion injury in models of myocardial infarction, stroke, other neural trauma, organ transplantation, as well as reperfusion of the eye, kidney, gut and skeletal muscle. Inhibitors have been efficacious in inflammatory diseases such as arthritis, gout, inflammatory bowel disease, CNS inflammation such as MS and allergic encephalitis, sepsis, septic shock, hemmorhagic shock, pulmonary fibrosis, and uveitis. PARP inhibitors have also shown benefit in several models of degenerative disease including diabetes (as well as complications) and Parkinsons disease. PARP inhibitors can ameliorate the liver toxicity following acetaminophen overdose, cardiac and kidney toxicities from doxorubicin and platinum based antineoplastic agents, as well as skin damage secondary to sulfur mustards. In various cancer models, PARP inhibitors have been shown to potentiate radiation and chemotherapy by increasing cell death of cancer cells, limiting tumor growth, decreasing metastasis, and prolonging the survival of tumor-bearing animals.

SUMMARY OF THE INVENTION

In one embodiment, the present invention provides compounds of Formula (I)

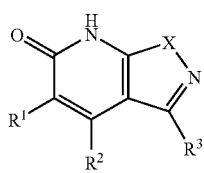

Formula (I)

and therapeutically acceptable salts, prodrugs and salts of prodrugs thereof, wherein $R^1$ and $R^2$ together with the atoms to which they are attached form a 5, 6, 7, or 8 membered cycloalkyl or heterocycle, the cycloalkyl or heterocycle may be unsubstituted or substituted with 1, 2, or 3 substituents independently selected from the group consisting of alkenyl, alkoxy, alkoxyalkyl, alkoxycarbonyl, alkoxycarbonylalkyl, C1-C6 alkyl, alkynyl, aryl, arylalkoxycarbonyl, arylalkyl, cycloalkyl, cycloalkylalkyl, cyano, haloalkoxy, haloalkyl, halogen, heterocycle, heterocyclealkyl, heterocyclecarbonyl, heterocyclecarbonylalkyl, heterocyclesulfonyl, heteroaryl, heteroarylalkyl, hydroxy, hydroxyalkyl, nitro, $NR^AR^B$, $(NR^AR^B)$alkyl, $(NR^AR^B)$carbonyl, $(NR^AR^B)$carbonylalkyl, and $(NR^AR^B)$sulfonyl;

$R^3$ is selected from the group consisting of alkenyl, alkoxy, alkoxyalkyl, alkoxycarbonyl, alkoxycarbonylalkyl, C1-C6 alkyl, alkynyl, aryl, arylalkyl, cycloalkyl, cycloalkylalkyl, cyano, haloalkoxy, haloalkyl, halogen, heterocycle, heterocyclealkyl, heterocyclecarbonyl, heterocyclecarbonylalkyl, heterocyclesulfonyl, heteroaryl, heteroarylalkyl, hydrogen, hydroxy, hydroxyalkyl, nitro, $NR^AR^B$, $(NR^AR^B)$alkyl, $(NR^AR^B)$carbonyl, $(NR^AR^B)$carbonylalkyl, and $(NR^AR^B)$sulfonyl;

X is $NR^4$;

$R^4$ is selected from the group consisting of C1-C6 alkyl, alkoxycarbonylalkyl, arylalkyl, carboxyalkyl, cyanoalkyl, cycloalkyl, cycloalkylalkyl, hydrogen, $(NR^AR^B)$alkyl, $(NR^AR^B)$carbonyl, $(NR^AR^B)$carbonylalkyl, -alkyl-O—C(O)—$(NR^AR^B)$, formylalkyl, heteroarylalkyl, heterocyclealkyl, hydroxyalkyl, alkoxyalkyl, and haloalkyl; and $R^A$ and $R^B$ are independently selected from the group consisting of hydrogen, alkyl, aryl, arylalkyl, arylalkylcarbonyl, arylalkoxy, arylalkoxycarbonyl, cycloalkyl, cycloalkylalkyl, and heterocycle;

if $R^3$ is C1-alkyl and $R^4$ is C1-alkyl and the ring formed by $R^1$ and $R^2$ is heterocycle then the heterocycle may not be substituted with methyl or methylcarbonyl;

and if $R^3$ is C1-alkyl and $R^4$ is C1-alkyl and the ring formed by $R^1$ and $R^2$ is a cycloalkyl then the cycloalkyl must be substituted; and wherein the aryl, cycloalkyl, heterocycle and heterocyclealkyl represented by $R^3$ and $R^4$ either themselves or as part of another moiety, are independently unsubstituted or substituted with 1, 2, or 3 substituents independently selected from the group consisting of alkenyl, alkoxy, alkoxyalkyl, alkoxycarbonyl, C1-C6-alkyl, alkylcarbonyl, alkylcarbonyloxy, alkylthio, alkylthioalkyl, alkynyl, aryl, arylalkyl, arylalkoxy, arylalkoxycarbonyl, carboxy, cyano, cycloalkyl, cycloalkylalkyl, formyl, haloalkoxy, haloalkyl, halogen, hydroxy, hydroxyalkyl, mercapto, nitro, oxo, —$NR^AR$, $(NR^AR^B)$alkyl, $(NR^AR^B)$carbonyl, $(NR^AR^B)$carbonylalkyl, $(NR^AR^B)$sulfonyl, alkylsulfonyl, heterocycle, heterocyclealkyl, heteroaryl, and heteroarylalkyl, wherein the substituent moieties are themselves further unsubstituted.

DETAILED DESCRIPTION OF THE INVENTION

In another embodiment, the present invention provides compounds of Formula (I)

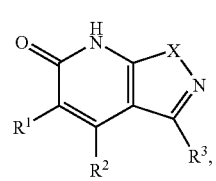

(I)

and therapeutically acceptable salts, prodrugs and salts of prodrugs thereof, wherein R¹ and R² together with the atoms to which they are attached form a 5, 6, or 7 membered cycloalkyl or heterocycle, the cycloalkyl or heterocycle may be unsubstituted or substituted with a substituent independently selected from the group consisting of heterocycle and $NR^AR^B$;

$R^3$ is selected from the group consisting of C1-C6 alkyl, aryl, cycloalkyl, heterocycle, heteroaryl, hydrogen, and $(NR^AR^B)$alkyl;

X is $NR^4$;

$R^4$ is selected from the group consisting of C1-C6 alkyl, -alkyl-O—C(O)—$(NR^AR^B)$, alkoxycarbonylalkyl, arylalkyl, carboxyalkyl, cyanoalkyl, hydrogen, haloalkyl, heteroarylalkyl, heterocyclealkyl, hydroxyalkyl, formylalkyl, and $(NR^AR^B)$alkyl;

$R^A$ and $R^B$ are independently selected from the group consisting of hydrogen, C1-C6 alkyl, arylalkoxycarbonyl, cycloalkyl, cycloalkylalkyl, and heterocycle;

if $R^3$ is C1-alkyl and $R^4$ is C1-alkyl and the ring formed by $R^1$ and $R^2$ is heterocycle then the heterocycle may not be substituted with methyl or methylcarbonyl;

and if $R^3$ is C1-alkyl and $R^4$ is C1-alkyl and the ring formed by $R^1$ and $R^2$ is a cycloalkyl then the cycloalkyl must be substituted; and wherein the aryl, cycloalkyl, heterocycle and heterocyclealkyl represented by $R^3$ and $R^4$ either themselves or as part of another moiety, are independently unsubstituted or substituted with 1, 2, or 3 substituents independently selected from the group consisting of alkenyl, alkoxy, alkoxyalkyl, alkoxycarbonyl, C1-C6-alkyl, alkylcarbonyl, alkylcarbonyloxy, alkylthio, alkylthioalkyl, alkynyl, aryl, arylalkyl, arylalkoxy, arylalkoxycarbonyl, carboxy, cyano, cycloalkyl, cycloalkylalkyl, formyl, haloalkoxy, haloalkyl, halogen, hydroxy, hydroxyalkyl, mercapto, nitro, oxo, —$NR^AR^B$, $(NR^AR^B)$alkyl, $(NR^AR^B)$carbonyl, $(NR^AR^B)$carbonylalkyl, $(NR^AR^B)$sulfonyl, alkylsulfonyl, heterocycle, heterocyclealkyl, heteroaryl, and heteroarylalkyl, wherein the substituent moieties are themselves further unsubstituted.

In another embodiment, the present invention provides compounds of Formula (I)

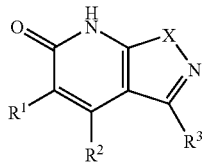

Formula (I)

and therapeutically acceptable salts, prodrugs and salts of prodrugs thereof, wherein R¹ and R² together with the atoms to which they are attached form a 5, 6, 7, or 8 membered cycloalkyl or heterocycle, the cycloalkyl or heterocycle may be unsubstituted or substituted with 1, 2, or 3 substituents independently selected from the group consisting of alkenyl, alkoxy, alkoxyalkyl, alkoxycarbonyl, alkoxycarbonylalkyl, C1-C6 alkyl, alkynyl, aryl, arylalkoxycarbonyl, arylalkyl, cycloalkyl, cycloalkylalkyl, cyano, haloalkoxy, haloalkyl, halogen, heterocycle, heterocyclealkyl, heterocyclecarbonyl, heterocyclecarbonylalkyl, heterocyclesulfonyl, heteroaryl, heteroarylalkyl, hydroxy, hydroxyalkyl, nitro, $NR^AR^B$, $(NR^AR^B)$alkyl, $(NR^AR^B)$carbonyl, $(NR^AR^B)$carbonylalkyl, and $(NR^AR^B)$sulfonyl;

$R^3$ is selected from the group consisting of alkenyl, alkoxy, alkoxyalkyl, alkoxycarbonyl, alkoxycarbonylalkyl, C2-C6 alkyl, alkynyl, aryl, arylalkyl, cycloalkyl, cycloalkylalkyl, cyano, haloalkoxy, haloalkyl, halogen, heterocycle, heterocyclealkyl, heterocyclecarbonyl, heterocyclecarbonylalkyl, heterocyclesulfonyl, heteroaryl, heteroarylalkyl, hydrogen, hydroxy, hydroxyalkyl, nitro, $NR^AR^B$, $(NR^AR^B)$alkyl, $(NR^AR^B)$carbonyl, $(NR^AR^B)$carbonylalkyl, and $(NR^AR^B)$sulfonyl;

X is $NR^4$;

$R^4$ is selected from the group consisting of C2-C6 alkyl, arylalkyl, cycloalkyl, cycloalkylalkyl, hydrogen, $(NR^AR^B)$alkyl, hydroxyalkyl, alkoxyalkyl, and haloalkyl; and $R^A$ and $R^B$ are independently selected from the group consisting of hydrogen, alkyl, aryl, arylalkyl, arylalkylcarbonyl, arylalkoxy, arylalkoxycarbonyl, cycloalkyl, cycloalkylalkyl, and heterocycle; and wherein the aryl, cycloalkyl, heterocycle and heterocyclealkyl represented by $R^3$ and $R^4$ either themselves or as part of another moiety, are independently unsubstituted or substituted with 1, 2, or 3 substituents independently selected from the group consisting of alkenyl, alkoxy, alkoxyalkyl, alkoxycarbonyl, C1-C6-alkyl, alkylcarbonyl, alkylcarbonyloxy, alkylthio, alkylthioalkyl, alkynyl, aryl, arylalkyl, arylalkoxy, arylalkoxycarbonyl, carboxy, cyano, cycloalkyl, cycloalkylalkyl, formyl, haloalkoxy, haloalkyl, halogen, hydroxy, hydroxyalkyl, mercapto, nitro, oxo, —$NR^AR^B$, $(NR^AR^B)$alkyl, $(NR^AR^B)$carbonyl, $(NR^AR^B)$carbonylalkyl, $(NR^AR^B)$sulfonyl, alkylsulfonyl, heterocycle, heterocyclealkyl, heteroaryl, and heteroarylalkyl, wherein the substituent moieties are themselves further unsubstituted.

In another embodiment, the present invention provides compounds of Formula (I) or a therapeutically acceptable salt thereof wherein R¹ and R² together with the atoms to which they are attached form a 5, 6, 7, or 8 membered cycloalkyl.

In another embodiment, the present invention provides compounds of Formula (I) or a therapeutically acceptable salt thereof wherein R¹ and R² together with the atoms to which they are attached form a 5, 6, 7, or 8 membered heterocycle.

In another embodiment, the present invention provides compounds of Formula (I) or a therapeutically acceptable salt thereof wherein X is $NR^4$.

In another embodiment, the present invention provides compounds of Formula (I) or a therapeutically acceptable salt thereof wherein R¹ and R² together with the atoms to which they are attached form a 5, 6, 7, or 8 membered cycloalkyl.

In another embodiment, the present invention provides compounds of Formula (I) or a therapeutically acceptable salt thereof wherein R¹ and R² together with the atoms to which they are attached form a 5, 6, 7, or 8 membered heterocycle.

In another embodiment, the present invention provides compounds of Formula (I) or a therapeutically acceptable salt thereof wherein R¹ and R² together with the atoms to which they are attached form a 5, 6, 7, or 8 membered cycloalkyl; and $R^3$ is selected from the group consisting of C1-C6 alkyl, aryl, cycloalkyl, heterocycle, heteroaryl, hydrogen, and $(NR^AR^B)$alkyl.

In another embodiment, the present invention provides compounds of Formula (I) or a therapeutically acceptable salt thereof wherein R¹ and R² together with the atoms to which they are attached form a 5, 6, 7, or 8 membered cycloalkyl; and $R^3$ is selected from the group consisting of aryl, cycloalkyl, heterocycle, and heteroaryl.

In another embodiment, the present invention provides compounds of Formula (I) or a therapeutically acceptable salt thereof wherein R¹ and R² together with the atoms to which they are attached form a 5, 6, 7, or 8 membered cycloalkyl; X is $NR^4$; $R^4$ is C1-C6 alkyl; and $R^3$ is selected from the group consisting of aryl, cycloalkyl, heterocycle, and heteroaryl.

In another embodiment, the present invention provides compounds of Formula (I) or a therapeutically acceptable salt thereof wherein $R^3$ is selected from the group consisting of aryl, cycloalkyl, heterocycle, and heteroaryl.

In another embodiment, the present invention provides compounds of Formula (I) or a therapeutically acceptable salt thereof wherein $R^4$ is selected from the group consisting of C1-C6 alkyl, -alkyl-O—C(O)—(NR$^A$R$^B$), alkoxycarbonylalkyl, arylalkyl, carboxyalkyl, cyanoalkyl, hydrogen, haloalkyl, heteroarylalkyl, heterocyclealkyl, hydroxyalkyl, formylalkyl, and (NR$^A$R$^B$)alkyl.

In another embodiment, the present invention provides compounds of Formula (I) or a therapeutically acceptable salt thereof wherein $R^1$ and $R^2$ together with the atoms to which they are attached form a 6 membered cycloalkyl.

In another embodiment, the present invention provides compounds of Formula (I) or a therapeutically acceptable salt thereof wherein $R^3$ is a heterocycle.

In another embodiment, the present invention provides compounds of Formula (I) or a therapeutically acceptable salt thereof wherein $R^3$ is pyrrolidinyl.

In another embodiment, the present invention provides compounds of Formula (I) or a therapeutically acceptable salt thereof wherein $R^1$ and $R^2$ together with the atoms to which they are attached form a 6 membered cycloalkyl; and $R^3$ is pyrrolidinyl.

In another embodiment, the present invention provides a pharmaceutical composition comprising a compound of Formula (I), or a therapeutically acceptable salt thereof, in combination with a therapeutically acceptable carrier.

In another embodiment, the present invention provides a method of inhibiting PARP in a mammal in recognized need of such treatment comprising administering to the mammal a therapeutically acceptable amount of a compound of Formula (I) or a therapeutically acceptable salt thereof.

In another embodiment, the present invention provides a method of treating cancer in a mammal in recognized need of such treatment comprising administering to the mammal a therapeutically acceptable amount of a compound of Formula (I) or a therapeutically acceptable salt thereof.

In another embodiment, the present invention provides a method for decreasing tumor volume in a mammal in recognized need of such treatment comprising administering to the mammal a therapeutically acceptable amount of a compound of Formula (I) or a therapeutically acceptable salt thereof.

In another embodiment, the present invention provides a method of treating leukemia, colon cancer, glioblastomas, lymphomas, melanomas, carcinomas of the breast, or cervical carcinomas in a mammal in recognized need of such treatment comprising administering to the mammal a therapeutically acceptable amount of a compound of Formula (I) or a therapeutically acceptable salt thereof.

In another embodiment, the present invention provides a method of potentiation of cytotoxic cancer therapy in a mammal in recognized need of such treatment comprising administering to the mammal a therapeutically acceptable amount of a compound of Formula (I) or a therapeutically acceptable salt thereof.

In another embodiment, the present invention provides a method of potentiation of radiation therapy in a mammal in recognized need of such treatment comprising administering to the mammal a therapeutically acceptable amount of a compound of Formula (I) or a therapeutically acceptable salt thereof.

In another embodiment, the present invention provides a method of treating ischemia reperfusion injury associated with, but not limited to, myocardial infarction, stroke, other neural trauma, and organ transplantation, in a mammal in recognized need of such treatment comprising administering to the mammal a therapeutically acceptable amount of a compound of Formula (I) or a therapeutically acceptable salt thereof.

In another embodiment, the present invention provides a method of reperfusion including, but not limited to, reperfusion of the eye, kidney, gut and skeletal muscle, in a mammal in recognized need of such treatment comprising administering to the mammal a therapeutically acceptable amount of a compound of Formula (I) or a therapeutically acceptable salt thereof.

In another embodiment, the present invention provides a method of treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a therapeutically acceptable salt thereof.

In another embodiment, the present invention provides a method of treating immunological diseases or disorders such as rheumatoid arthritis and septic shock in a mammal in recognized need of such treatment comprising administering to the mammal a therapeutically acceptable amount of a compound of Formula (I) or a therapeutically acceptable salt thereof.

In another embodiment, the present invention provides a method of treating degenerative disease including, but not limited to, diabetes and Parkinsons disease, in a mammal in recognized need of such treatment comprising administering to the mammal a therapeutically acceptable amount of a compound of Formula (I) or a therapeutically acceptable salt thereof.

In another embodiment, the present invention provides a method of treating hypoglycemia in a mammal in recognized need of such treatment comprising administering to the mammal a therapeutically acceptable amount of a compound of Formula (I) or a therapeutically acceptable salt thereof.

In another embodiment, the present invention provides a method of treating retroviral infection in a mammal in recognized need of such treatment comprising administering to the mammal a therapeutically acceptable amount of a compound of Formula (I) or a therapeutically acceptable salt thereof.

In another embodiment, the present invention provides a method of treating liver toxicity following acetominophen overdose in a mammal in recognized need of such treatment comprising administering to the mammal a therapeutically acceptable amount of a compound of Formula (I) or a therapeutically acceptable salt thereof.

In another embodiment, the present invention provides a method of treating cardiac and kidney toxicities from doxorubicin and platinum based antineoplastic agents in a mammal in recognized need of such treatment comprising administering to the mammal a therapeutically acceptable amount of a compound of Formula (I) or a therapeutically acceptable salt thereof.

In another embodiment, the present invention provides a method of treating skin damage secondary to sulfur mustards in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for inhibiting the PARP enzyme in a mammal in recognized need of such treatment.

In another embodiment, the present invention provides a use of a compound of Formula (I), or a therapeutically acceptable salt thereof, to prepare a medicament for inhibiting tumor growth in a mammal in recognized need of such treatment.

In another embodiment, the present invention provides a use of a compound of Formula (I), or a therapeutically acceptable salt thereof, to prepare a medicament for treating cancer in a mammal in recognized need of such treatment.

In another embodiment, the present invention provides a use of a compound of Formula (I), or a therapeutically acceptable salt thereof, to prepare a medicament for treating leukemia, colon cancer, glioblastomas, lymphomas, melanomas, carcinomas of the breast, or cervical carcinomas in a mammal in a mammal in recognized need of such treatment.

In another embodiment, the present invention provides a use of a compound of Formula (I), or a therapeutically acceptable salt thereof, to prepare a medicament for potentiation of cytotoxic cancer therapy in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for potentiation of radiation in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating ischemia reperfusion injury associated with, but not limited to, myocardial infarction, stroke, other neural trauma, and organ transplantation, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating reperfusion including, but not limited to, reperfusion of the eye, kidney, gut and skeletal muscle, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating immunological diseases or disorders such as rheumatoid arthritis and septic shock in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating degenerative disease including, but not limited to, diabetes and Parkinsons disease, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating hypoglycemia in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating retroviral infection in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating liver toxicity following acetaminophen overdose in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating cardiac and kidney toxicities from doxorubicin and platinum based antineoplastic agents in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating skin damage secondary to sulfur mustards in a mammal in recognized need of such treatment comprising administering to the mammal a therapeutically acceptable amount of a compound of Formula (I) or a therapeutically acceptable salt thereof.

DEFINITIONS

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means at least one alkoxy group, as defined herein, appended to the parent molecular moiety through an alkyl group, as defined herein.

Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "C1-C6 alkyl" as used herein, means a straight or branched chain hydrocarbon containing from 1 to 6 carbon atoms.

The term "$C_1$-alkyl" means methyl.

The term "$C_2$-alkyl" means ethyl.

The term "$C_3$-alkyl" means prop-1-yl and prop-2-yl (isopropyl).

The term "$C_4$-alkyl" means but-1-yl, but-2-yl, 2-methylprop-1-yl, and 2-methylprop-2-yl (tert-butyl).

The term "$C_5$-alkyl" means 2,2-dimethylprop-1-yl (neopentyl), 2-methylbut-1-yl, 2-methylbut-2-yl, 3-methylbut-1-yl, 3-methylbut-2-yl, pent-1-yl, pent-2-yl, and pent-3-yl.

The term "$C_6$-alkyl" means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl, and 4-methylpent-2-yl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "-alkyl-O—C(O)—(NR$^A$R$^B$)" as used herein, means a (NR$^A$R$^B$)carbonyloxy group, as defined herein, appended to the parent molecule through an alkyl group.

The term "alkylsulfonyl" as used herein, means an alkyl group appended to the parent molecular moiety through a sulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl group or a naphthyl group.

The aryl groups are unsubstituted or substituted with one, two, three, four, or five substituents independently selected from the group consisting of alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —NR$^A$R$^B$, (NR$^A$R$^B$)alkyl, (NR$^A$R$^B$)carbonyl, and tetrazolyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, 1-methyl-3-phenylpropyl, and 2-naphth-2-ylethyl.

The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethoxycarbonyl.

The term "carbonyl" as used herein, means a —C(O)— group.

The term "carboxy" as used herein, means a —CO$_2$H group.

The term "carboxyalkyl" as used herein, means a carboxy group, as defined herein, attached to the parent molecular moiety through an alkyl group.

The term "cyano" as used herein, means a —CN group.

The term "cyanoalkyl" as used herein, means a cyano group appended to the parent molecular moiety through an alkyl group.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The cycloalkyl groups are unsubstituted or substituted with 1, 2, 3, or 4 substituents selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, oxo, —NR$^A$R$^B$, and (NR$^A$R$^B$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "formyl" as used herein, means a —C(O)H group.

The term "formylalkyl" as used herein, means a formyl group, as defined herein, attached to the parent molecular moiety through an alkyl group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of halo alkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoro ethyl, and 2-chloro-3-fluoropentyl.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a phenyl group or the 5 or 6 membered heteroaryl ring is fused to another 5 or 6 membered heteroaryl ring. Nitrogen heteroatoms contained within the heteroaryl may be optionally oxidized to the N-oxide. The heteroaryl is connected to the parent molecular moiety through any carbon atom contained within the heteroaryl while maintaining proper valence. Representative examples of heteroaryl include, but are not limited to, benzothienyl, benzoxadiazolyl, cinnolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, tetrazolyl, thiadiazolyl, thiazolyl, thienopyridinyl, thienyl, triazolyl, and triazinyl.

The heteroaryl groups are unsubstituted or substituted with 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —NR$^A$R$^B$, and (NR$^A$R$^B$)carbonyl.

The term "heteroarylalkyl" as used herein, means a heteroaryl, as defined herein, appended to the parent molecular moiety through an alkyl group, as defined herein. Representative examples of heteroarylalkyl include, but are not limited to, pyridinymethyl.

The term "heterocycle" or "heterocyclic" as used herein, means a monocyclic or bicyclic heterocyclic ring. The monocyclic heterocyclic ring consists of a 3, 4, 5, 6, 7, or 8 membered ring containing at least one heteroatom independently selected from O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocyclic ring consists of a monocyclic heterocyclic ring fused to a cycloalkyl group or the monocyclic heterocyclic ring fused to a phenyl group or the monocyclic heterocyclic ring fused to another monocyclic heterocyclic ring. The heterocycle is connected to the parent molecular moiety through any carbon or nitrogen atom contained within the heterocycle while maintaining proper valence. Representative examples of heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The heterocycles are unsubstituted or substituted with 1, 2, or 3 substituents independently selected from alkenyl, alkoxy, alkoxyalkyl, alkoxycarbonyl, alkyl, alkylcarbonyl, alkylcarbonyloxy, alkylthio, alkylthioalkyl, alkynyl, aryl, arylalkyl, arylalkoxy, arylalkoxycarbonyl, carboxy, cyano, cycloalkyl, cycloalkylalkyl, formyl, haloalkoxy, haloalkyl, halogen, hydroxy, hydroxyalkyl, mercapto, nitro, —NR$^A$R$^B$, (NR$^A$R$^B$)alkyl, (NR$^A$R$^B$)carbonyl, sulfonyl, alkylsulfonyl, tetrahydropyranyl, and heteroarylalkyl wherein the heteroaryl is pyridinyl.

The term "heterocyclealkyl" as used herein, means a heterocycle, as defined herein, appended to the parent molecular moiety through an alkyl group, as defined herein.

The term "heterocyclecarbonyl" as used herein, means a heterocycle group, as defined herein, appended to the parent molecular moiety through a carbonyl group, as defined herein. Representative examples of heterocyclecarbonyl include, but are not limited to, 1,3-benzodioxol-4-ylcarbonyl, pyridin-3-ylcarbonyl, pyrimidin-2-ylcarbonyl, tetrahydrofuran-2-ylcarbonyl, tetrahydrofuran-3-ylcarbonyl, tetrahydro-2H-pyran-2-ylcarbonyl, tetrahydro-2H-pyran-4-ylcarbonyl, tetrahydrothien-2-ylcarbonyl and tetrahydrothien-3-ylcarbonyl.

The term "heterocyclecarbonylalkyl" as used herein, means a heterocyclecarbonyl group, as defined herein, appended to the parent molecular moiety through an alkyl group, as defined herein.

The term "heterocyclesulfonyl" as used herein, means a heterocycle group, as defined herein, appended to the parent molecular moiety through a sulfonyl group, as defined herein.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "nonaromatic" as used herein, means that a 4 membered nonaromatic ring contains zero double bonds, a 5 membered nonaromatic ring contains zero or one double bond, a 6, 7, or 8 membered nonaromatic ring contains zero, one, or two double bonds.

The term "NR$^A$R$^B$" as used herein, means two groups, R$^A$ and R$^B$, which are appended to the parent molecular moiety through a nitrogen atom. R$^A$ and R$^B$ are each independently hydrogen, alkyl, and alkylcarbonyl. Representative examples of NR$^A$R$^B$ include, but are not limited to, amino, methylamino, acetylamino, and acetylmethylamino.

The term "(NR$^A$R$^B$)carbonyl" as used herein, means a NR$^A$R$^B$ group, as defined herein, appended to the parent molecular moiety through a carbonyl group, as defined herein. Representative examples of (NR$^A$R$^B$)carbonyl include, but are not limited to, aminocarbonyl, (methylamino)carbonyl, (dimethylamino)carbonyl, and (ethylmethylamino)carbonyl.

The term "($NR^AR^B$)carbonyloxy" as used herein, means a ($NR^AR^B$)carbonyl group as defined herein appended to the parent molecular moiety through an oxygen.

The term "$NR_CR_D$" as used herein, means two groups, $R_C$ and $R_D$, which are appended to the parent molecular moiety through a nitrogen atom. $R_C$ and $R_D$ are each independently hydrogen, alkyl, and alkylcarbonyl. Representative examples of $NR_CR_D$ include, but are not limited to, amino, methylamino, acetylamino, and acetylmethylamino.

The term "($NR_CR_D$)carbonyl" as used herein, means a $NR_CR_D$ group, as defined herein, appended to the parent molecular moiety through a carbonyl group, as defined herein. Representative examples of ($NR_CR_D$)carbonyl include, but are not limited to, aminocarbonyl, (methylamino)carbonyl, (dimethylamino)carbonyl, and (ethylmethylamino)carbonyl.

The term "($NR_CR_D$)carbonylalkyl" as used herein, means a ($NR_CR_D$)carbonyl group, as defined herein, appended to the parent molecular moiety through an alkyl group, as defined herein.

The term "($NR_CR_D$)sulfonyl" as used herein, means a $NR_CR_D$ group, as defined herein, appended to the parent molecular moiety through a sulfonyl group, as defined herein. Representative examples of ($NR_CR_D$)sulfonyl include, but are not limited to, aminosulfonyl, (methylamino)sulfonyl, (dimethylamino)sulfonyl, and (ethylmethylamino)sulfonyl.

The term "$NR^AR^B$" as used herein, means two groups, $R^A$ and $R^B$, which are appended to the parent molecular moiety through a nitrogen atom. $R^A$ and $R^B$ are each independently hydrogen, alkyl, cycloalkyl, and alkylcarbonyl. Representative examples of $NR^AR^B$ include, but are not limited to, amino, methylamino, acetylamino, and acetylmethylamino.

The term "($NR^AR^B$)carbonyl" as used herein, means a $NR^AR^B$ group, as defined herein, appended to the parent molecular moiety through a carbonyl group, as defined herein. Representative examples of ($NR^AR^B$)carbonyl include, but are not limited to, aminocarbonyl, (methylamino)carbonyl, (dimethylamino)carbonyl, and (ethylmethylamino)carbonyl.

The term "oxo" as used herein, means a =O moiety.

The term "sulfinyl" as used herein, means a —SO— group.

The term "sulfonyl" as used herein, means a —$SO_2$— group.

Compounds of the present invention can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Compounds of the present invention were named by ACD/ChemSketch version 5.06 (developed by Advanced Chemistry Development, Inc., Toronto, ON, Canada) or were given names which appeared to be consistent with ACD nomenclature.

Determination of Biological Activity

Inhibition of PARP

Nicotinamide[2,5',8-3H]adenine dinucleotide and strepavidin SPA beads were purchased from Amersham Biosciences (UK) Recombinant Human Poly(ADP-Ribose) Polymerase (PARP) purified from *E. coli* and 6-Biotin-17-$NAD^+$, were purchase from Trevigen, Gaithersburg, Md. $NAD^+$, Histone, aminobenzamide, 3-amino benzamide and Calf Thymus DNA (dcDNA) were purchased from Sigma, St. Louis, Mo. Stem loop oligonucleotide containing MCAT sequence was obtained from Qiagen. The oligos were dissolved to 1 mM in annealing buffer containing 10 mM Tris HCl pH 7.5, 1 mM EDTA, and 50 mM NaCl, incubated for 5 min at 95° C., and followed by annealing at 45° C. for 45 minutes. Histone H1 (95% electrophoretically pure) was purchased from Roche, Indianapolis, Ind. Biotinylated histone H1 was prepared by treating the protein with Sulfo-NHS-LC-Biotin from Pierce Rockford, Ill. The biotinylation reaction was conducted by slowly and intermittently adding 3 equivalents of 10 mM Sulfo-NHS-LC-Biotin to 100 μM Histone H1 in phosphate-buffered saline, pH 7.5, at 4° C. with gentle vortexing over 1 min followed by subsequent 4° C. incubation for 1 hr. Streptavidin coated (FlashPlate Plus) microplates were purchased from Perkin Elmer, Boston, Mass.

PARP1 assay was conducted in PARP assay buffer containing 50 mM Tris pH 8.0, 1 mM DTT, 4 mM $MgCl_2$. PARP reactions contained 1.5 μM [$^3$H]-$NAD^+$ (1.6 uCi/mmol), 200 nM biotinylated histone H1, 200 nM s1DNA, and 1 nM PARP enzyme. Auto reactions utilizing SPA bead-based detection were carried out in 100 μl volumes in white 96 well plates. Reactions were initiated by adding 50 μl of 2×$NAD^+$ substrate mixture to 50 μl of 2× enzyme mixture containing PARP and DNA. These reactions were terminated by the addition of 150 μl of 1.5 mM benzamide (~1000-fold over its IC50). 170 μl of the stopped reaction mixtures were transferred to streptavidin Flash Plates, incubated for 1 hr, and counted using a TopCount microplate scintillation counter. The $K_i$ data was determined from inhibition curves at various substrate concentrations and are shown in Table 1 for compounds of the present invention

TABLE 1

| PARP ($K_i$, nM) | | | | | | | | | |
|---|---|---|---|---|---|---|---|---|---|
| 46 | 14.2 | 7.1 | 158 | 4.5 | 21.5 | 6.3 | 13 | 450 | 81 |
| 11 | 62 | 59 | 19.6 | 1.6 | 11.6 | 22.5 | 43 | 29 | 1.7 |
| 9 | 29 | 16.8 | 64 | 3.5 | 3.1 | 5.7 | 13.3 | 800 | 180 |
| 52 | 10 | 34 | 55 | 2.6 | 472 | 4.1 | 6.3 | 3 | 10 |
| 11 | 2.8 | 1.2 | 69 | 3.3 | 20.7 | 2.4 | 15.3 | >8300 | 3.6 |
| 24.9 | 6 | 91 | 3.1 | 4.6 | 47 | 6.5 | 15.7 | 16.2 | 4.5 |

TABLE 1-continued

PARP ($K_i$, nM)

| | | | | | | | | | |
|---|---|---|---|---|---|---|---|---|---|
| 6.1 | 1.1 | 1.6 | 2.9 | 3.6 | 6.1 | 23 | 3.7 | 18.6 | 5 |
| 3.5 | 116 | 4.3 | 8.2 | 4.9 | 5.5 | 5.5 | .7 | 56 | 395 |
| 2.7 | 800 | 9.6 | 16.4 | 5.3 | 9.5 | 8.5 | 31 | 226 | 20.2 |
| 10.3 | 866 | 5.8 | 11.4 | 3.5 | 4.5 | 17 | 45 | 35 | 12.2 |
| 5.3 | 2.4 | 5.4 | 3700 | 3.2 | 5.6 | 13 | 44 | 11.9 | 2.8 |
| 9.8 | 11.3 | 2.1 | 6.5 | 4.6 | 34 | 33 | 52 | 1.1 | 2.0 |
| 70 | 4.3 | 3.4 | 18 | 6.5 | 17 | 211 | 4 | 20 | 5.6 |
| 231 | 2.9 | 57 | 37 | 20 | 19 | 256 | 6 | 10 | 2 |
| 109 | 1.8 | 35 | 2 | 32 | 26 | 315 | 7 | 23 | 2.5 |
| 456 | 4 | 52 | 4 | 42 | 242 | 24 | 6 | 37 | 3.7 |
| 590 | 2.7 | 90 | 4 | 5 | 14 | 15 | 8 | 31 | 3 |
| 640 | 2 | 135 | 5 | 122 | 14 | 2.3 | 5 | 41 | 7.2 |
| 2.7 | 4.7 | 129 | 10 | 65 | 18 | 2.9 | 6 | 27 | 16 |
| 8 | 54 | 131 | 251 | 1 | 53 | 134 | 86 | 69 | 167 |
| 20 | 49 | 228 | 233 | 23 | 135 | 65 | 181 | 25 | 183 |
| 18 | 59 | 3 | 12 | 30 | 27 | 217 | 26 | 65 | 239 |
| 5 | 49 | .4 | 3 | 5 | 40 | 245 | 17 | 88 | 9 |
| 3 | 39 | 14 | 25 | 12 | 60 | 72 | 61 | 27 | 155 |
| 307 | 163 | | | | | | | | |

Cellular PARP Assay:

C41 cells were treated with a compound of the present invention for 30 minutes in 96 well plate. PARP was then activated by damaging DNA with 1 mM $H_2O_2$ for 10 minutes. The cells were then washed with ice-cold PBS once and fixed with pre-chilled methanol:acetone (7:3) at −20° C. for 10 minutes. After air-drying, the plates were rehydrated with PBS and blocked 5% non-fat dry milk in PBS-tween (0.05%) (blocking solution) for 30 minutes at room temperature. The cells were incubated with anti-PAR antibody 10H (1:50) in Blocking solution at 37° C. for 60 minutes followed by washing with PBS-Tween20 5 times, and incubation with goat anti-mouse fluorescein 5(6)-isothiocyanate-coupled antibody (1:50) and 1 μg/ml 4',6-diamidino-2-phenylindole (DAPI) in blocking solution at 37° C. for 60 minutes. After washing with PBS-Tween20 5 times, the analysis was performed using an fmax Fluorescence Microplate Reader (Molecular Devices, Sunnyvale, Calif.), set at the excitation wavelength of 490 nm and emission wavelength of 528 nm fluorescein 5(6)-isothiocyanate (FITC) or the excitation wavelength of 355 nm and emission wavelength of 460 nm (DAPI). The PARP activity (FITC signal) was normalized with cell numbers (DAPI).

The cellular assay measures the formation of poly ADP-ribose by PARP within cells and demonstrates that compounds of the present invention penetrate cell membranes and inhibit PARP in intact cells. The $EC_{50s}$ for representative compounds of the present invention are provided in Table 2.

As PARP inhibitors, the compounds of the present invention have numerous therapeutic applications related to, ischemia reperfusion injury, inflammatory diseases, degenerative diseases, protection from adverse effects of cytotoxic compounds, and potentiation of cytotoxic cancer therapy. In particular, compounds of the present invention potentiate radiation and chemotherapy by increasing cell death of cancer cells, limiting tumor growth, decreasing metastasis, and prolonging the survival of tumor-bearing mammals. Compounds of Formula (I) can treat leukemia, colon cancer, glioblastomas, lymphomas, melanomas, carcinomas of the breast, and cervical carcinomas.

Other therapeutic applications include, but are not limited to, retroviral infection, arthritis, gout, inflammatory bowel disease, CNS inflammation, multiple sclerosis, allergic encephalitis, sepsis, septic shock, hemmorhagic shock, pulmonary fibrosis, uveitis, diabetes, Parkinsons disease, myocardial infarction, stroke, other neural trauma, organ transplantation, reperfusion of the eye, reperfusion of the kidney, reperfusion of the gut, reperfusion of skeletal muscle, liver toxicity following acetominophen overdose, cardiac and kidney toxicities from doxorubicin and platinum based antineoplastic agents, and skin damage secondary to sulfur mustards. (G. Chen et al. Cancer Chemo. Pharmacol. 22 (1988), 303; C. Thiemermann et al., Proc. Natl. Acad. Sci. USA 94 (1997), 679-683 D. Weltin et al. Int. J. Immunopharmacol. 17 (1995), 265-271; H. Kröger et al. Inflammation 20 (1996), 203-215; W. Ehrlich et al. Rheumatol. Int. 15 (1995), 171-

TABLE 2

Cellular Activity $EC_{50}$ (nM)

| | | | | | | | | | |
|---|---|---|---|---|---|---|---|---|---|
| 2.3 | 1.5 | 45 | 1 | 18 | 2.6 | 7 | 0.3 | 11.9 | 35 |
| 0.9 | 46 | 1 | 14 | 115 | <0.3 | >1000 | 0.5 | 12.1 | 4.8 |
| 11 | >1000 | 1.3 | 1.2 | 0.6 | 17.5 | 463 | 0.2 | 3.7 | 4.5 |
| 0.3 | 1.2 | .6 | 2.3 | 7 | .5 | 1.9 | .6 | 1.2 | .5 |
| 1.4 | .8 | .6 | 1 | 1.7 | .3 | .9 | .5 | 1.6 | .4 |
| .3 | .3 | .7 | 17 | 2.1 | .7 | 2.7 | .5 | 1.9 | >300 |
| .7 | 1.8 | 3.2 | .4 | 2.3 | .5 | 3.6 | .5 | 5.7 | 7.6 |
| .5 | .8 | 3.2 | .7 | 40 | 1.1 | 1.5 | .6 | 1 | .5 |
| .5 | .3 | 5.6 | .3 | 4.1 | 3.4 | 1.8 | .5 | 4 | .5 |
| .6 | .6 | 2.4 | .7 | 3.5 | 1.7 | .9 | .6 | 3.3 | 1.5 |
| >300 | >300 | .7 | 6.2 | >300 | 10.6 | 8.7 | >300 | 1.5 | 3.1 |
| .5 | 2.4 | 1.8 | 14 | >300 | >1000 | 14 | >300 | 63 | 7.9 |
| .8 | 5.6 | 4.5 | 15 | 16 | 259 | 112 | 52 | 8.2 | 8.9 |
| >300 | 57 | >300 | >300 | 191 | >300 | 61 | | | |

172; C. Szabo et al., Proc. Natl. Acad. Sci. USA 95 (1998), 3867-3872; S. Cuzzocrea et al. Eur. J. Pharmacol. 342 (1998), 67-76; V. Burkhart et al., Nature Medicine (1999), 5314-19).

When used in the above or other treatments, a therapeutically effective amount of one of the compounds of the present invention can be employed as a zwitterion or as a pharmaceutically acceptable salt. By a "therapeutically effective amount" of the compound of the invention is meant a sufficient amount of the compound to treat or prevent a disease or disorder ameliorated by a PARP inhibitor at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved.

By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. The salts can be prepared in situ during the final isolation and purification of the compounds of the present invention or separately by reacting the free base of a compound of the present invention with a suitable acid. Representative acids include, but are not limited to acetic, citric, aspartic, benzoic, benzenesulfonic, butyric, fumaric, hydrochloric, hydrobromic, hydroiodic, lactic, maleic, methanesulfonic, pamoic, pectinic, pivalic, propionic, succinic, tartaric, phosphic, glutamic, and p-toluenesulfonic. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained.

A compound of the present invention may be administered as a pharmaceutical composition containing a compound of the present invention in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions can be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or non-aqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions can also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Total daily dose of the compositions of the invention to be administered to a human or other mammal host in single or divided doses may be in amounts, for example, from 0.0001 to 300 mg/kg body weight daily and more usually 1 to 300 mg/kg body weight. The dose, from 0.0001 to 300 mg/kg body, may be given twice a day.

Abbreviations which have been used in the descriptions of the examples that follow are: DBU for 1,8-diazabicyclo [5.4.0]undec-7-ene; DMF for N,N-dimethylformamide; DMSO for dimethylsulfoxide; $Et_2O$ for diethyl ether; EtOAc for ethyl acetate; EtOH for ethanol; HPLC for high pressure liquid chromatography; LDA for lithium diisopropylamide; MeOH for methanol; psi for pounds per square inch; TFA for trifluoroacetic acid; THF for tetrahydrofuran, and TMS for trimethylsilane.

Compounds having formula I may be made by synthetic chemical processes, examples of which are shown herein below. It is meant to be understood that the order of the steps in the processes may be varied, that reagents, solvents and reaction conditions may be substituted for those specifically mentioned, and that vulnerable moieties may be protected and deprotected, as necessary.

Scheme 1

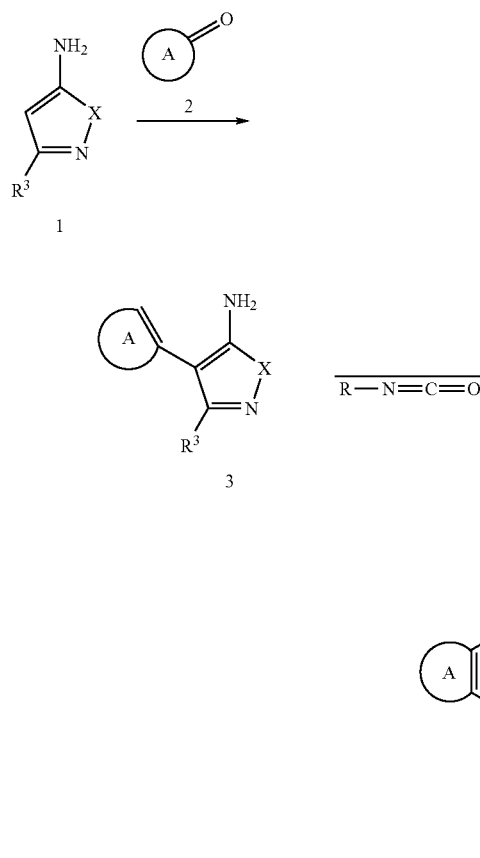

Compounds of formula (4) wherein X and R³ are as defined in formula (I) and ring A is cycloalkyl or heterocycle, unsubstituted or substituted as defined in formula (I), can be prepared from amines of formula (1) as shown in Scheme 1.

Amines of formula (1) can be reacted with unsubstituted or substituted cyclic ketones of formula (2) in the presence of acid such as, but not limited to, acetic acid, to provide alkenes of formula (3). The reaction is generally conducted at a temperature from about room temperature to about 70° C.

Compounds of formula (3) when treated with isocyanates such as, but not limited to, ethyl isocyanates, in pyridine or 4-methylpyridine, at reflux, provides compounds of formula (4).

Scheme 2

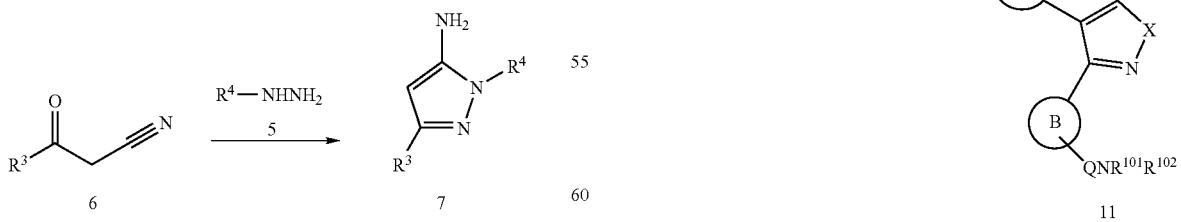

Aminopyrazoles (7) wherein R³ and R⁴ are as defined in formula (I) can be prepared from the reaction of hydrazines of formula (5) with an α-cyanoketone of formula (6), in a solvent such as ethanol and the like, at the reflux temperature of the solvent employed.

Scheme 3

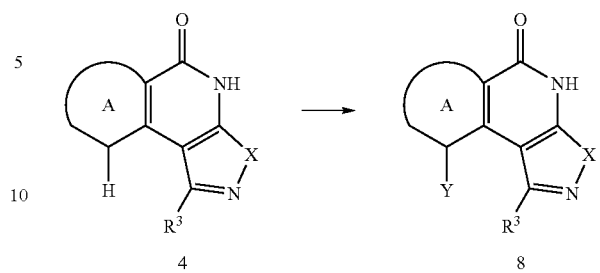

Compounds of formula (8) wherein X and R³ are as defined in formula (I), Y is $NR^A R^B$, alkoxy or haloalkoxy, and ring A is cycloalkyl or heterocycle, unsubstituted or substituted as defined in formula (I), and $R^A$ and $R^B$ are as defined in formula (I), can be prepared by (a) allylic halogenation, such as chlorination or bromination of ring A, and (b) displacement of the halide with an appropriate nucleophile of formula Y—H.

Allylic halogenation of compounds of formula (4) can be accomplished by treatment of (4) with a halogenating agent such as, but not limited to, bromosuccinimide or chlorosuccinimide, in the presence of catalytic amount of radical initiator such as, but not limited to, 2,2'-azobis(2-methylpropionitrile) or m-chloroperbenzoic acid (MCPBA), at elevated (for example 40-70° C.) or ambient temperature.

Displacement of the halide with a nucleophile can be achieved in the presence of a base such as, but not limited to, triethylamine or diisopropylethylamine, at a temperature from about room temperature to about 100° C.

Scheme 4

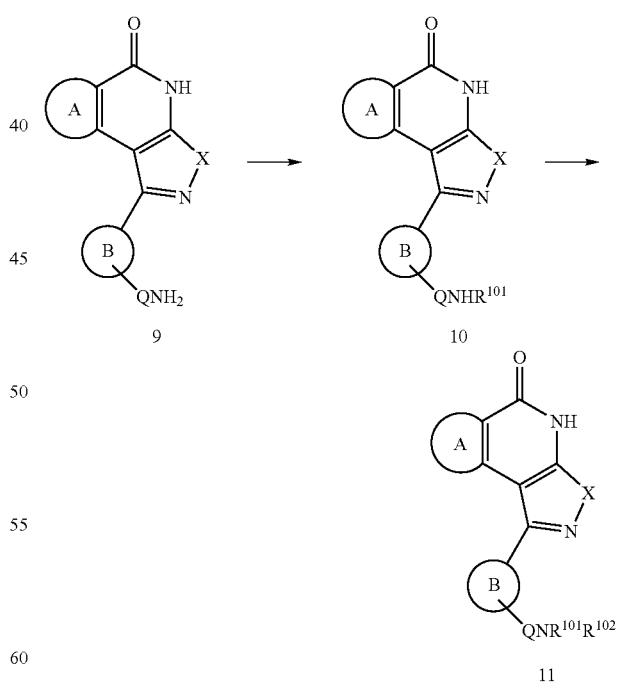

Compounds of formula (11) wherein X is as defined in formula (I), Q is alkylenyl, ring A is cycloalkyl or heterocycle, unsubstituted or substituted as defined in formula (I), ring B is aryl, heteroaryl, heterocycle or cycloalkyl, each of which is independently unsubstituted or substituted as described in formula (I), and $R^{101}$ and $R^{102}$ are independently selected from the group consisting of alkyl, cycloalkyl and heterocycle, can be prepared from primary amines of formula (9) as shown in Scheme 4.

Primary amines of formula (9) can be monoalkylated by compounds of formula $R^{101}$—Z, wherein Z is halides, triflates or mesylates, in the presence of a base such as, but not limited to, triethylamine or diisopropylethylamine, at a temperature from about room temperature to about 100° C. The second alkylation can be achieved with compounds of formula $R^{102}$—Z using similar reaction conditions to afford compounds of formula (11). The alkylation can be conducted sequentially or in one pot.

Alternatively, compounds of formula (10) can be obtained from primary amines of formula (9) via reductive amination conditions wherein (9) is treated with a ketones or aldehydes, in the presence of an acid such as, but not limited to, acetic acid, and a reducing agent such as, but not limited to, sodium cyanoborohydride. Compounds of formula (11) wherein $R^A$ and $R^B$ are independently alkyl, cycloalkyl or heterocycle, can be prepared from (10) using similar reaction conditions.

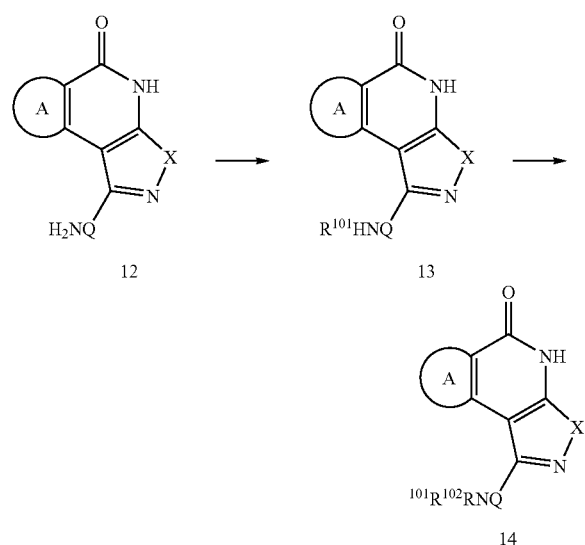

Scheme 5

Compounds of formula (14) wherein X is as defined in formula (I), Q is alkylenyl, ring A is cycloalkyl or heterocycle, unsubstituted or substituted as defined in formula (I), and $R^{101}$ and $R^{102}$ are independently alkyl, cycloalkyl or heterocycle, can be prepared from primary amines of formula (12) as shown in Scheme 5, using reaction conditions as described in Scheme 4.

The following Examples are intended as an illustration of and not a limitation upon the scope of the invention as defined in the appended claims. The compounds of this invention can be prepared by a variety of synthetic routes.

Example 1

1,3-dimethyl-3,4,6,7,8,9-hexahydropyrazolo[3,4-c]isoquinolin-5-one

The title compound was prepared as described in Winters, G; Sala, A; De Paoli, A.; Ferri, V. Synthesis 1984, 1052-1054.

Example 2

9-cyclobutylamino-1,3-dimethyl-3,4,6,7,8,9-hexahydropyrazolo[3,4-c]isoquinolin-5-one Example 2A 9-bromo-1,3-dimethyl-3,4,6,7,8,9-hexahydropyrazolo[3,4-c]isoquinolin-5-one A solution of EXAMPLE 1 (966 mg, 4.45 mmol) in a mixture of chloroform (30 mL) and N,N'-dimethylformamide (2 mL) was treated with N-bromosuccinimide (791 mg, 4.45 mmol) and catalytic 2,2'-azobis(2-methylpropionitrile) (5 mg) at 65° C. for 18 hours. The mixture was cooled, concentrated and the residue partitioned between ethyl acetate and brine. The organic phase was washed with water, concentrated and purified by flash chromatography on silica gel eluting with 50% ethyl acetate in hexanes to provide 1.14 g (87%) of the title compound. MS (DCI/NH$_3$) m/z 297 (M+H)$^+$.

Example 2B 9-cyclobutylamino-1,3-dimethyl-3,4,6,7,8,9-hexahydropyrazolo[3,4-c]isoquinolin-5-one Step A
To a solution of EXAMPLE 2A (40 mg, 0.14 mmol) in 1:1 tetrahydrofuran/N,N'-dimethylformamide (4 mL) was added cyclobutylamine (20 mg, 0.28 mmol) and diisopropylethylamine (49 □L, 0.28 mmol) and the mixture heated at 50° C. for 18 hours. The mixture was cooled, concentrated, and the residue purified by flash chromatography on silica gel using 70% ethyl acetate in hexanes to give the title compound.
Step B
Purification of the free base from Step A by HPLC (Zorbax, C-18, 250×2.54 column, Mobile phase A: 0.1% trifluoroacetic acid in water; B: 0.1% trifluoroacetic acid in acetonitrile; 0-100% gradient) provided 12 mg (30%) of the title compound as a trifluoroacetate salt. $^1$H NMR (CD$_3$OD) □ 1.85-1.97 (m, 3H), 1.98-2.12 (m, 2H), 2.18-2.39 (m, 4H), 2.40-2.53 (m, 2H), 2.56 (s, 3H), 2.76-2.90 (m, 1H), 3.84 (s, 3H), 4.04-4.19 (m, 1H), 4.79 (d, J=3.0 Hz, 1H), 13.70 (br s, 1H).

Example 3

1,3-dimethyl-9-morpholin-4-yl-3,4,6,7,8,9-hexahydropyrazolo[3,4-c]isoquinolin-5-one The title compound was prepared according to the procedure as described in Step A of EXAMPLE 2B, substituting morpholine for cyclobutylamine (21% yield). $^1$H NMR (CDCl$_3$) □ 1.60 (s, 1H), 1.65-1.79 (m, 2H), 1.84-1.96 (m, 1H), 2.04-2.16 (m, 1H), 2.50-2.57 (m, 2H), 2.57-2.64 (m, 6H), 3.54-3.62 (m, 2H), 3.62-3.71 (m, 2H), 3.99 (s, 3H), 4.08 (t, J=5.7 Hz, 1H), 13.70 (br s, 1H).

Example 4

1,3-dimethyl-9-piperidin-1-yl-3,4,6,7,8,9-hexahydropyrazolo[3,4-c]isoquinolin-5-one The title compound was prepared according to the procedure as described in Step A of EXAMPLE 2B, substituting piperidine for cyclobutylamine (72% yield). $^1$H NMR (DMSO-d6) ☐ 1.26-1.39 (m, 4H), 1.42-1.50 (m, 2H), 1.54-1.65 (m, 2H), 1.71-1.82 (m, 1H), 1.95-2.04 (m, 1H), 2.32-2.39 (m, 2H), 2.39-2.44 (m, 2H), 2.47 (s, 3H), 3.22-3.28 (m, 2H), 3.73 (s, 3H), 3.99-4.07 (m, 1H), 13.76 (br s, 1H).

Example 5

1,3-dimethyl-9-(4-methylpiperazin-1-yl)-3,4,6,7,8,9-hexahydropyrazolo[3,4-c]isoquinolin-5-one The title compound was prepared according to the procedure as described in Step A of EXAMPLE 2B, substituting 1-methylpiperazine for cyclobutylamine (37% yield). $^1$H NMR ($C_5D_5N$) ☐ 1.52-1.66 (m, 2H), 1.74-1.83 (m, 1H), 1.96-2.05 (m, 1H), 2.27-2.36 (m, 2H), 2.74 (s, 3H), 2.74 (s, 3H), 2.76-2.79 (m, 1H), 3.01-3.12 (m, 3H), 3.13-3.24 (m, 2H), 3.29-3.36 (m, 1H), 3.60-3.68 (m, 1H), 3.98 (s, 3H), 4.22 (t, J=5.7 Hz, 1H), 14.18 (br s, 1H).

Example 6

1-methyl-3,4,6,7,8,9-hexahydropyrazolo[3,4-c]isoquinolin-5-one

A mixture of 8.5 g of pyridine and 10 mL of concentrated hydrochloric acid was heated to 230° C., added to EXAMPLE 1 (217 mg, 1.0 mmol) and the mixture heated at 230° C. for 2 hours. After cooling, water was added and the suspension neutralized with 10% sodium hydroxide. Dichloromethane (50 mL) was added, the mixture was filtered and the solid collected, washed with dichloromethane and water and dried. Purification by HPLC (Zorbax, C-18, 250×2.54 column, Mobile phase A: 0.1% trifluoroacetic acid in water; B: 0.1% trifluoroacetic acid in acetonitrile; 0-100% gradient) provided 173 mg (73%) of the title compound as the trifluoroacetate salt. $^1$H NMR (DMSO-$d_6$) ☐ 1.63-1.73 (m, 4H), 2.29-2.34 (m, 2H), 2.46 (s, 3H), 2.75-2.80 (m, 2H), 11.28 (br s, 1H).

Example 7

1-methyl-3-phenyl-3,4,6,7,8,9-hexahydropyrazolo[3,4-c]isoquinolin-5-one

Example 7A 4-cyclohex-1-enyl-5-methyl-2-phenyl-2H-pyrazol-3-ylamine

A solution of 5-amino-3-methyl-1-phenylpyrazole (8.66 g, 50 mmol) in acetic acid (70 mL) was treated with cyclohexanone (10.6 mL, 100 mmol) at ambient temperature for 40 hours. The volatiles were removed and the residue diluted with water and 10% sodium hydroxide added until the pH=12. The mixture was stirred with 10 mL of hexane for 30 minutes and the solid collected by filtration, washed with water and hexane and dried to give 9.43 g (74%) of the title compound. MS (DCI): m/z 254 (M+H)$^+$.

Example 7B 1-methyl-3-phenyl-3,4,6,7,8,9-hexahydropyrazolo[3,4-c]isoquinolin-5-one To a solution of EXAMPLE 7A (1.26 g, 5 mmol) in pyridine (10 mL) was added ethyl isocyanate (1.18 mL, 15 mmol). The solution was heated at reflux for 7 hours, cooled, concentrated and the residue triturated with methanol. The solid was collected by filtration, washed with methanol and dried to give 493 mg (35%) of the title compound. $^1$H NMR (DMSO-$d_6$) ☐ 1.72-1.83 (m, 4H), 2.49-2.55 (m, 2H), 2.57 (s, 3H), 3.05 (t, J=5.2 Hz, 2H), 7.24 (t, J=7.4 Hz, 1H), 7.43-7.53 (m, 2H), 8.19 (d, J=7.7 Hz, 2H), 11.27 (br s, 1H).

Example 8

3-(2-dimethylaminoethyl)-1-methyl-3,4,6,7,8,9-hexahydropyrazolo[3,4-c]isoquinolin-5-one Example 8A 4-cyclohex-1-enyl-2-(2-dimethylaminoethyl)-5-methyl-2H-pyrazol-3-ylamine A solution of 2-(2-dimethylaminoethyl)-5-methyl-2H-pyrazol-3-ylamine (0.998 g, 5.93 mmol) in acetic acid (10 mL) was treated with cyclohexanone (1.23 mL, 11.86 mmol) at ambient temperature for two days. The volatiles were removed and the residue partitioned between dilute sodium hydroxide and ethyl acetate. The organic phase was washed with water, concentrated and the residue purified by flash chromatography on silica gel using 10% methanol in dichloromethane to give a solid (1.10 g, 75%). MS (DCI): m/z 249 (M+H)$^+$.

Example 8B 3-(2-dimethylaminoethyl)-1-methyl-3,4,6,7,8,9-hexahydropyrazolo[3,4-c]isoquinolin-5-one To a solution of EXAMPLE 8A (1.05 g, 4.22 mmol) in pyridine (10 mL) was added ethyl isocyanate (1.0 mL, 12.68 mmol) and the solution heated at reflux overnight. The mixture was cooled, stirred with 15 mL ethyl acetate at ambient temperature for 5 minutes and the solid collected by filtration, washed with ethyl acetate and dried to give 793 mg of the title compound. The mother liquor was concentrated and the residue recrystallized from ethyl acetate to give an additional 300 mg of the title compound (94% overall yield). $^1$H NMR (DMSO-$d_6$) ☐ 1.64-1.75 (m, 4H), 2.16 (s, 6H), 2.34-2.39 (m, 5H), 2.59 (t, J=6.4 Hz, 2H), 2.83-2.87 (m, 2H), 4.18 (t, J=6.6 Hz, 2H).

Example 9

3-methyl-3,4,6,7,8,9-hexahydropyrazolo[3,4-c]isoquinolin-5-one

The title compound was prepared according to the procedure for EXAMPLE 8, substituting 1-methyl-1H-pyrazol-5-ylamine for 2-(2-dimethylaminoethyl)-5-methyl-2H-pyrazol-3-ylamine. $^1$H NMR (DMSO-$d_6$): ☐ 1.67-1.77 (m, 4H), 2.38 (br d, J=1.8 Hz, 2H), 2.72 (br d, J=1.8 Hz, 2H), 3.82 (s, 3H), 7.68 (s, 1H), 11.90 (br s, 1H).

Example 10

1-methyl-6,7,8,9-tetrahydro-4H-isoxazolo[5,4-c]isoquinolin-5-one

Example 10A

4-Cyclohex-1-enyl-3-methyl-isoxazol-5-ylamine

The title compound was prepared according to the procedure for EXAMPLE 7A, substituting 5-amino-3-methylisoxazole for 5-amino-3-methyl-1-phenylpyrazole (72% yield). MS (DCI/NH$_3$) m/z 179 (M+H)$^+$.

Example 10B 1-methyl-6,7,8,9-tetrahydro-4H-isoxazolo[5,4-c]isoquinolin-5-one The title compound was prepared according to the procedure as described in EXAMPLE 7B, substituting EXAMPLE 10A for EXAMPLE 7A (67% yield). $^1$H NMR (DMSO-d6) □ 1.69-1.79 (m, 4H), 2.46 (t, J=4.6 Hz, 2H), 2.49 (s, 3H), 2.95 (t, J=4.8 Hz, 2H), 12.16 (br s, 1H).

Example 11

1-phenyl-6,7,8,9-tetrahydro-4H-isoxazolo[5,4-c]isoquinolin-5-one

Example 11A 4-cyclohex-1-enyl-3-phenylisoxazol-5-ylamine

The title compound was prepared according to the procedure as described in EXAMPLE 7A, substituting 5-amino-3-phenylisoxazole for 5-amino-3-methyl-1-phenylpyrazole (50% yield). MS (DCI/NH$_3$) m/z 241 (M+H)$^+$.

Example 11B 1-phenyl-6,7,8,9-tetrahydro-4H-isoxazolo[5,4-c]isoquinolin-5-one The title compound was prepared according to the procedure as described in EXAMPLE 7B, substituting EXAMPLE 11A for EXAMPLE 7A (3% yield). $^1$H NMR (C$_5$D$_5$N) □ 1.43-1.52 (m, 2H), 1.65-1.75 (m, 2H), 2.55 (t, J=6.3 Hz, 2H), 2.81 (t, J=6.4 Hz, 2H), 7.50-7.57 (m, 3H), 7.80-7.87 (m, 2H), 14.15 (br s, 1H).

Example 12

3-methyl-1-phenyl-3,4,6,7,8,9-hexahydropyrazolo[3,4-c]isoquinolin-5-one

Example 12A 4-cyclohex-1-enyl-2-methyl-5-phenyl-2H-pyrazol-3-ylamine

The title compound was prepared according to the procedure as described in EXAMPLE 7A, substituting 5-amino-1-methyl-3-phenylpyrazole for 5-amino-3-methyl-1-phenylpyrazole (36% yield). MS (DCI/NH$_3$) m/z 254 (M+H)$^+$.

Example 12B 3-methyl-1-phenyl-3,4,6,7,8,9-hexahydropyrazolo[3,4-c]isoquinolin-5-one The title compound was prepared according to the procedure as described in EXAMPLE 7B, substituting EXAMPLE 12A for EXAMPLE 7A (66% yield). $^1$H NMR (C$_5$D$_5$N) □ 1.44-1.56 (m, 2H), 1.66-1.76 (m, 2H), 2.68 (t, J=5.7 Hz, 2H), 2.87 (t, J=5.8 Hz, 2H), 4.06 (s, 3H), 7.43-7.49 (m, 1H), 7.51-7.56 (m, 2H), 7.56-7.58 (m, 1H), 7.89 (t, J=1.7 Hz, 1H), 14.15 (br s, 1H).

Example 13

3-benzyl-1-methyl-3,4,6,7,8,9-hexahydropyrazolo[3,4-c]isoquinolin-5-one

Example 13A 2-benzyl-4-cyclohex-1-enyl-5-methyl-2H-pyrazol-3-ylamine

The title compound was prepared according to the procedure as described in EXAMPLE 7A, substituting 2-benzyl-5-methyl-2H-pyrazol-3-ylamine for 5-amino-3-methyl-1-phenylpyrazole (45% yield). MS (DCI/NH$_3$) m/z 268 (M+H)$^+$.

Example 13B 3-benzyl-1-methyl-3,4,6,7,8,9-hexahydropyrazolo[3,4-c]isoquinolin-5-one The title compound was prepared according to the procedure as described in EXAMPLE 7B, substituting EXAMPLE 13A for EXAMPLE 7A (55% yield). $^1$H NMR (C$_5$D$_5$N) □ 1.64-1.78 (m, 4H), 2.57 (s, 3H), 2.80-2.91 (m, 4H), 5.67 (s, 2H), 7.21-7.24 (m, 1H), 7.26-7.32 (m, 2H), 7.44-7.49 (m, 2H), 14.15 (br s, 1H).

Example 14

3-phenyl-3,4,6,7,8,9-hexahydropyrazolo[3,4-c]isoquinolin-5-one

Example 14A 4-cyclohex-1-enyl-2-phenyl-2H-pyrazol-3-ylamine

The title compound was prepared according to the procedure for EXAMPLE 7A, substituting 5-amino-1-phenylpyrazole for 5-amino-3-methyl-1-phenylpyrazole (18% yield). MS (DCI/NH$_3$) m/z 240 (M+H)$^+$.

Example 14B 3-phenyl-3,4,6,7,8,9-hexahydropyrazolo[3,4-c]isoquinolin-5-one

The title compound was prepared according to the procedure as described in EXAMPLE 7B, substituting EXAMPLE 14A for EXAMPLE 7A (23% yield). $^1$H NMR (C$_5$D$_5$N) □ 1.66-1.80 (m, 4H), 2.79 (t, J=6.1 Hz, 2H), 2.85 (t, J=6.1 Hz, 2H), 7.25-7.30 (m, 1H), 7.41-7.50 (m, 2H), 8.19 (s, 1H), 8.54 (dd, J=8.6, 1.2 Hz, 2H), 14.15 (br s, 1H).

Example 15

3-methyl-1-thiophen-2-yl-3,4,6,7,8,9-hexahydropyrazolo[3,4-c]isoquinolin-5-one

Example 15A 4-cyclohex-1-enyl-2-methyl-5-thiophen-2-yl-2H-pyrazol-3-ylamine

The title compound was prepared according to the procedure as described in EXAMPLE 7A, substituting 5-amino-1- methyl-3-(2-thienyl)pyrazole for 5-amino-3-methyl-1-phenylpyrazole (30% yield). MS (DCI/NH$_3$) m/z 260 (M+H)$^+$.

Example 15B 3-methyl-1-thiophen-2-yl-3,4,6,7,8,9-hexahydropyrazolo[3,4-c]isoquinolin-5-one The title compound was prepared according to the procedure as described in EXAMPLE 7B, substituting EXAMPLE 15A for EXAMPLE 7A (73% yield). $^1$H NMR (C$_5$D$_5$N) ☐ 1.54-1.60 (m, 2H), 1.69-1.77 (m, 2H), 2.87 (t, J=6.4 Hz, 4H), 4.02 (s, 3H), 7.24 (dd, J=5.2, 3.7 Hz, 1H), 7.54 (dd, J=3.4, 0.9 Hz, 1H), 7.57 (d, J=0.9 Hz, 1H), 14.15 (br s, 1H).

Example 16

1-isopropyl-3-methyl-3,4,6,7,8,9-hexahydropyrazolo[3,4-c]isoquinolin-5-one

Example 16A 4-cyclohex-1-enyl-5-isopropyl-2-methyl-2H-pyrazol-3-ylamine

The title compound was prepared according to the procedure as described in EXAMPLE 7A, substituting 3-isopropyl-1-methyl-1H-pyrazol-5-amine for 5-amino-3-methyl-1-phenylpyrazole (13% yield). MS (DCI/NH$_3$) m/z 220 (M+H)$^+$.

Example 16B 1-isopropyl-3-methyl-3,4,6,7,8,9-hexahydropyrazolo[3,4-c]isoquinolin-5-one The title compound was prepared according to the procedure as described in EXAMPLE 7B, substituting EXAMPLE 16A for EXAMPLE 7A (44% yield). $^1$H NMR (C$_5$D$_5$N) ☐ 1.51 (d, J=6.7 Hz, 6H), 1.68-1.81 (m, 4H), 2.87 (m, 2H), 2.93 (m, 2H), 3.32-3.47 (m, 1H), 3.95 (s, 3H), 13.45 (br, s 1H).

Example 17

1-cyclopropyl-3-methyl-3,4,6,7,8,9-hexahydropyrazolo[3,4-c]isoquinolin-5-one

Example 17A 4-cyclohex-1-enyl-5-cyclopropyl-2-methyl-2H-pyrazol-3-ylamine

The title compound was prepared according to the procedure as described in EXAMPLE 7A, substituting 3-cyclopropyl-1-methyl-1H-pyrazol-5-amine for 5-amino-3-methyl-1-phenylpyrazole (50% yield). MS (DCI/NH$_3$) m/z 218 (M+H)$^+$.

Example 17B 1-cyclopropyl-3-methyl-3,4,6,7,8,9-hexahydropyrazolo[3,4-c]isoquinolin-5-one The title compound was prepared according to the procedure as described in EXAMPLE 7B, substituting EXAMPLE 17A for EXAMPLE 7A (83% yield). $^1$H NMR (C$_5$D$_5$N) ☐ 0.92-1.01 (m, 2H), 1.17-1.28 (m, 2H), 1.69-1.82 (m, 4H), 2.16-2.27 (m, 1H), 2.86 (t, J=4.4 Hz, 2H), 3.06 (t, J=4.4 Hz, 2H), 3.91 (s, 3H), 13.46 (br s, 1H).

Example 19

1-cyclopropyl-3-methyl-4,6,8,9-tetrahydro-3H-7-oxa-2,3,4-triaza-cyclopenta[a]naphthalen-5-one Example 19A 5-cyclopropyl-4-(3,6-dihydro-2H-pyran-4-yl)-2-methyl-2H-pyrazol-3-ylamine The title compound was prepared according to the procedure as described in EXAMPLE 7A, substituting 3-cyclopropyl-1-methyl-1H-pyrazol-5-amine for 5-amino-3-methyl-1-phenylpyrazole and substituting tetrahydro-4H-pyran-4-one for cyclohexanone (67% yield). MS (DCI/NH$_3$) m/z 220 (M+H)$^+$.

Example 19B 1-cyclopropyl-3-methyl-4,6,8,9-tetrahydro-3H-7-oxa-2,3,4-triaza-cyclopenta[a]naphthalen-5-one The title compound was prepared according to the procedure as described in EXAMPLE 7B, substituting EXAMPLE 19A for EXAMPLE 7A (20% yield). $^1$H NMR (DMSO-d6) ☐ 0.77-0.83 (m, 2H), 0.83-0.90 (m, 2H), 2.04-2.18 (m, 1H), 2.96-3.11 (m, 2H), 3.72 (s, 3H), 3.87 (t, J=5.6 Hz, 2H), 4.41 (s, 2H), 11.99 (br s, 1H)

Example 20

1-(3-chlorophenyl)-3-methyl-3,4,6,7,8,9-hexahydropyrazolo[3,4-c]isoquinolin-5-one Example 20A 5-(3-chlorophenyl)-4-cyclohex-1-enyl-2-methyl-2H-pyrazol-3-ylamine The title compound was prepared according to the procedure as described in EXAMPLE 7A, substituting 5-(3-chlorophenyl)-2-methyl-2H-pyrazole-3-ylamine for 5-amino-3-methyl-1-phenylpyrazole (14% yield). MS (DCI/NH$_3$) m/z 288 (M+H)$^+$.

Example 20B 1-(3-chlorophenyl)-3-methyl-3,4,6,7,8,9-hexahydropyrazolo[3,4-c]isoquinolin-5-one The title compound was prepared according to the procedure as described in EXAMPLE 7B, substituting EXAMPLE 20A for EXAMPLE 7A (3% yield). $^1$H NMR (DMSO-d6) ☐ 1.52-1.62 (m, 2H), 1.64-1.74 (m, 2H), 2.37-2.48 (m, 4H), 3.88 (s, 3H), 7.47-7.51 (m, 3H), 7.53-7.58 (m, 1H), 12.04 (br s, 1H).

Example 21

3-methyl-1-thiophen-2-yl-4,6,7,8-tetrahydro-3H-2,3,4-triaza-as-indacen-5-one

Example 21A 4-cyclopent-1-enyl-2-methyl-5-thiophen-2-yl-2H-pyrazol-3-ylamine The title compound was prepared according to the procedure as described in EXAMPLE 7A, substituting 5-amino-1-methyl-3-(2-thienyl)pyrazole for 5-amino-3-methyl-1-phenylpyrazole and substituting cyclopentanone for cyclohexanone (20% yield). MS (DCI/NH$_3$) m/z 246 (M+H)$^+$.

Example 21B 3-methyl-1-thiophen-2-yl-4,6,7,8-tetrahydro-3H-2,3,4-triaza-as-indacen-5-one The title compound was prepared according to the procedure as described in EXAMPLE 7B, substituting EXAMPLE 21A for EXAMPLE 7A (70% yield). $^1$H NMR (DMSO-d6) ☐ 2.07 (dt, J=15.0, 7.5 Hz, 2H), 2.71 (t, J=7.4 Hz, 2H), 3.16 (t, J=7.4 Hz, 2H), 3.89 (s, 3H), 7.15 (dd, J=4.6, 4.0 Hz, 1H), 7.45 (d, J=3.7 Hz, 1H), 7.56 (d, J=5.2 Hz, 1H), 11.94 (br s, 1H).

Example 22

1-cyclopropyl-3-methyl-4,6,7,8-tetrahydro-3H-2,3,4-triaza-as-indacen-5-one

Example 22A 4-cyclopent-1-enyl-5-cyclopropyl-2-methyl-2H-pyrazol-3-ylamine

The title compound was prepared according to the procedure as described in EXAMPLE 7A, substituting 3-cyclopropyl-1-methyl-1H-pyrazol-5-amine for 5-amino-3-methyl-1-phenylpyrazole and substituting cyclopentanone for cyclohexanone (30% yield). MS (DCI/NH$_3$) m/z 204 (M+H)$^+$.

Example 22B 1-cyclopropyl-3-methyl-4,6,7,8-tetrahydro-3H-2,3,4-triaza-as-indacen-5-one The title compound was prepared according to the procedure as described in EXAMPLE 7B, substituting EXAMPLE 22A for EXAMPLE 7A (60% yield). $^1$H NMR (DMSO-d6) ☐ 0.74-0.83 (m, 2H), 0.88 (dd, J=8.2, 2.4 Hz, 2H), 1.97-2.12 (m, 3H), 2.65 (t, J=6.9 Hz, 2H), 3.12 (t, J=7.3 Hz, 2H), 3.72 (s, 3H), 11.78 (br s, 1H).

Example 23

1-cyclopropyl-3-methyl-4,6,7,8,9,10-hexahydro-3H-2,3,4-triazacyclohepta[e]inden-5-one

Example 23A

4-Cyclohept-1-enyl-5-cyclopropyl-2-methyl-2H-pyrazol-3-ylamine

The title compound was prepared according to the procedure as described in EXAMPLE 7A, substituting 3-cyclopropyl-1-methyl-1H-pyrazol-5-amine for 5-amino-3-methyl-1-phenylpyrazole and substituting cycloheptanone for cyclohexanone (6% yield). MS (DCI/NH$_3$) m/z 232 (M+H)$^+$.

Example 23B 1-cyclopropyl-3-methyl-4,6,7,8,9,10-hexahydro-3H-2,3,4-triazacyclohepta[e]inden-5-one The title compound was prepared according to the procedure as described in EXAMPLE 7B, substituting EXAMPLE 23A for EXAMPLE 7A (30% yield). $^1$H NMR (DMSO-d6) ☐ 0.76-0.80 (m, 2H), 0.82-0.89 (m, 2H), 1.41-1.48 (m, 2H), 1.59-1.66 (m, 2H), 1.83 (ddd, J=11.2, 6.0, 5.7 Hz, 2H), 2.02-2.10 (m, 1H), 2.74-2.83 (m, 2H), 3.14-3.22 (m, 2H), 3.72 (s, 3H), 11.70 (br s, 1H).

Example 24 benzyl 3-(3-methyl-5-oxo-4,5,6,7,8,9-hexahydropyrazolo[3,4-c]isoquinolin-1-yl)-pyrrolidine-1-carboxylate

Example 24A

N-carbobenzyloxypyrrolidine-3-carboxylic acid methyl ester

To a solution of N-carbobenzyloxypyrrolidine-3-carboxylic acid (10.15 g, 40.72 mmol) and iodomethane (5.08 mL, 81.44 mmol) in N,N'-dimethylformamide (80 mL) was added powdered potassium hydrogen carbonate (8.15 g, 81.44 mmol) and the reaction mixture stirred at ambient temperature for 5 hours. The mixture was partitioned between ethyl acetate and brine and the organic phase washed with water and concentrated. The residue was purified by flash chromatography on silica gel using 5-50% ethyl acetate in hexane to give the title compound (10.59 g, 99%). MS(DCI): m/z 264 (M+H)$^+$.

Example 24B benzyl 3-(2-cyanoacetyl)-pyrrolidine-1-carboxylate

To a solution of acetonitrile (708 µL, 13.5 mmol) in tetrahydrofuran (30 mL) was added n-butyl lithium (1.6 M solution in hexane, 7.75 mL, 12.4 mmol) at −78° C. The solution was stirred at −78° C. for 10 minutes and a solution of EXAMPLE 24A (3.0 g, 11.34 mmol) in 10 mL of tetrahydrofuran was added. The mixture was stirred at −78° C. for 1 hour and was warmed up to −20° C. over 3 hours. Water was added and the mixture acidified to pH 3 with 2N hydrochloric acid. The mixture was partitioned between ethyl acetate and brine and the organic phase concentrated. The residue was purified by flash chromatography on silica gel using 30-80% ethyl acetate in hexane to give the title compound (1.91 g, 61%). MS(DCI): m/z 273 (M+1)$^+$.

Example 24C benzyl 3-(5-amino-1-methyl-1H-pyrazol-3-yl)-pyrrolidine-1-carboxylate A solution of EXAMPLE 24B (1.9 g, 7 mmol) and methylhydrazine (367 µL, 7 mmol) in ethanol (15 mL) was heated at reflux for 4 hours. After cooling, the mixture was concentrated and the residue purified by flash chromatography on silica gel using 0-15% methanol in dichloromethane to give the title compound (1.78 g, 85%). MS(DCI): m/z 301 (M+1)+.

Example 24D benzyl 3-(5-amino-4-cyclohex-1-enyl-1-methyl-1H-pyrazol-3-yl)pyrrolidine-1-carboxylate A solution of EXAMPLE 24C (1.78 g, 5.92 mmol) and cyclohexanone (1.23 mL, 11.85 mmol) in acetic acid (10 mL) was stirred at ambient temperature overnight and at 55° C. for 1 day. The acetic acid was removed and the residue partitioned between sodium bicarbonate solution and ethyl acetate. The organic phase was washed with water, concentrated and the residue purified by flash chromatography on silica gel using 70-90% ethyl acetate in hexane to provide the title compound as a light yellow solid (1.19 g, 53%). MS (DCI): m/z 381 (M+H)+.

Example 24E benzyl 3-(3-methyl-5-oxo-4,5,6,7,8,9-hexahydropyrazolo[3,4-c]isoquinolin-1-yl)-pyrrolidine-1-carboxylate To a stirring solution of EXAMPLE 24D (0.967 g, 2.54 mmol) in pyridine (10 mL) was added ethyl isocyanate (0.6 mL, 7.62 mmol) and the solution heated at reflux for 24 hours. After cooling, the mixture was concentrated and the residue recrystallized from methanol. The white solid was collected by filtration, washed with methanol and dried to give the title compound (794 mg, 77%). $^1$H NMR (DMSO-$d_6$): ☐ 1.66-1.77 (m, 4H), 2.01-2.17 (m, 1H), 2.18-2.27 (m, 1H), 2.37-2.43 (m, 2H), 2.86-2.92 (m, 2H), 3.33-3.46 (m, 1H), 3.49-3.64 (m, 2H), 3.68-3.76 (m, 1H), 3.76 (s, 3H), 3.77-3.85 (m, 1H), 5.08 (s, 2H), 7.29-7.35 (m, 1H), 7.34-7.39 (m, 5H).

Example 25

3-methyl-1-pyrrolidin-3-yl-3,4,6,7,8,9-hexahydropyrazolo[3,4-c]isoquinolin-5-one A solution of EXAMPLE 24E (766 mg, 1.88 mmol) in a mixture of dichloromethane (30 mL) and methanol (30 mL) was treated with 10% palladium on carbon (150 mg) under hydrogen at ambient temperature for 6 hours. Solid material was filtered off and the filtrate concentrated to provide the title compound (564 mg, 100%). $^1$H NMR (DMSO-$d_6$): ☐ 1.67-1.79 (m, 4H), 2.01-2.11 (m, 1H), 2.22-2.32 (m, 1H), 2.38-2.43 (m, 2H), 2.85-2.91 (m, 2H), 3.16-3.26 (m, 2H), 3.30 (dd, J=11.0, 8.0 Hz, 1H), 3.46 (dd, J=11.2, 7.5 Hz, 1H), 3.78 (s, 3H), 3.81-3.88 (m, 1H).

Example 26

3-methyl-1-(1-methylpyrrolidin-3-yl)-3,4,6,7,8,9-hexahydropyrazolo[3,4-c]isoquinolin-5-one To a solution of EXAMPLE 25 (86 mg, 0.316 mmol) in methanol (6 mL) was added formaldehyde (37 wt % in water, 118 μL, 1.58 mmol) at ambient temperature and the solution stirred for 1 hour. Sodium cyanoborohydride (99 mg, 1.58 mmol) was added and the mixture stirred overnight and concentrated. The residue was purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt (110 mg, 79%). $^1$H NMR (CD$_3$OD): ☐ 1.77-1.87 (m, 4H), 2.24-2.37 (m, 1H), 2.49 (t, J=6.0 Hz, 2H), 2.66 (dd, J=13.6, 6.0 Hz, 0.5H), 2.90-2.96 (m, 2.5H), 3.02 (s, 1H), 3.08 (s, 1H), 3.24-3.31 (m, 1H), 3.44 (dd, J=1.4, 7.8 Hz, 0.5H), 3.62 (dd, J=1.3, 7.6 Hz, 0.5H), 3.72-3.83 (m, 0.5H), 3.84 (s, 3H), 3.84 (m, 0.5H), 3.97-4.03 (m, 0.5H), 4.04-4.14 (m, 1H), 4.19-4.26 (m, 0.5H).

Example 27

1-(1-isopropylpyrrolidin-3-yl)-3-methyl-3,4,6,7,8,9-hexahydropyrazolo[3,4-c]isoquinolin-5-one The trifluoroacetate salt of the title compound was prepared according to the procedure as described in EXAMPLE 26, substituting acetone for formaldehyde (77% yield). $^1$H NMR (CD$_3$OD): ☐ 1.39-1.46 (m, 6H), 1.77-1.88 (m, 4H), 2.23-2.32 (m, 1H), 2.44-2.53 (m, 2.5H), 2.54-2.62 (m, 0.5H), 2.87-3.00 (m, 2H), 3.33-3.42 (m, 1H), 3.51-3.56 (m, 0.5H), 3.58-3.66 (m, 1H), 3.66-3.72 (m, 1H), 3.74-3.79 (m, 0.5H), 3.84 (s, 3H), 3.92 (dd, J=11.6, 7.3 Hz, 0.5H), 3.97 (dd, J=11.4, 5.0 Hz, 0.5H), 4.03-4.11 (m, 0.5H), 4.14-4.21 (m, 0.5H).

Example 28

3-methyl-1-(1-propylpyrrolidin-3-yl)-3,4,6,7,8,9-hexahydropyrazolo[3,4-c]isoquinolin-5-one The trifluoroacetate salt of the title compound was prepared according to the procedure as described in EXAMPLE 26, substituting propionaldehyde for formaldehyde (67% yield). $^1$H NMR (CD$_3$OD): ☐ 1.06 (t, J=7.5 Hz, 3H), 1.75-1.89 (m, 6H), 2.21-2.35 (m, 1H), 2.43-2.54 (m, 2.5H), 2.58-2.66 (m, 0.5H), 2.89-2.99 (m, 2H), 3.19-3.26 (m, 1H), 3.29-3.35 (m, 1H), 3.48 (dd, J=11.5, 8.1 Hz, 0.5H), 3.64 (dd, J=11.0, 7.4 Hz, 0.5H), 3.71-3.82 (m, 1H), 3.84 (s, 3H), 3.98 (dd, J=11.4, 7.67 Hz, 0.5H), 4.04-4.11 (m, 1H), 4.17-4.23 (m, 0.5H).

Example 29

1-(1-cyclopropylmethylpyrrolidin-3-yl)-3-methyl-3,4,6,7,8,9-hexahydropyrazolo[3,4-c]isoquinolin-5-one The trifluoroacetate salt of the title compound was prepared according to the procedure as described in EXAMPLE 26, substituting cyclopropanecarboxyaldehyde for formaldehyde (66% yield). $^1$H NMR (CD$_3$OD): ☐ 0.45-0.50 (m, 2H), 0.74-0.79 (m, 2H), 1.14-1.23 (m, 1H), 1.77-1.88 (m, 4H), 2.23-2.35 (m, 1H), 2.47-2.54 (m, 2.5H), 2.59-2.67 (m, 0.5H), 2.88-3.00 (m, 2H), 3.18 (dd, J=7.2, 2.0 Hz, 1H), 3.26 (dd, J=7.3, 1.2 Hz, 1H), 3.29-3.40 (m, 1H), 3.56 (dd, J=11.6, 8.2 Hz, 0.5H), 3.69 (dd, J=11.6, 7.6 Hz, 0.5H), 3.76-3.84 (m, 1H), 3.84 (s, 1.5H), 3.85 (s, 1.5H), 3.97-4.04 (m, 0.5H), 4.08-4.16 (m, 1H), 4.18-4.24 (m, 0.5H).

Example 30

1-(1-cyclobutylpyrrolidin-3-yl)-3-methyl-3,4,6,7,8,9-hexahydropyrazolo[3,4-c]isoquinolin-5-one The trifluoroacetate salt of the title compound was prepared according to the procedure as described in EXAMPLE 26, substituting cyclobutanone for formaldehyde (69% yield). ¹H NMR (CD₃OD): δ 1.77-1.88 (m, 4H), 1.89-2.00 (m, 2H), 2.21-2.33 (m, 3H), 2.34-2.43 (m, 2H), 2.49 (t, J=5.8 Hz, 2.5H), 2.54-2.63 (m, 0.5H), 2.87-3.00 (m, 2H), 3.19-3.27 (m, 1H), 3.42 (dd, J=11.6, 8.2 Hz, 0.5H), 3.53 (dd, J=11.6, 7.6 Hz, 0.5H), 3.62-3.74 (m, 1H), 3.84 (s, 3H), 3.88-3.93 (m, 1H), 3.95-4.01 (m, 0.5H), 4.02-4.06 (m, 0.5H), 4.07-4.13 (m, 0.5H), 4.16-4.22 (m, 0.5H).

Example 31

(S)-3-methyl-1-pyrrolidin-2-yl-3,4,6,7,8,9-hexahydropyrazolo[3,4-c]isoquinolin-5-one The trifluoroacetate salt of the title compound was prepared according to the procedure as described in EXAMPLES 24B-E and EXAMPLE 25, substituting N-carbobenzyloxy-L-proline methyl ester for EXAMPLE 24A. ¹H NMR (CD₃OD): δ 1.78-1.91 (m, 4H), 2.13-2.20 (m, 1H), 2.22-2.31 (m, 2H), 2.47-2.57 (m, 3H), 2.87-2.99 (m, 2H), 3.39-3.48 (m, 1H), 3.51-3.61 (m, 1H), 3.88 (s, 3H), 4.98-5.41 (m, 1H).

Example 32

(S)-3-Methyl-1-(1-methylpyrrolidin-2-yl)-3,4,6,7,8,9-hexahydropyrazolo[3,4-c]isoquinolin-5-one A solution of EXAMPLE 31 (100 mg, 0.37 mmol), triethylamine (52 μL, 0.37 mmol) and formaldehyde (37% in water, 31 μL, 1.11 mmol) in 1:1 methanol/N,N'-dimethylformamide (6 mL) was stirred at ambient temperature for 2 hours. Sodium cyanoborohydride (70 mg, 1.11 mmol) and zinc chloride (50 mg, 0.37 mmol) were added and the mixture stirred at 50° C. for 18 hours. The mixture was concentrated and the residue purified by HPLC (Zorbax C-8, 0.1% trifluoroacetic acid/acetonitrile/water) to provide the trifluoroacetate salt of the title compound. Treatment of a methanol solution of the trifluoroacetate salt with a solution of hydrochloric acid in ether gave the title compound as the hydrochloride salt (13 mg, 12%). ¹H NMR (CD₃OD): δ 1.79-1.91 (m, 4H), 2.10-2.24 (m, 2H), 2.26-2.36 (m, 1H), 2.49-2.55 (m, 2H), 2.69-2.78 (m, 1H), 2.80-2.88 (m, 1H), 2.93-3.01 (m, 1H), 2.96 (s, 3H), 3.32-3.39 (m, 1H), 3.81-3.87 (m, 1H), 3.91 (s, 3H), 4.97 (t, J=8.4 Hz, 1H).

Example 33

(S)-3-methyl-1-(1-propyl-pyrrolidin-2-yl)-3,4,6,7,8,9-hexahydropyrazolo[3,4-c]isoquinolin-5-one The title compound as the hydrochloride salt was prepared according to the procedure for EXAMPLE 32, substituting propionaldehyde for formaldehyde (10% yield). ¹H NMR (CD₃OD): δ 0.97 (t, J=7.3 Hz, 3H), 1.64-1.77 (m, 2H), 1.80-1.90 (m, 4H), 2.06-2.14 (m, 1H), 2.15-2.23 (m, 1H), 2.23-2.32 (m, 1H), 2.48-2.56 (m, 2H), 2.66-2.74 (m, 1H), 2.79-2.87 (m, 1H), 2.91-3.00 (m, 1H), 3.07-3.16 (m, 1H), 3.22-3.29 (m, 2H), 3.85-3.90 (m, 1H), 3.91 (s, 3H), 5.01 (t, J=8.4 Hz, 1H).

Example 34

(S)-1-(1-isopropylpyrrolidin-2-yl)-3-methyl-3,4,6,7,8,9-hexahydropyrazolo[3,4-c]isoquinolin-5-one The hydrochloride salt of the title compound was prepared according to the procedure as described in EXAMPLE 32, substituting acetone for formaldehyde (42% yield). ¹H NMR (CD₃OD): δ 1.33 (dd, J=6.7, 3.0 Hz, 6H), 1.79-1.92 (m, 4H), 2.03-2.12 (m, 1H), 2.15-2.28 (m, 2H), 2.52 (t, J=6.1 Hz, 2H), 2.63-2.72 (m, 1H), 2.81-2.91 (m, 1H), 2.92-3.01 (m, 1H), 3.35-3.43 (m, 1H), 3.69-3.77 (m, 2H), 3.92 (s, 3H), 5.10 (t, J=7.8 Hz, 1H).

Example 35 (A-936655.3)

(S)-1-(1-cyclopropylmethylpyrrolidin-2-yl)-3-methyl-3,4,6,7,8,9-hexahydropyrazolo[3,4-c]isoquinolin-5-one The hydrochloride salt of the title compound was prepared according to the procedure as described in EXAMPLE 32, substituting cyclopropane carboxaldehyde for formaldehyde (36% yield). ¹H NMR (CD₃OD): δ 0.35-0.42 (m, 2H), 0.65-0.71 (m, 2H), 1.06-1.13 (m, 1H), 1.78-1.92 (m, 4H), 2.05-2.13 (m, 1H), 2.18-2.25 (m, 1H), 2.27-2.33 (m, 1H), 2.48-2.55 (m, 2H), 2.67-2.76 (m, 1H), 2.79-2.88 (m, 1H), 2.91-3.00 (m, 1H), 3.08-3.19 (m, 2H), 3.36-3.42 (m, 1H), 3.91 (s, 3H), 3.96-4.01 (m, 1H), 5.02 (t, J=8.5 Hz, 1H).

Example 36

(S)-1-(1-cyclobutylpyrrolidin-2-yl)-3-methyl-3,4,6,7,8,9-hexahydropyrazolo[3,4-c]isoquinolin-5-one The hydrochloride salt of the title compound was prepared according to the procedure as described in EXAMPLE 32, substituting cyclobutanone for formaldehyde (27% yield). ¹H NMR (CD₃OD): δ 1.71-1.83 (m, 4H), 1.85-1.93 (m, 3H), 1.94-2.02 (m, 1H), 2.17-2.26 (m, 3H), 2.26-2.31 (m, 1H), 2.32-2.39 (m, 1H), 2.49-2.56 (m, 2H), 2.62-2.71 (m, 1H), 2.83-2.91 (m, 1H), 2.91-3.00 (m, 1H), 3.23-3.29 (m, 1H), 3.73-3.80 (m, 1H), 3.93 (s, 3H), 3.94-4.00 (m, 1H), 4.93 (t, J=7.6 Hz, 1H).

Example 37

(S)-1-(1-isobutylpyrrolidin-2-yl)-3-methyl-3,4,6,7,8,9-hexahydropyrazolo[3,4-c]isoquinolin-5-one The hydrochloride salt of the title compound was prepared according to the procedure as described in EXAMPLE 32, substituting isobutyraldehyde for formaldehyde (29% yield). ¹H NMR (CD₃OD): δ 1.09 (d, J=6.7 Hz, 6H), 1.80-1.90 (m, 4H), 2.07-2.12 (m, 1H), 2.14-2.19 (m, 1H), 2.23-2.30 (m, 1H), 2.51 (s, 2H), 2.66-2.74 (m, 1H), 2.79-2.88 (m, 1H), 2.91-3.00 (m, 1H), 3.07 (t, J=6.0 Hz, 2H), 3.11-3.16 (m, 1H), 3.32-3.36 (m, 1H), 3.91 (s, 3H), 3.93-3.97 (m, 1H), 5.00-5.06 (m, 1H).

Example 38

3-methyl-1-methylaminomethyl-3,4,6,7,8,9-hexahydropyrazolo[3,4-c]isoquinolin-5-one Example 38A methyl-(3-methyl-5-oxo-4,5,6,7,8,9-hexahydro-3H-pyrazolo[3,4-c]isoquinolin-1-ylmethyl)carbamic acid benzyl ester The title compound was prepared according to the procedure as described in EXAMPLE 24B-E, substituting methyl (benzyloxycarbonylmethylamino)acetate for EXAMPLE 24A. MS (DCI/NH$_3$) m/z 381 (M+H)$^+$.

Example 38B 3-methyl-1-methylaminomethyl-3,4,6,7,8,9-hexahydropyrazolo[3,4-c]isoquinolin-5-one A solution of EXAMPLE 38A (160 mg) in trifluoroacetic acid (10 mL) was heated at 60° C. for 18 hours. The mixture was cooled, diluted with acetonitrile and concentrated. The residue was purified by HPLC (Zorbax C-8, 0.1% trifluoroacetic acid/acetonitrile/water) and the trifluoroacetate salt dissolved in methanol and treated with a solution of hydrochloric acid in ether to provide the title compound as the hydrochloride salt (82 mg, 79%). $^1$H NMR (DMSO-d$_6$): ☐ 1.67-1.79 (m, 4H), 2.38-2.45 (m, 2H), 2.66 (t, J=4.3 Hz, 3H), 2.84-2.95 (m, 2H), 3.86 (s, 3H), 4.40-4.44 (m, 2H), 9.06 (br s, 1H), 12.17 (br s, 1H).

Example 39 benzyl[4-(3-methyl-5-oxo-3,4,6,7,8,9-hexahydropyrazolo[3,4-c]isoquinolin-1-yl)benzyl]carbamate The title compound was prepared according to the procedure for Example 24B-E, substituting methyl 4-(benzyloxycarbonylaminomethyl)benzoate for Example 24A. $^1$H NMR (DMSO-d6) ☐ 1.48-1.59 (m, 2H), 1.62-1.74 (m, 2H), 2.36-2.49 (m, 4H), 3.87 (s, 3H), 4.28 (d, J=6.1 Hz, 2H), 5.07 (s, 2H), 7.28-7.34 (m, 3H), 7.35-7.41 (m, 3H), 7.46 (d, J=8.3 Hz, 2H), 7.86 (t, J=6.0 Hz, 1H).

Example 40

1-(4-aminomethylphenyl)-3-methyl-3,4,6,7,8,9-hexahydropyrazolo[3,4-c]isoquinolin-5-one A solution of Example 39 (90 mg, 0.2 mmol) in trifluoroacetic acid (10 mL) was stirred at 50° C. for 4 hours. After cooling, the mixture was concentrated and the residue purified by HPLC (Zorbax, C-18, 250×2.54 column, Mobile phase A 0.1% trifluoroacetic acid in water, B 0.1% trifluoroacetic acid in acetonitrile, 0-100% gradient) to provide 70 mg of the title compound as the trifluoroacetate salt. $^1$H NMR (CD$_3$OD) ☐ 1.53-1.63 (m, 2H), 1.71-1.80 (m, 2H), 2.42-2.54 (m, 4H), 3.92 (s, 3H), 4.21 (s, 2H), 7.52-7.65 (m, 4H).

Example 41

1-(4-dimethylaminomethylphenyl)-3-methyl-3,4,6,7,8,9-hexahydropyrazolo[3,4-c]isoquinolin-5-one The trifluoroacetate salt of the title compound was prepared according to the procedure as described in Example 26, substituting Example 40 for Example 25. $^1$H NMR (CD$_3$OD) ☐ 1.58-1.65 (m, 2H), 1.73-1.81 (m, 2H), 2.49 (q, J=6.4 Hz, 4H), 2.91 (s, 6H), 3.93 (s, 3H), 4.40 (s, 2H), 7.58-7.68 (m, 4H).

Example 42

1-[4-(isopropylamino-methyl)-phenyl]-3-methyl-3,4,6,7,8,9-hexahydropyrazolo[3,4-c]isoquinolin-5-one The trifluoroacetate salt of the title compound was prepared according to the procedure as described in Example 26, substituting Example 40 for Example 25, and substituting acetone for formaldehyde. $^1$H NMR (CD$_3$OD) ☐ 1.43 (d, J=6.8 Hz, 6H), 1.52-1.65 (m, 2H), 1.72-1.82 (m, 2H), 2.41-2.54 (m, 4H), 3.44-3.55 (m, 1H), 3.93 (s, 3H), 4.29 (s, 2H), 7.56-7.67 (m, 4H).

Example 43

1-(4-cyclohexylaminomethylphenyl)-3-methyl-3,4,6,7,8,9-hexahydropyrazolo[3,4-c]isoquinolin-5-one The trifluoroacetate salt of the title compound was prepared according to the procedure as described in Example 26, substituting Example 40 for Example 25 and substituting cyclohexanone for formaldehyde. $^1$H NMR (CD$_3$OD) ☐ 1.20-1.32 (m, 2H), 1.32-1.50 (m, 3H), 1.54-1.64 (m, 2H), 1.70-1.82 (m, 3H), 1.92 (dd, J=9.0, 2.9 Hz, 2H), 2.16-2.27 (m, 2H), 2.39-2.55 (m, 4H), 3.10-3.25 (m, 1H), 3.92 (s, 3H), 4.30 (s, 2H), 7.56-7.66 (m, 4H).

Example 44

1-(4-cyclopentylaminomethylphenyl)-3-methyl-3,4,6,7,8,9-hexahydropyrazolo[3,4-c]isoquinolin-5-one The trifluoroacetate salt of the title compound was prepared according to the procedure for Example 26, substituting Example 40 for Example 25 and substituting cyclopentanone for formaldehyde. $^1$H NMR (CD$_3$OD) ☐ 1.50-1.63 (m, 2H), 1.64-1.80 (m, 6H), 1.81-1.94 (m, 2H), 2.12-2.32 (m, 2H), 2.33-2.61 (m, 4H), 3.52-3.77 (m, 1H), 3.92 (s, 3H), 4.28 (s, 2H), 7.43-7.71 (m, 4H).

Example 45

1,3-dimethyl-4,6,7,8-tetrahydro-3H-2,3,4-triaza-as-indacen-5-one

The title compound was prepared as described in Winters, G; Sala, A; De Paoli, A.; Ferri, V. *Synthesis* 1984, 1052-1054.

Example 46

1-(4-cycloheptylaminomethylphenyl)-3-methyl-3,4,6,7,8,9-hexahydropyrazolo[3,4-c]isoquinolin-5-one The trifluoroacetate salt of the title compound was prepared according to the procedure as described in EXAMPLE 26, substituting EXAMPLE 40 for EXAMPLE 25 and substituting cycloheptanone for formaldehyde. $^1$H NMR (CD$_3$OD) ☐ 1.52-1.59 (m, 4H), 1.61-1.68 (m, 4H), 1.71-1.78 (m, 4H), 1.78-1.90 (m, 2H), 2.10-2.28 (m, 2H), 2.37-2.59 (m, 4H), 3.26-3.43 (m, 1H), 3.92 (s, 3H), 4.30 (s, 2H), 7.45-7.69 (m, 4H).

Example 47

1-[4-(isobutylaminomethyl)phenyl]-3-methyl-3,4,6,7,8,9-hexahydropyrazolo[3,4-c]isoquinolin-5-one The trifluoroacetate salt of the title compound was prepared according to the procedure as described in Example 26, substituting EXAMPLE 40 for EXAMPLE 25 and substituting 2-methylpropionaldehyde for formaldehyde. $^1$H NMR (CD$_3$OD) ☐ 1.05 (d, J=6.7 Hz, 6H), 1.50-1.67 (m, 2H), 1.67-1.85 (m, 2H), 1.95-2.16 (m, 1H), 2.35-2.60 (m, 4H), 2.94 (d, J=7.0 Hz, 2H), 3.93 (s, 3H), 4.29 (s, 2H), 7.44-7.76 (m, 4H).

Example 48

1-4-(cyclobutylaminomethyl)phenyl)-3-methyl-3,4,6,7,8,9-hexahydropyrazolo[3,4-c]isoquinolin-5-one The trifluoroacetate salt of the title compound was prepared according to the procedure as described in Example 26, substituting EXAMPLE 40 for EXAMPLE 25 and substituting cyclobutanone for formaldehyde. $^1$H NMR (CD$_3$OD) □ 1.42-1.66 (m, 2H), 1.69-1.83 (m, 2H), 1.86-2.02 (m, 2H), 2.17-2.30 (m, 2H), 2.28-2.42 (m, 2H), 2.41-2.58 (m, 4H), 3.81-3.90 (m, 1H), 3.92 (s, 3H), 4.17 (s, 2H), 7.34-7.77 (m, 4H).

Example 49

1-{4-[(cyclopropylmethylamino)methyl]phenyl}-3-methyl-3,4,6,7,8,9-hexahydropyrazolo[3,4-c]isoquinolin-5-one The trifluoroacetate salt of the title compound was prepared according to the procedure as described in Example 26, substituting EXAMPLE 40 for EXAMPLE 25 and substituting cyclopropyl aldehyde for formaldehyde. $^1$H NMR (CD$_3$OD) □ 0.26-0.53 (m, 2H), 0.59-0.81 (m, 2H), 1.02-1.24 (m, 1H), 1.49-1.65 (m, 2H), 1.68-1.85 (m, 2H), 2.34-2.59 (m, 4H), 3.00 (d, J=7.3 Hz, 2H), 3.93 (s, 3H), 4.30 (s, 2H), 7.50-7.71 (m, 4H).

Example 50

1-{4-[(biscyclopropylmethylamino)methyl]phenyl}-3-methyl-3,4,6,7,8,9-hexahydropyrazolo[3,4-c]isoquinolin-5-one The trifluoroacetate salt of the title compound was isolated as a side product from the synthesis of EXAMPLE 49. $^1$H NMR (CD$_3$OD) □ 0.20-0.49 (m, 4H), 0.80 (d, J=7.9 Hz, 4H), 1.01-1.26 (m, 2H), 1.52-1.69 (m, 2H), 1.70-1.90 (m, 2H), 2.37-2.61 (m, 4H), 2.88-3.19 (m, 2H), 3.19-3.36 (m, 2H), 3.93 (s, 3H), 4.58 (s, 2H), 7.48-7.81 (m, 4H).

Example 51

3-methyl-1-(4-propylaminomethylphenyl)-3,4,6,7,8,9-hexahydropyrazolo[3,4-c]isoquinolin-5-one The trifluoroacetate salt of the title compound was prepared according to the procedure as described in Example 26, substituting EXAMPLE 40 for EXAMPLE 25 and substituting propionaldehyde for formaldehyde. $^1$H NMR (CD$_3$OD) □ 1.04 (t, J=7.5 Hz, 3H), 1.48-1.65 (m, 2H), 1.66-1.86 (m, 4H), 2.37-2.60 (m, 4H), 2.92-3.16 (m, 2H), 3.92 (s, 3H), 4.28 (s, 2H), 7.39-7.81 (m, 4H).

Example 52

1-dimethylaminomethyl-3-methyl-3,4,6,7,8,9-hexahydropyrazolo[3,4-c]isoquinolin-5-one Using the procedure as described in EXAMPLE 26, substituting EXAMPLE 38 for EXAMPLE 25 provided the trifluoroacetate salt of the title compound. Treatment of the methanol solution of the trifluoroacetate salt with a solution of hydrochloric acid in ether gave the title compound as the hydrochloride salt (30% yield). $^1$H NMR (CD$_3$OD) □ 1.78-1.92 (m, 4H), 2.51 (t, J=6.1 Hz, 2H), 2.92 (t, J=6.0 Hz, 2H), 3.02 (s, 6H), 3.92 (s, 3H), 4.63 (s, 2H).

Example 53

1-[(isopropylmethylamino)methyl]-3-methyl-3,4,6,7,8,9-hexahydropyrazolo[3,4-c]isoquinolin-5-one The trifluoroacetate salt of the title compound was prepared according to the procedure as described in Example 26, substituting EXAMPLE 38 for EXAMPLE 25 and substituting acetone for formaldehyde. Treatment of the methanol solution of the trifluoroacetate salt with a solution of hydrochloric acid in ether gave the title compound as the hydrochloride salt (39% yield). $^1$H NMR (CD$_3$OD) □ 1.45 (dd, J=6.7, 1.8 Hz, 6H), 1.78-1.93 (m, 4H), 2.51 (t, J=6.1 Hz, 2H), 2.91 (s, 3H), 2.93-2.98 (m, 2H), 3.80-3.88 (m, 1H), 3.92 (s, 3H), 4.43 (d, J=14.7 Hz, 1H), 4.74 (d, J=14.7 Hz, 1H).

Example 54

(S)-3-methyl-1-piperidin-2-yl-3,4,6,7,8,9-hexahydropyrazolo[3,4-c]isoquinolin-5-one The trifluoroacetate salt of the title compound was prepared according to the procedures as described in EXAMPLES 24 and 25, substituting (R)-(+)-1-(carboxybenzyl)-2-piperidine carboxylic acid for 1-N-carboxybenzylpyrrolidine-3-carboxylic acid, followed by purification by HPLC (Zorbax, C-18, 250×2.54 column, Mobile phase A: 0.1% trifluoroacetic acid in water; B: 0.1% trifluoroacetic acid in acetonitrile; 0-100% gradient). $^1$H NMR (CD$_3$OD) □ 1.76-1.83 (m, 4H), 1.85 (d, J=6.1 Hz, 2H), 1.87-1.90 (m, 1H), 1.93-2.03 (m, 2H), 2.28 (d, J=13.4 Hz, 1H), 2.44-2.57 (m, 2H), 2.78-2.88 (m, 1H), 2.94-3.05 (m, 1H), 3.16-3.27 (m, 1H), 3.47 (d, J=12.5 Hz, 1H), 3.89 (s, 3H), 4.65 (d, J=8.8 Hz, 1H).

Example 55

3-methyl-1-{4-[(2-methyltetrahydrofuran-3-ylamino)methyl]phenyl}-3,4,6,7,8,9-hexahydropyrazolo[3,4-c]isoquinolin-5-one The trifluoroacetate salt of the title compound was prepared according to the procedure as described in EXAMPLE 26, substituting EXAMPLE 40 for EXAMPLE 25 and substituting 2-methyltetrahydrofuran-3-one for formaldehyde. $^1$H NMR (CD$_3$OD) □ 1.32 (d, J=6.4 Hz, 3H), 1.52-1.63 (m, 2H), 1.69-1.84 (m, 2H), 2.10-2.24 (m, 1H), 2.40-2.57 (m, 4H), 3.55-3.68 (m, 1H), 3.93 (s, 3H), 3.94-4.01 (m, 2H), 4.00-4.14 (m, 1H), 4.18-4.27 (m, 1H), 4.34 (s, 2H), 7.47-7.75 (m, 4H).

Example 56

1-(3-aminomethylphenyl)-3-methyl-3,4,6,7,8,9-hexahydropyrazolo[3,4-c]isoquinolin-5-one

Example 56A methyl 3-[(4-methoxybenzylamino)methyl]benzoate

To a solution of 4-methoxybenzylamine (5.6 g, 41.2 mmol) in methanol (100 mL) was added methyl 3-formylbenzoate (5.2 g, 31.7 mmol) at ambient temperature. The solution was stirred for 30 minutes and sodium cyanoborohydride (3.0 g) was added. The mixture was stirred at ambient temperature overnight and concentrated to about 20 mL. Water (100 mL) was added and the mixture acidified with 2N hydrochloric acid to a pH of 3. The mixture was partitioned between ethyl acetate and brine and the organic phase separated and concentrated. The residue was purified by flash chromatography on silica gel using 10% methanol in ethyl acetate to give 6.0 g (67%) of the title compound. MS (DCI): m/z 286 (M+H)$^+$.

Example 56B methyl 3-{[benzyloxycarbonyl-(4-methoxybenzyl) amino]methyl}benzoate To a mixture of EXAMPLE 56A (6 g, 21 mmol), potassium carbonate (5 g, 36 mmol), dioxane (150 mL) and water (50 mL) was added benzyl chlorofomate (3.4 mL, 23 mmol) at ambient temperature and the mixture stirred overnight. Catalytic piperazine was added and the mixture stirred for another 30 minutes and concentrated. The residue was partitioned between dilute hydrochloric acid and ethyl acetate and the organic phase was washed with water and concentrated. The residue was purified by flash chromatography on silica gel using 20% ethyl acetate in hexane to give 8.2 g (93%) of the title compound. MS (DCI): m/z 420 (M+H)$^+$.

Example 56C benzyl[3-(2-cyanoacetyl)benzyl]-(4-methoxybenzyl) carbamate

A solution of acetonitrile (1.46, 28 mmol) in tetrahydrofuran (180 mL) was treated with n-butyl lithium (1.6 M solution in hexane, 14 mL, 22.2 mmol) at −78° C. for 10 minutes. A solution of EXAMPLE 56B (7.8 g, 18.6 mmol) in 40 mL of tetrahydrofuran was added and the mixture stirred at −78° C. for 1 hour and at ambient temperature for 1 hour. After quenching with water, the mixture was acidified with 2N hydrochloric acid to a pH of 3. The mixture was partitioned between ethyl acetate and brine and the organic phase washed with water and concentrated. The residue was purified by flash chromatography on silica gel using 30% ethyl acetate in hexane to give 7.7 g (96%) of the title compound. MS (DCI): m/z 429 (M+H)$^+$.

Example 56D benzyl[3-(5-amino-1-methyl-1H-pyrazol-3-yl)benzyl]-(4-methoxybenzyl)carbamate To a suspension of EXAMPLE 56C (7.7 g, 18 mmol) in ethanol (60 mL) was added methylhydrazine (1.4 mL, 27 mmol) at ambient temperature and the solution heated to reflux for 4 hours. After cooling, the mixture was concentrated and the residue purified by flash chromatography on silica gel using ethyl acetate to give 4.5 g (56%) of the title compound. MS (DCI): m/z 456 (M+H)$^+$.

Example 56E benzyl[3-(5-amino-4-cyclohex-1-enyl-1-methyl-1H-pyrazol-3-yl)benzyl]-(4-methoxybenzyl)carbamate A solution of EXAMPLE 56D (4.5 g, 10 mmol) in acetic acid (100 mL) was treated with cyclohexanone (2 mL, 20 mmol) at ambient temperature for 4 days. The mixture was concentrated and the residue partitioned between dilute sodium hydroxide and ethyl acetate. The organic layer was washed with water and concentrated and the residue purified by flash chromatography on silica gel using ethyl acetate to give 3.8 g (71%) of the title compound. MS (DCI): m/z 537 (M+H)$^+$.

Example 56F benzyl (4-methoxybenzyl)-[3-(3-methyl-5-oxo-4,5,6,7,8,9-hexahydropyrazolo[3,4-c]isoquinolin-1-yl) benzyl]carbamate To a solution of EXAMPLE 56E (3.8 g, 7.1 mmol) in pyridine (100 mL) was added ethyl isocyanate (1.6 mL, 21 mmol) and the solution stirred at ambient temperature for 24 hours. The mixture was heated at reflux overnight, cooled, concentrated and the residue purified by flash chromatography on silica gel using ethyl acetate to give 3.4 g (85%) of the title compound. MS (DCI): m/z 563 (M+H)$^+$.

Example 56G 1-(3-aminomethylphenyl)-3-methyl-3,4,6,7,8,9-hexahydropyrazolo[3,4-c]isoquinolin-5-one A solution of EXAMPLE 56F (3.4 g) in trifluoroacetic acid (20 mL) was stirred at 55° C. for 6 hours. The mixture was concentrated and the residue purified by HPLC (Zorbax, C-18, 250×2.54 column, Mobile phase A: 0.1% trifluoroacetic acid in water; B: 0.1% trifluoroacetic acid in acetonitrile; 0-100% gradient) to give the title compound (1.3 g, 50%) as the trifluoroacetate salt. $^1$H NMR (CD$_3$OD) □ 2.28-2.40 (m, 2H), 2.44-2.57 (m, 2H), 3.08-3.37 (m, 4H), 4.69 (s, 3H), 4.93 (s, 2H), 8.26-8.37 (m, 3H), 8.43 (s, 1H).

Example 57

1-{3-[(dimethylamino)methyl]phenyl}-3-methyl-3,4,6,7,8,9-hexahydro-5H-pyrazolo[3,4-c]isoquinolin-5-one Example 57A benzyl[3-(3-methyl-5-oxo-3,4,6,7,8,9-hexahydropyrazolo[3,4-c]isoquinolin-1-yl)benzyl]carbamate The title compound was prepared according to the procedure for Example 24B-E, substituting methyl 3-(benzyloxycarbonylaminomethyl)benzoate for Example 24A.

Example 57B 1-(3-aminomethylphenyl)-3-methyl-3,4,6,7,8,9-hexahydropyrazolo[3,4-c]isoquinolin-5-one The trifluoroacetate salt of the title compound was prepared as described in Example 40, substituting Example 57A for Example 39.

Example 57C

1-{3-[(dimethylamino)methyl]phenyl}-3-methyl-3,4,6,7,8,9-hexahydro-5H-pyrazolo[3,4-c]isoquinolin-5-one The trifluoroacetate salt of the title compound was prepared according to the procedure for Example 26, substituting Example 57B for Example 25. MS (DCI): m/z 337 (M+H)+; 1H NMR (400 MHz, CD3OD): δ 1.58-1.64 (m, 2H), 1.74-1.79 (m, 2H), 2.46-2.53 (m, 4H), 2.90 (s, 6H), 3.93 (s, 3H), 4.40 (s, 2H), 7.60-7.62 (m, 2H), 7.65-7.69 (m, 2H); Anal. Calcd for C20H24N4O.1.5 TFA: C, 54.44; H, 5.06; N, 11.04. Found: C, 54.14; H, 4.75; N, 11.01.

Example 58

3-methyl-1-[(2S)-1-propylpiperidin-2-yl]-3,4,6,7,8,9-hexahydro-5H-pyrazolo[3,4-c]isoquinolin-5-one The hydrochloride salt of the title compound was prepared according to procedure as describe in Example 26, substituting Example 54 for Example 25, and substituting propionaldehyde for formaldehyde. The trifluoroacete salt was treated with 1.0 M solution of HCl in ether to yield the HCl salt. MS (DCI/NH3) m/z 329 (M+H)+; 1H NMR (400 MHz, CD3OD): δ 0.86 (t, J=7.36 Hz, 3H), 1.60-1.71 (m, 1H), 1.73-1.79 (m, 2H), 1.79-1.84 (m, J=8.59 Hz, 2H), 1.84-1.90 (m, 2H), 1.90-1.97 (m, 2H), 1.98-2.08 (m, 2H), 2.23-2.33 (m, 1H), 2.49-2.58 (m, 2H), 2.76-2.88 (m, 1H), 2.93-3.07 (m, 3H), 3.18-3.28 (m, 1H), 3.76 (d, J=11.97 Hz, 1H), 3.92 (s, 3H), 4.66 (dd, J=11.66, 2.76 Hz, 1H). Anal. Calcd for C19H28N4O.1.9 HCl: C, 57.38; H, 7.58; N, 14.09. Found: C, 57.08; H, 7.97; N, 13.79.

Example 59

1-azetidin-3-yl-3-methyl-3,4,6,7,8,9-hexahydro-5H-pyrazolo[3,4-c]isoquinolin-5-one The trifluoroacetate salt of the title compound was prepared according to the procedures for Examples 24A-24E and Example 25, substituting N-carbobenzyloxyazetidine-3-carboxylic acid for N-carbobenzyloxypyrrolidine-3-carboxylic acid. MS (DCI): m/z 259 (M+H)+; 1H NMR (400 MHz, DMSO-d6): δ 1.66-1.75 (m, 4H), 2.37-2.41 (m, 2H), 2.70 (br s, 2H), 3.84 (s, 3H), 4.22-4.31 (m, 4H), 4.42 (q, J=8.08 Hz, 1H), 8.94 (br s, 1H), 11.92 (br s, 1H); Anal. Calcd for C14H18N4O.1.32 TFA: C, 48.88; H, 4.76; N, 13.70. Found: C, 48.86; H, 4.53; N, 13.80.

Example 60

1-(1-cyclobutylazetidin-3-yl)-3-methyl-3,4,6,7,8,9-hexahydro-5H-pyrazolo[3,4-c]isoquinolin-5-one The trifluoroacetate salt of the title compound was prepared according to the procedure for Example 26, substituting Example 59 for Example 25, and cyclobutanone for formaldehyde. MS (DCI): m/z 313 (M+H)+; 1H NMR (500 MHz, Pyridine-d5): δ 1.51-1.77 (m, 6H), 2.07-2.14 (m, 2H), 2.30-2.37 (m, 2H), 2.70 (t, J=5.95 Hz, 2H), 2.81 (t, J=5.80 Hz, 2H), 3.91-3.96 (m, 1H), 4.01 (s, 3H), 4.37 (t, J=7.93 Hz, 2H), 4.61-4.66 (m, 1H), 4.71 (t, J=8.85 Hz, 2H); Anal. Calcd for C18H24N4O.1.6 TFA: C, 51.46; H, 5.21; N, 11.32. Found: C, 51.46; H, 5.32; N, 11.28.

Example 61

1-[4-(aminomethyl)benzyl]-3-methyl-3,4,6,7,8,9-hexahydro-5H-pyrazolo[3,4-c]isoquinolin-5-one The trifluoroacetate salt of the title compound was prepared according to the procedure for Examples 24B-24E and Example 25, substituting methyl 4-((benzyloxycarbonylamino)methyl)phenyl)acetate for Example 24A. MS (DCI): m/z 323 (M+H)+; 1H NMR (400 MHz, CD3OD): δ 1.61-1.72 (m, 4H), 2.42 (t, J=5.37 Hz, 2H), 2.65 (t, J=5.98 Hz, 2H), 3.86 (s, 3H), 4.07 (s, 2H), 4.24 (s, 2H), 7.23 (d, J=8.59 Hz, 2H), 7.36 (d, J=8.29 Hz, 2H).

Example 62

3-methyl-1-[(2R)-1-(2-phenylethyl)pyrrolidin-2-yl]-3,4,6,7,8,9-hexahydro-5H-pyrazolo[3,4-c]isoquinolin-5-one The hydrochloride salt of the title compound was prepared according to procedure for Example 26 substituting phenylacetaldehyde for formaldehyde, and substituting Example 102 for Example 25. The trifluoroacetate salt was treated with 1.0 M solution of HCl in ether to yield the HCl salt. MS (DCI/NH3) m/z 377 (M+H)+; 1H NMR (500 MHz, CD3OD): δ 1.75-1.89 (m, 4H), 2.03-2.12 (m, 1H), 2.14-2.22 (m, 1H), 2.24-2.33 (m, 1H), 2.46-2.55 (m, 2H), 2.66-2.74 (m, 1H), 2.77-2.87 (m, 2H), 2.93-3.03 (m, 1H), 3.04-3.12 (m, 1H), 3.34-3.42 (m, 1H), 3.46-3.54 (m, 1H), 3.59-3.68 (m, 1H), 3.91 (s, 3H), 3.92-3.97 (m, 1H), 5.04 (t, J=8.09 Hz, 1H), 7.17-7.20 (m, 2H), 7.21-7.23 (m, 1H), 7.25-7.29 (m, 2H).

Example 63

3-methyl-1-piperidin-3-yl-3,4,6,7,8,9-hexahydro-5H-pyrazolo[3,4-c]isoquinolin-5-one The title compound was prepared according to procedures for Examples 24A-24E and Example 25 substituting 1-benzyl piperidine-1,3-dicarboxylate for 1-benzyl pyrrolidine-1,3-dicarboxylate. The product as TFA salt was treated with 1.0 M solution of HCl in ether to yield the HCl salt. MS (DCI/NH3) m/z 287 (M+H)+; 1H NMR (500 MHz, CD3OD): δ 1.65-1.78 (m, 5H), 1.80-1.88 (m, 2H), 1.98-2.07 (m, 1H), 2.36-2.46 (m, 2H), 2.81-2.97 (m, 3H), 2.99-3.11 (m, 1H), 3.27 (d, J=12.21 Hz, 1H), 3.37 (d, J=11.90 Hz, 1H), 3.52-3.59 (m, 1H), 3.79 (s, 3H). Anal. Calcd for C16H22N4O.2.4HCl: C, 51.40; H, 6.58; N, 14.99. Found: C, 51.69; H, 6.46; N, 14.64.

Example 64

3-methyl-1-piperidin-4-yl-3,4,6,7,8,9-hexahydro-5H-pyrazolo[3,4-c]isoquinolin-5-one The title compound was prepared as trifluoroacetate salt according to procedure for Examples 24A-24E and Example 25 substituting 1-benzyl piperidine-1,4-dicarboxylate for 1-benzyl pyrrolidine-1,3-dicarboxylate. MS (DCI/NH3) m/z 287 (M+H)+; 1H NMR (500 MHz, CD3OD): δ 1.67-1.79 (m, 4H), 1.85-1.95 (m, 2H), 1.97-2.05 (m, 2H), 2.35-2.46 (m, 2H), 2.85-2.94 (m, 2H), 3.06 (q, J=11.60 Hz, 2H), 3.27-3.34 (m, 3H), 3.77 (s, 3H); Anal. Calcd for C16H22N4O.1.0 TFA: C, 54.00; H, 5.79; N, 13.99. Found: C, 53.98; H, 5.61; N, 13.87.

Example 65

1-cyclopropyl-3,7-dimethyl-3,4,6,7,8,9-hexahydro-5H-pyrazolo[3,4-c]isoquinolin-5-one The title compound was prepared according to procedure for Examples 7A-7B substituting 4-methylcyclohexanone for cyclohexanone. Yield: 47%. MS (DCI/NH3) m/z 258 (M+H)+; 1H NMR (500 MHz, DMSO-d6): δ 0.72-0.76 (m, 1H), 0.82-0.87 (m, 3H), 1.04 (d, J=6.41 Hz, 3H), 1.26-1.38 (m, 1H), 1.67-1.78 (m, 1H), 1.82-1.91 (m, 2H), 2.07-2.17 (m, 1H), 2.62 (dd, J=16.48, 3.97 Hz, 1H), 2.88-3.01 (m, 1H), 3.16 (d, J=20.14 Hz, 1H), 3.70 (s, 3H), 11.86 (br s, 1H). Anal. Calcd for $C_{15}H_{19}N_3O$: C, 70.01; H, 7.44; N, 16.33. Found: C, 70.00; H, 7.56; N, 16.36.

Example 66

1-cyclopropyl-3-methyl-3,4,6,7,8,9-hexahydro-5H-pyrazolo[3,4-c]-2,7-naphthyridin-5-one Example 66A benzyl 1-cyclopropyl-3-methyl-5-oxo-4,5,8,9-tetrahydro-3H-pyrazolo[3,4-c][2,7]naphthyridine-7 (6H)-carboxylate The title compound was prepared according to procedure for Examples 7A-7B substituting benzyl-4-oxo-1-piperidine carboxylate for cyclohexanone. MS (DCI/NH$_3$) m/z 379 (M+H)$^+$.

Example 66B 1-cyclopropyl-3-methyl-3,4,6,7,8,9-hexahydro-5H-pyrazolo[3,4-c]-2,7-naphthyridin-5-one A solution of Example 66A (180 mg, 0.48 mmol) in trifluoroacetic acid (5 mL) was heated at 50° C. for 16 h. After cooling, acetonitrile was added and the mixture concentrated on a rotary evaporator. The residue was separated by HPLC (Zorbax C-18, 0.1% TFA/CH$_3$CN/H$_2$O) to provide the title product as trifluoroacetate salt. This product was treated with 1.0 M solution of HCl in ether to yield the HCl salt. Yield: 92 mg (60%). MS (DCI/NH$_3$) m/z 245 (M+H)$^+$; $^1$H NMR (500 MHz, DMSO-d$_6$): δ 0.77-0.85 (m, 2H), 0.86-0.92 (m, 2H), 2.04-2.17 (m, 1H), 3.24-3.32 (m, 2H), 3.33-3.41 (m, 2H), 3.74 (s, 3H), 3.84-3.96 (m, 2H), 5.27 (br s, 1H), 9.64 (br s, 1H). Anal. Calcd for $C_{13}H_{16}N_4O.2.1HCl$: C, 48.91; H, 5.69; N, 17.46. Found: C, 48.91; H, 5.88; N, 17.11.

Example 67

3-ethyl-1-(1-methylpyrrolidin-2-yl)-3,4,6,7,8,9-hexahydro-5H-pyrazolo[3,4-c]isoquinolin-5-one The title compound was prepared as TFA salt according to procedure for Example 69A-69F, substituting (±)-1-benzyl 2-methyl pyrrolidine-1,2-dicarboxylate for (R)-1-benzyl 2-methyl pyrrolidine-1,2-dicarboxylate and ethylhydrazine for (2,2,2-Trifluoro-ethyl)-hydrazine HCl salt. MS (DCI): m/z 301 (M+H)$^+$; $^1$H NMR (400 MHz, CD$_3$OD): δ 1.42 (t, J=7.36 Hz, 2H), 1.75-1.91 (m, 4H), 2.02-2.26 (m, 2H), 2.23-2.37 (m, 1H), 2.52 (t, J=5.68 Hz, 2H), 2.59-2.77 (m, 1H), 2.77-2.89 (m, 1H), 2.88-3.03 (m, 1H), 2.96 (s, 3H), 3.26-3.41 (m, 1H), 3.75-3.93 (m, 1H), 4.30 (q, J=7.36 Hz, 2H), 4.96 (t, J=8.29 Hz, 1H).

Example 68

1-{4-[(dimethylamino)methyl]benzyl}-3-methyl-3,4,6,7,8,9-hexahydro-5H-pyrazolo[3,4-c]isoquinolin-5-one The trifluoroacetate salt of the title compound was prepared according to procedure for Example 26 substituting Example 61 for Example 25. MS (DCI/NH$_3$) m/z 351 (M+H)$^+$; $^1$H NMR (500 MHz, DMSO-d$_6$): δ 1.61 (m, 4H), 2.34-2.37 (m, 2H), 2.61-2.65 (m, 2H), 2.70 (s, 3H), 2.71 (s, 3H), 3.80 (s, 3H), 4.19 (s, 2H), 4.22 (d, J=5.19 Hz, 2H), 7.25 (d, J=8.24 Hz, 2H), 7.39 (d, J=7.93 Hz, 2H), 9.61 (s, 1H). Anal. Calcd for $C_{21}H_{26}N_4O.2$ TFA: C, 51.90; H, 4.88; N, 9.68. Found: C, 51.91; H, 4.20; N, 9.42.

Example 69

1-[(2R)-1-methylpyrrolidin-2-yl]-3-(2,2,2-trifluoro-ethyl)-3,4,6,7,8,9-hexahydro-5H-pyrazolo[3,4-c]isoquinolin-5-one Example 69A (R)-benzyl 2-(2-cyanoacetyl)pyrrolidine-1-carboxylate The title compound was prepared according to procedure for Example 24B, substituting (R)-1-benzyl 2-methyl pyrrolidine-1,2-dicarboxylate for EXAMPLE 24A. MS(DCI): m/z 273 (M+1)$^+$.

Example 69B (R)-2-[5-Amino-1-(2,2,2-trifluoro-ethyl)-1H-pyrazol-3-yl]-pyrrolidine-1-carboxylic acid benzyl ester To a solution of Example 69A (3.0 g, 11 mmol) in ethanol (10 mL) was added (2,2,2-Trifluoro-ethyl)-hydrazine HCl salt (2.3 g, 11 mmol) and triethylamine (1.84 mL, 13.2 mmol) at rt. The solution was heated under reflux for 4 h. After cooling, the reaction mixture was concentrated and the residue was separated by flash chromatography to give Example 69B. Yield: 3.5 g (88%). MS (DCI): m/z 369 (M+H)$^+$.

Example 69C (R)-2-[5-Amino-4-cyclohex-1-enyl-1-(2,2,2-trifluoro-ethyl)-1H-pyrazol-3-yl]-pyrrolidine-1-carboxylic acid benzyl ester The title compound was prepared according to the procedure for Example 24D, substituting Example 69B for Example 24C. Yield: 50%. MS (DCI): m/z 449 (M+H)$^+$.

Example 69D benzyl (2R)-2-[5-oxo-3-(2,2,2-trifluoroethyl)-4,5,6,7,8,9-hexahydro-3H-pyrazolo[3,4-c]isoquinolin-1-yl]pyrrolidine-1-carboxylate The title compound was prepared according to the procedure for 24E, substituting Example 69D for Example 24D. Yield: 33%. MS (DCI): m/z 475 (M+H)$^+$.

Example 69E

1-[(2R)-pyrrolidin-2-yl]-3-(2,2,2-trifluoroethyl)-3,4,6,7,8,9-hexahydro-5H-pyrazolo[3,4-c]isoquinolin-5-one A solution of Example 69D (0.55 g, 1.16 mmol) in TFA (10 ml) was heated at 50° C. for 6 h. Volatile were removed and the residual was purified by HPLC (C-18, 0-100% gradient CH₃CN with 0.1% TFA in water with 0.1% TFA) to provide Example 69E. MS (DCI): m/z 341 (M+H)⁺.

Example 69F

1-[(2R)-1-methylpyrrolidin-2-yl]-3-(2,2,2-trifluoro-ethyl)-3,4,6,7,8,9-hexahydro-5H-pyrazolo[3,4-c]isoquinolin-5-one The title compound was prepared as TFA salt according to the procedure for Example 26, substituting Example 69E for 25. MS (DCI): m/z 355 (M+H)⁺; ¹H NMR (500 MHz, CD₃OD) δ 1.74-1.98 (m, 5H), 2.04-2.26 (m, 2H), 2.26-2.39 (m, 1H), 2.53-2.67 (m, 2H), 2.71-2.81 (m, 1H), 2.82-2.95 (m, 1H), 2.98 (s, 2H), 3.00-3.09 (m, 1H), 3.30-3.43 (m, 1H), 3.67-3.94 (m, 1H), 4.95-5.21 (m, 3H).

Example 70

3-methyl-1-(1-methylpiperidin-3-yl)-3,4,6,7,8,9-hexahydro-5H-pyrazolo[3,4-c]isoquinolin-5-one The title compound was prepared according to procedure for Example 26 substituting Example 63 for Example 25. The product was treated with 1.0 M solution of HCl in ether to yield the HCl salt. Yield: 31%. MS (DCI/NH₃) m/z 301 (M+H)⁺; ¹H NMR (500 MHz, pyridine-d₅): δ 1.65-1.75 (m, 4H), 1.77-1.84 (m, 1H), 1.85-1.93 (m, 1H), 2.24-2.32 (m, 1H), 2.58-2.68 (m, 1H), 2.78-2.83 (m, 3H), 2.84 (s, 3H), 3.08-3.15 (m, 1H), 3.29-3.42 (m, 2H), 3.47-3.57 (m, 1H), 3.82-3.91 (m, 1H), 3.97 (s, 3H), 4.38-4.47 (m, 1H), 5.40 (br s, 1H). Anal. Calcd for C₁₇H₂₄N₄O.2.1 HCl: C, 54.17; H, 6.98; N, 14.86. Found: C, 54.37; H, 6.95; N, 14.56.

Example 71

2-{1-[(2R)-1-methylpyrrolidin-2-yl]-5-oxo-4,5,6,7,8,9-hexahydro-3H-pyrazolo[3,4-c]isoquinolin-3-yl}ethyl ethylcarbamate The title compound was prepared according to the procedure for Example 69A-69F, substituting 2-hydrazino-ethanol for (2,2,2-Trifluoro-ethyl)-hydrazine HCl salt. MS (DCI): m/z 388 (M+H)⁺; ¹H NMR (500 MHz, CD₃OD) δ 0.94 (t, J=7.17 Hz, 3H), 1.62-1.96 (m, 4H), 2.06-2.24 (m, 2H), 2.25-2.35 (m, 1H), 2.51 (s, 3H), 2.69-2.75 (m, 1H), 2.77-2.86 (m, 1H), 2.89-3.09 (m, 4H), 3.32-3.43 (m, 2H), 3.62-3.92 (m, 1H), 4.31-4.43 (m, 1H), 4.42-4.63 (m, 3H), 4.96 (t, J=8.39 Hz, 1H).

Example 72

3-{5-oxo-1-[(2R)-pyrrolidin-2-yl]-4,5,6,7,8,9-hexahydro-3H-pyrazolo[3,4-c]isoquinolin-3-yl}propanamide

Example 72A benzyl (2R)-2-[3-(2-cyanoethyl)-5-oxo-4,5,6,7,8,9-hexahydro-3H-pyrazolo[3,4-c]isoquinolin-1-yl]pyrrolidine-1-carboxylate The title compound was prepared according to the procedure for Example 69D, substituting 3-hydrazino-propionitrile for (2,2,2-Trifluoro-ethyl)-hydrazine HCl salt. MS (DCI): m/z 446 (M+H)⁺;

Example 72B

3-{5-oxo-1-[(2R)-pyrrolidin-2-yl]-4,5,6,7,8,9-hexahydro-3H-pyrazolo[3,4-c]isoquinolin-3-yl}propanamide The title compound was prepared as TFA salt according to the procedure for Example 69E, substituting Example 72A for Example 69D. MS (DCI): m/z 330 (M+H)⁺. ¹H NMR (500 MHz, CD₃OD) δ 1.72-1.94 (m, 4H), 2.07-2.32 (m, 3H), 2.42-2.58 (m, 3H), 2.79 (t, J=6.41 Hz, 2H), 2.83-3.00 (m, 2H), 3.37-3.50 (m, 1H), 3.48-3.65 (m, 1H), 4.42-4.55 (m, 2H), 5.11-5.22 (m, 1H).

Example 73

3-methyl-1-(1-methylpiperidin-4-yl)-3,4,6,7,8,9-hexahydro-5H-pyrazolo[3,4-c]isoquinolin-5-one The title compound was prepared according to procedure for Example 26 substituting Example 64 for Example 25. The product was treated with 1.0 M solution of HCl in ether to yield the HCl salt. Yield: 59%. MS (DCI/NH₃) m/z 301 (M+H)⁺; ¹H NMR (500 MHz, CD₃OD): δ 1.77-1.88 (m, 5H), 2.07-2.18 (m, 2H), 2.19-2.25 (m, 2H), 2.50 (t, J=5.95 Hz, 2H), 2.92 (s, 3H), 2.96-3.02 (m, 2H), 3.15-3.24 (m, 2H), 3.57-3.65 (m, 2H), 3.83 (s, 3H). Anal. Calcd for C₁₇H₂₄N₄O.2.1 HCl: C, 54.18; H, 6.98; N, 14.86. Found: C, 54.11; H, 7.09; N, 14.70.

Example 74

3-{1-[(2R)-1-methylpyrrolidin-2-yl]-5-oxo-4,5,6,7,8,9-hexahydro-3H-pyrazolo[3,4-c]isoquinolin-3-yl}propanenitrile

Example 74A

3-{5-oxo-1-[(2R)-pyrrolidin-2-yl]-4,5,6,7,8,9-hexahydro-3H-pyrazolo[3,4-c]isoquinolin-3-yl}propanenitrile The title compound was prepared according to the procedure for Example 69E, substituting Example 72A for Example 69D. MS (DCI): m/z 326 (M+H)⁺.

Example 74B

3-{1-[(2R)-1-methylpyrrolidin-2-yl]-5-oxo-4,5,6,7,8,9-hexahydro-3H-pyrazolo[3,4-c]isoquinolin-3-yl}propanenitrile The title compound was prepared according to the procedure for Example 26, substituting Example 74A for Example 25. MS (DCI): m/z 326 (M+H)⁺; ¹H NMR (400 MHz, CD₃OD) δ 1.86 (d, J=5.52 Hz, 3H), 2.04-2.42 (m, 4H), 2.56 (s, 3H), 2.74 (s, 1H), 2.89 (s, 1H), 2.99 (s, 3H), 3.07 (t, J=6.29 Hz, 2H), 3.31-3.47 (m, 1H), 3.60-3.97 (m, 1H), 4.32-4.74 (m, 2H), 5.01 (t, J=7.98 Hz, 1H).

Example 75

3-[2-(dimethylamino)benzyl]-1-[(2R)-pyrrolidin-2-yl]-3,4,6,7,8,9-hexahydro-5H-pyrazolo[3,4-c]isoquinolin-5-one The title compound was prepared according to the procedures for Examples 69B-69E, substituting (2-hydrazino-phenyl)-dimethyl-amine for (2,2,2-Trifluoro-ethyl)-hydrazine HCl salt. MS (DCI): m/z 392 (M+H)+; $^1$H NMR (400 MHz, CD$_3$OD) δ 1.54-2.00 (m, 4H), 2.07-2.32 (m, 3H), 2.44-2.67 (m, 3H), 2.95 (t, J=5.98 Hz, 2H), 3.01 (s, 6H), 3.35-3.47 (m, 1H), 3.46-3.62 (m, 1H), 5.18 (t, J=7.36 Hz, 1H), 5.59 (s, 2H), 7.04-7.21 (m, 2H), 7.34-7.44 (m, 1H), 7.47-7.50 (m, 1H).

Example 76

1-[(2R)-1-cyclobutylpyrrolidin-2-yl]-3-(3-hydroxybenzyl)-3,4,6,7,8,9-hexahydro-5H-pyrazolo[3,4-c]isoquinolin-5-one

Example 76A 3-(3-hydroxybenzyl)-1-[(2R)-pyrrolidin-2-yl]-3,4,6,7,8,9-hexahydro-5H-pyrazolo[3,4-c]isoquinolin-5-one The title compound was prepared according to the procedure for Example 69E, substituting 3-hydroxybenzylhydrazine for (2,2,2-Trifluoro-ethyl)-hydrazine HCl salt. MS (DCI): m/z 365 (M+H)+;

Example 76B

1-[(2R)-1-cyclobutylpyrrolidin-2-yl]-3-(3-hydroxybenzyl)-3,4,6,7,8,9-hexahydro-5H-pyrazolo[3,4-c]isoquinolin-5-one The title compound was prepared as TFA salt according to the procedure for Example 26, substituting Example 76A for Example 25, and cyclobutanone for formaldehyde. MS (DCI): m/z 419 (M+H)+; $^1$H NMR (400 MHz, CD$_3$OD) δ 1.55-1.77 (m, 3H), 1.76-2.01 (m, 5H), 2.08-2.38 (m, 5H), 2.54 (t, J=5.68 Hz, 2H), 2.58-2.75 (m, 1H), 2.77-3.03 (m, 2H), 3.12-3.28 (m, 1H), 3.63-3.77 (m, 1H), 3.80-4.01 (m, 1H), 4.93 (t, J=7.67 Hz, 1H), 5.29-5.43 (m, 1H), 5.44-5.61 (m, 1H), 6.56 (s, 1H), 6.59-6.78 (m, 2H), 7.11 (t, J=7.82 Hz, 1H).

Example 77

3-[3-(dimethylamino)propyl]-1-pyrrolidin-2-yl-3,4,6,7,8,9-hexahydro-5H-pyrazolo[3,4-c]isoquinolin-5-one

Example 77A benzyl (2R)-2-[5-oxo-3-(3-oxopropyl)-4,5,6,7,8,9-hexahydro-3H-pyrazolo[3,4-c]isoquinolin-1-yl]pyrrolidine-1-carboxylate A solution of Example 72A (2.0 g, 4.5 mmol) in acetic acid (10 ml) was treated with Raney nickel (200 mg) at rt. The reaction mixture was stirred under hydrogen for 6 h. Solid material was filtered off and the filtrate was concentrated. The residue was separated by flash chromatography to give Example 77A. Yield: 0.5 g (25%). MS (DCI): m/z 449 (M+H)+.

Example 77B benzyl (2R)-2-{3-[3-(dimethylamino)propyl]-5-oxo-4,5,6,7,8,9-hexahydro-3H-pyrazolo[3,4-c]isoquinolin-1-yl}pyrrolidine-1-carboxylate The title compound was prepared according to the procedure for Example 26, substituting Example 77A for formaldehyde, and dimethyl amine for Example 25. MS (DCI): m/z 4 480 (M+H)+.

Example 77C

3-[3-(dimethylamino)propyl]-1-pyrrolidin-2-yl-3,4,6,7,8,9-hexahydro-5H-pyrazolo[3,4-c]isoquinolin-5-one The title compound was prepared as TFA salt according to the procedure for Example 69E, substituting Example 77B for Example 69D. MS (DCI): m/z 344 (M+H)+; $^1$H NMR (500 MHz, CD$_3$OD) δ 1.73-1.94 (m, 5H), 2.07-2.36 (m, 6H), 2.44-2.67 (m, 3H), 2.87 (s, 6H), 2.91-3.07 (m, 1H), 3.06-3.24 (m, 2H), 3.39-3.51 (m, 1H), 3.52-3.62 (m, 1H), 5.21 (t, J=7.17 Hz, 2H).

Example 78

1-cyclobutyl-3-[3-(ethylamino)propyl]-3,4,6,7,8,9-hexahydro-5H-pyrazolo[3,4-c]isoquinolin-5-one

Example 78A 3-(1-cyclobutyl-5-oxo-4,5,6,7,8,9-hexahydro-3H-pyrazolo[3,4-c]isoquinolin-3-yl)propanenitrile The title compound was prepared according to the procedure for Example 85B-85D, substituting 3-hydrazino-propionitrile for Example 85A. MS (DCI): m/z 299 (M+H)+;

Example 78B 3-(1-cyclobutyl-5-oxo-4,5,6,7,8,9-hexahydro-3H-pyrazolo[3,4-c]isoquinolin-3-yl)propanal The title compound was prepared according to the procedure for Example 77A, substituting Example 78A for Example 72A. MS (DCI): m/z 4 300 (M+H)+.

Example 78C 1-cyclobutyl-3-[3-(ethylamino)propyl]-3,4,6,7,8,9-hexahydro-5H-pyrazolo[3,4-c]isoquinolin-5-one The title compound was prepared as TFA salt according to the procedure for Example 26, substituting Example 78B for formaldehyde and ethylamine for Example 25. MS (DCI): m/z 329 (M+H)+; $^1$H NMR (500 MHz, DMSO-d$_6$) δ 1.15 (t, J=7.32 Hz, 3H), 1.56-1.80 (m, 3H), 1.77-1.90 (m, 1H), 1.92-2.08 (m, 4H), 2.22-2.32 (m, 4H), 2.33-2.41 (m, 2H), 2.79 (s, 2H), 2.83-3.07 (m, 4H), 3.54-3.91 (m, 2H), 4.25 (t, J=6.71 Hz, 1H), 8.41 (s, 2H).

Example 79

1-cyclobutyl-3-(3-pyrrolidin-1-ylpropyl)-3,4,6,7,8,9-hexahydro-5H-pyrazolo[3,4-c]isoquinolin-5-one The title compound was prepared as TFA salt according to the procedure for Example 26, substituting Example 78B for formaldehyde and pyrrolidine for Example 25. MS (DCI): m/z 355 (M+H)+; 1H NMR (500 MHz, DMSO-$d_6$) δ 1.60-1.77 (m, 4H), 1.77-1.89 (m, 2H), 1.92-2.03 (m, 3H), 2.05-2.16 (m, 2H), 2.16-2.40 (m, 6H), 2.79 (s, 2H), 2.86-3.03 (m, 2H), 3.04-3.21 (m, 2H), 3.55 (dd, J=10.37, 5.19 Hz, 3H), 3.67-3.95 (m, 2H), 4.23 (t, J=6.71 Hz, 1H), 9.64 (s, 1H).

Example 80

1-cyclobutyl-3-[3-(dimethylamino)propyl]-3,4,6,7,8,9-hexahydro-5H-pyrazolo[3,4-c]isoquinolin-5-one The title compound was prepared as TFA salt according to the procedure for Example 26, substituting Example 78B for formaldehyde and dimethyl amine for Example 25. MS (DCI): m/z 329 (M+H)+; 1H NMR (500 MHz, DMSO-$d_6$) δ 1.52-1.78 (m, 3H), 1.78-1.88 (m, 1H), 1.91-2.06 (m, 1H), 2.05-2.18 (m, 2H), 2.21-2.35 (m, 4H), 2.37 (s, 2H), 2.72 (d, J=4.88 Hz, 6H), 2.79 (s, 2H), 2.90-3.12 (m, 2H), 3.71-3.91 (m, 2H), 4.24 (t, J=6.87 Hz, 2H), 10.63 (s, 1H).

Example 81

3-(1-cyclobutyl-5-oxo-4,5,6,7,8,9-hexahydro-3H-pyrazolo[3,4-c]isoquinolin-3-yl)propanoic acid A suspension of Example 78A (100 mg, 0.34 mmol) in 6N HCl (20 ml) was heated at 100° C. for 20 h. After cooling to room temperature the formed solid was collected by filtration, washed with water and MeOH to give Example 81 (100 mg, 90%). MS (DCI): m/z 318 (M+H)+; 1H NMR (500 MHz, DMSO-$d_6$) δ 1.60-1.77 (m, 5H), 1.76-1.91 (m, 1H), 1.90-2.08 (m, 1H), 2.16-2.31 (m, 4H), 2.30-2.43 (m, 2H), 2.65-2.86 (m, 5H), 3.77 (t, J=8.31 Hz, 1H), 4.36 (t, J=6.95 Hz, 2H), 12.00 (s, 2H).

Example 82

3-isopropyl-1-(1-methylpyrrolidin-2-yl)-3,4,6,7,8,9-hexahydro-5H-pyrazolo[3,4-c]isoquinolin-5-one The title compound was prepared as TFA salt according to procedure for Example 69A-69F, substituting (±)-1-benzyl 2-methyl pyrrolidine-1,2-dicarboxylate for (R)-1-benzyl 2-methyl pyrrolidine-1,2-dicarboxylate and isopropylhydrazine for (2,2,2-Trifluoro-ethyl)-hydrazine HCl salt. MS (DCI): m/z 315 (M+H)+; 1H NMR (500 MHz, CD$_3$OD): δ 1.51 (dd, J=6.71, 3.66 Hz, 6H), 1.71-1.95 (m, 3H), 2.05-2.25 (m, 2H), 2.24-2.37 (m, 1H), 2.41-2.56 (m, 2H), 2.69-2.78 (m, 1H), 2.77-2.89 (m, 1H), 2.90-3.03 (m, 1H), 2.96 (s, 3H), 3.29-3.44 (m, 2H), 3.77-3.96 (m, 1H), 4.73-4.91 (m, 2H).

Example 83

4-[(1-cyclobutyl-5-oxo-4,5,6,7,8,9-hexahydro-3H-pyrazolo[3,4-c]isoquinolin-3-yl)methyl]benzonitrile The title compound was prepared according to procedure for Example 85A-85D substituting 4-cyanobenzaldehyde for pyridine-3-aldehyde. MS (DCI/NH$_3$) m/z 359 (M+H)+; 1H NMR (500 MHz, CDCl$_3$): δ 1.56-1.59 (m, 1H), 1.76-1.84 (m, 2H), 1.91-1.98 (m, 1H), 2.03-2.10 (m, 1H), 2.32-2.39 (m, 2H), 2.41-2.50 (m, 5H), 2.86 (t, J=5.34 Hz, 2H), 3.77-3.82 (m, 1H), 5.61 (s, 2H), 7.51 (d, J=8.8 Hz, 2H), 7.56 (d, J=8.8 Hz, 2H), 14.20 (br s, 1H).

Example 84

1-cyclobutyl-3-{4-[(isopropylamino)methyl]benzyl}-3,4,6,7,8,9-hexahydro-5H-pyrazolo[3,4-c]isoquinolin-5-one

Example 84A

4-[(1-cyclobutyl-5-oxo-4,5,6,7,8,9-hexahydro-3H-pyrazolo[3,4-c]isoquinolin-3-yl)methyl]benzaldehyde The title compound was prepared according to procedure for Example 77A, substituting Example 83 for Example 72A. MS (DCI): m/z 362 (M+H)+.

Example 84B 1-cyclobutyl-3-{4-[(isopropylamino)methyl]benzyl}-3,4,6,7,8,9-hexahydro-5H-pyrazolo[3,4-c]isoquinolin-5-one The title compound was prepared as TFA salt according to procedure for Example 26, substituting Example 84A for formaldehyde and isopropyl amine for Example 25. MS (DCI): m/z 405 (M+H)+; 1H NMR (500 MHz, DMSO-$d_6$): δ 1.35 (d, J=6.71 Hz, 6H), 1.55-1.82 (m, 3H), 1.90 (s, 1H), 1.95-2.15 (m, 1H), 2.17-2.51 (m, 6H), 2.50-2.67 (m, 2H), 2.68-2.88 (m, 1H), 3.27 (d, J=5.80 Hz, 1H), 3.71-3.85 (m, 1H), 4.04 (s, 2H), 5.46 (s, 2H), 7.23 (d, J=8.24 Hz, 2H), 7.43 (d, J=8.24 Hz, 2H), 9.54 (s, 2H).

Example 85

1-cyclobutyl-3-(pyridin-3-ylmethyl)-3,4,6,7,8,9-hexahydro-5H-pyrazolo[3,4-c]isoquinolin-5-one

Example 85A

Pyridin-3-ylmethyl-hydrazine

To a solution of pyridine-3-aldehyde (5 g, 46.7 mmol) in methanol (100 mL) was added hydrazine (1.05 mL, 46.7 mmol). The reaction mixture was stirred at rt for 1 h. After purging with nitrogen, 10% Pd/C (200 mg) was added. The reaction mixture was purged with hydrogen and stirred under hydrogen at rt overnight. Solid material was removed, and the filtrate was concentrated to give a crude Example 85A. This material was used without further purification. Yield: 5.2 g (91%). MS (DCI): m/z 124 (M+H)+.

Example 85B

5-Cyclobutyl-2-pyridin-3-ylmethyl-2H-pyrazol-3-ylamine

To a solution of 3-cyclobutyl-3-oxo-propionitrile (3.3 g, 32 mmol) in ethanol (100 mL) was added Example 85A (3.9 g, 32 mmol) at rt. The solution was heated under reflux for 4 h. After cooling, the reaction mixture was concentrated and the residue was separated by flash chromatography (silica gel,

Example 85C

5-Cyclobutyl-4-cyclohex-1-enyl-2-pyridin-3-ylmethyl-2H-pyrazol-3-ylamine

To a solution of Example 85B (4 g, 17.5 mmol) in acetic acid (150 mL) was added cyclohexanone (3 mL). The solution was stirred at 50° C. for 24 h. After cooling, the reaction mixture was concentrated. The residual oil was partitioned between sodium bicarbonate solution and ethyl acetate. The organic phase was washed with water and concentrated. The residue was purified by flash column chromatography to give Example 85C. Yield: 3.2 g (59%). MS (DCI): m/z 309 (M+H)$^+$.

Example 85D 1-cyclobutyl-3-(pyridin-3-ylmethyl)-3,4,6,7,8,9-hexahydro-5H-pyrazolo[3,4-c]isoquinolin-5-one To a solution of Example 85C (4 g, 18 mmol) in anhydrous pyridine (50 mL) was added ethyl isocyanate (3 mL) under nitrogen. The solution was heated at 50° C. for 6 h and under reflux overnight. The volatile were removed and the residual solid was purified by flash chromatography to give Example 85D. Yield: 4.2 g (70%). MS (DCI): m/z 335 (M+H)$^+$, $^1$H NMR (300 MHz, CDCl$_3$) δ 1.58 (s, 1H), 1.72-1.86 (m, 5H), 1.87-2.17 (m, 2H), 2.27-2.61 (m, 6H), 2.84 (s, 2H), 3.62-3.90 (m, 1H), 7.20 (dd, J=7.80, 4.75 Hz, 1H), 7.78 (d, J=7.80 Hz, 1H), 8.48 (d, J=3.05 Hz, 1H), 8.77 (s, 1H).

Example 86

1-cyclobutyl-3-(piperidin-3-ylmethyl)-3,4,6,7,8,9-hexahydro-5H-pyrazolo[3,4-c]isoquinolin-5-one Example 85D was hydrogenated in the presence of 10% palladium on carbon overnight to provide Example 86 (1.8 g). Yield: 56%. MS (DCI): m/z 341 (M+H)$^+$. $^1$H NMR (500 MHz, DMSO-d$_6$) δ 0.92-1.28 (m, 1H), 1.49-1.62 (m, 1H), 1.62-1.76 (m, 7H), 1.74-1.91 (m, 1H), 1.91-2.08 (m, 1H), 2.12-2.44 (m, 6H), 2.57-2.89 (m, 4H), 3.01 (d, J=11.60 Hz, 1H), 3.10-3.29 (m, 1H), 3.71-3.84 (m, 1H), 3.98-4.22 (m, 2H).

Example 87

1-cyclobutyl-3-{3-[(dimethylamino)methyl]benzyl}-3,4,6,7,8,9-hexahydro-5H-pyrazolo[3,4-c]isoquinolin-5-one

Example 87A

3-[(1-cyclobutyl-5-oxo-4,5,6,7,8,9-hexahydro-3H-pyrazolo[3,4-c]isoquinolin-3-yl)methyl]benzonitrile The title compound was prepared according to procedure for Example 85B-85D, substituting 3-hydrazinomethyl-benzonitrile for Example 85A. MS (DCI): m/z 359 (M+H)$^+$.

Example 87B

3-[(1-cyclobutyl-5-oxo-4,5,6,7,8,9-hexahydro-3H-pyrazolo[3,4-c]isoquinolin-3-yl)methyl]benzaldehyde The title compound was prepared according to procedure for Example 77A, substituting Example 87A for Example 72A. MS (DCI): m/z 362 (M+H)$^+$.

Example 87C 1-cyclobutyl-3-{3-[(dimethylamino)methyl]benzyl}-3,4,6,7,8,9-hexahydro-5H-pyrazolo[3,4-c]isoquinolin-5-one The title compound was prepared as TFA salt according to procedure for Example 26, substituting Example 87B for formaldehyde and dimethylamine for Example 25. MS (DCI): m/z 391 (M+H)$^+$; $^1$H NMR (500 MHz, CD$_3$OD): δ 1.72-1.85 (m, 5H), 1.84-2.00 (m, 1H), 1.96-2.18 (m, 1H), 2.28-2.41 (m, 4H), 2.48 (t, J=5.34 Hz, 2H), 2.81 (s, 6H), 2.91 (t, J=5.19 Hz, 2H), 3.88 (t, J=8.54 Hz, 1H), 4.27 (s, 2H), 5.49 (s, 2H), 7.11-7.31 (m, 1H), 7.38-7.43 (m, 1H), 7.46 (t, J=7.48 Hz, 1H).

Example 88

1-cyclobutyl-3-[3-(hydroxymethyl)benzyl]-3,4,6,7,8,9-hexahydro-5H-pyrazolo[3,4-c]isoquinolin-5-one A solution of Example 87B (50 mg, 0.14 mmol) in methylene chloride (10 ml) was treat with sodium borohydride (20 mg, 0.58 mmol) at rt for 1 h. Volatiles were removed and the residual solid was purified by HPLC (C-18, 0-100% gradient CH$_3$CN with 0.1% TFA in water with 0.1% TFA) to give Example 88 as TFA salt. Yield: 36 mg (72%). MS (DCI): m/z 364 (M+H)$^+$; $^1$H NMR (500 MHz, DMSO-d$_6$): δ 1.71 (d, J=4.27 Hz, 5H), 1.74-1.88 (m, 1H), 1.87-2.08 (m, 1H), 2.16-2.33 (m, 4H), 2.39 (s, 1H), 2.43-2.56 (m, 2H), 2.82 (s, 2H), 3.64-3.90 (m, 1H), 3.99 (s, 2H), 5.40-5.45 (m, 2H), 7.11 (d, J=7.02 Hz, 1H), 7.25 (s, 1H), 7.29-7.53 (m, 2H), 8.17 (s, 2H).

Example 89

1-cyclobutyl-3-[(1-methylpiperidin-3-yl)methyl]-3,4,6,7,8,9-hexahydro-5H-pyrazolo[3,4-c]isoquinolin-5-one The title compound was prepared as TFA salt according to the procedure for Example 26, substituting Example 86 for 25. MS (DCI): m/z 355 (M+H)$^+$; $^1$H NMR (400 MHz, CD$_3$OD) δ 1.15-1.41 (m, 1H), 1.59-1.84 (m, 6H), 1.85-1.96 (m, 1H), 1.96-2.20 (m, 2H), 2.24-2.59 (m, 7H), 2.80-2.85 (m, 3H), 2.86-2.98 (m, 4H), 3.31-3.41 (m, 1H), 3.48 (d, J=12.58 Hz, 1H), 3.77-3.95 (m, 1H), 4.08-4.29 (m, 2H).

Example 90 ethyl (1-cyclobutyl-5-oxo-4,5,6,7,8,9-hexahydro-3H-pyrazolo[3,4-c]isoquinolin-3-yl)acetate The title compound was prepared according to procedure for Example 85B-85D, substituting hydrazino-acetic acid ethyl ester for Example 85A. MS (DCI): m/z 330 (M+H)$^+$; $^1$H NMR (400 MHz, CD$_3$OD): δ 1.27 (t, J=7.06 Hz, 3H), 1.70-1.85 (m, 4H), 1.85-1.97 (m, 1H), 1.96-2.20 (m, 1H), 2.27-

2.45 (m, 4H), 2.48 (t, J=4.91 Hz, 2H), 2.90 (t, J=4.91 Hz, 2H), 3.69-3.94 (m, 1H), 4.22 (q, J=7.06 Hz, 2H), 5.02 (s, 2H).

Example 91

1-cyclobutyl-3-(2-hydroxyethyl)-3,4,6,7,8,9-hexahydro-5H-pyrrolo[2,3-c]isoquinolin-5-one A solution of Example 90 (100 mg, 0.3 mmol) in methalene chloride (10 ml) was treat with sodium borohydride (20 mg, 0.58 mmol) at rt for 1 h. Volatiles were removed, and the residual solid was washed with methanol and dried to give Example 91 (40 mg, 47%). MS (DCI): m/z 288 (M+H)$^+$; $^1$H NMR (500 MHz, DMSO-d$_6$): δ 1.65-1.76 (m, 4H), 1.76-1.88 (m, 1H), 1.90-2.05 (m, 1H), 2.17-2.30 (m, 3H), 2.32-2.43 (m, 2H), 2.78 (s, 2H), 3.70 (d, J=4.58 Hz, 2H), 3.73-3.88 (m, 1H), 4.15-4.26 (m, 2H), 4.62-4.85 (m, 1H), 11.67 (s, 2H).

Example 92

(1-cyclobutyl-5-oxo-4,5,6,7,8,9-hexahydro-3H-pyrazolo[3,4-c]isoquinolin-3-yl)acetic acid A solution of Example 90 (100 mg, 0.3 mmol) in a mixture of THF (5 ml) and methanol (5 ml) was treated with a 1N solution of lithium hydroxide (2 mL) at rt for 10 h. The mixture was neutralized with 1N HCl to a pH of 7. The formed solid was collected by filtration, washed with methanol and dried to give Example 92 (30 mg, 32%). MS (DCI): m/z 302 (M+H)$^+$; $^1$H NMR (500 MHz, DMSO-d$_6$): δ 1.65-1.76 (m, 5H), 1.75-1.88 (m, 1H), 1.87-2.06 (m, 1H), 2.18-2.34 (m, 4H), 2.33-2.45 (m, 1H), 2.80 (s, 2H), 3.70-3.87 (m, 1H), 4.93 (s, 2H).

Example 93

1-cyclobutyl-3-[2-(1H-tetrazol-5-yl)ethyl]-3,4,6,7,8,9-hexahydro-5H-pyrazolo[3,4-c]isoquinolin-5-one To a suspension of Example 78A (150 mg, 0.5 mmol) and trimethylsily azide (582 mg, 5.0 mmol) in toluene (20 ml) was added dibutyltin oxide (28 mg, 0.34 mmol). The reaction mixture was heated at 100° C. for 3 days. Volatiles were removed, and the residual solid was washed with methanol and dried to give Example 93 (100 mg, 60%). MS (DCI): m/z 340 (M+H)$^+$; $^1$H NMR (500 MHz, CD$_3$OD): δ 1.70-1.85 (m, 4H), 1.82-1.95 (m, 1H), 1.94-2.13 (m, 1H), 2.24-2.38 (m, 4H), 2.48 (t, J=5.03 Hz, 2H), 2.72-2.90 (m, 2H), 3.48 (q, J=6.92 Hz, 2H), 3.69-3.89 (m, 1H), 4.63 (t, J=6.87 Hz, 2H).

Example 94

1-cyclobutyl-3-{[1-(methylsulfonyl)piperidin-3-yl]methyl}-3,4,6,7,8,9-hexahydro-5H-pyrazolo[3,4-c]isoquinolin-5-one To a solution of Example 86 (170 mg, 0.5 mmol) in pyridine (5 mL) was added methanesulfonyl chloride (68 mg, 0.6 mmol). The reaction mixture was stirred at rt for 1 h and concentrated. The residual solid was washed with MeOH, and dried to give Example 94. Yield: 102 mg (49%). MS (DCI): m/z 419 (M+H)$^+$; $^1$H NMR (500 MHz, DMSO-d$_6$) δ 0.86-1.24 (m, 1H), 1.26-1.57 (m, 1H), 1.64 (s, 1H), 1.67-1.82 (m, 5H), 1.81-1.93 (m, 1H), 1.92-2.07 (m, 2H), 2.15 (s, 1H), 2.22-2.37 (m, 5H), 2.35-2.48 (m, 2H), 2.67-2.80 (m, 1H), 2.80 (s, 3H), 2.81-2.87 (m, 3H), 3.46 (d, J=3.36 Hz, 2H), 3.81 (d, J=8.24 Hz, 1H).

Example 95

1-cyclobutyl-3-[3-(1H-tetrazol-5-yl)benzyl]-3,4,6,7,8,9-hexahydro-5H-pyrazolo[3,4-c]isoquinolin-5-one Example 95A 3-((1-cyclobutyl-5-oxo-4,5,6,7,8,9-hexahydro-3H-pyrazolo[3,4-c]isoquinolin-3-yl)methyl)benzonitrile The title compound was prepared according to procedure for Example 85A-85D substituting 3-cyanobenzaldehyde for pyridine-3-aldehyde. MS (DCI/NH$_3$) m/z 359 (M+H)$^+$.

Example 95B 1-cyclobutyl-3-[3-(1H-tetrazol-5-yl)benzyl]-3,4,6,7,8,9-hexahydro-5H-pyrazolo[3,4-c]isoquinolin-5-one To a suspension of Example 95A (150 mg) and trimethylsily azide (582 mg) in toluene (20 ml) was added dibutyltin oxide (28 mg). The mixture was heated at 100° C. for 3 days. Solid material was collected by filtration, washed with methanol and dried to give Example 95. Yield: 100 mg. MS (DCI/NH$_3$) m/z 402 (M+H)$^+$; $^1$H NMR (500 MHz, CD$_3$OD): δ 1.81 (s, 2H), 1.92 (m, 1H), 2.02-2.11 (m, 1H), 2.35-2.44 (m, 4H), 2.51 (m, 2H), 2.91 (br s, 2H), 3.84-3.90 (m, 1H), 5.37 (br s, 1H), 5.51 (s, 2H), 5.51 (s, 2H), 7.30 (m, 2H), 7.97 (m, 2H), Example 96

7,9-dimethyl-1,2,3,4,6,7-hexahydro-5H-pyrazolo[3,4-h]-1,6-naphthyridin-5-one

Example 96A 5-chloro-N-(4-cyano-1,3-dimethyl-1H-pyrazol-5-yl)pentanamide

To a solution of 5-amino-1,3-dimethyl-1H-pyrazole-4-carbonitrile (1.59 g, 11.67 mmol) in anhydrous pyridine (15 mL) was slowly added 5-chlorovaleryl chloride (1.80 mL, 14.0 mmol) at 0° C. After addition, the reaction mixture was allowed to warm up to rt and stir at rt overnight. The reaction mixture was concentrated on a rotavapor and the residue was partitioned between ethyl acetate and brine. The organic phase was washed with brine and concentrated. The residue was separated by flash chromatography (silica gel, 50-80% gradient EtOAc in hexane) to provide Example 96A. Yield: 2.42 g (81%). MS (DCI): m/z 255 (M+H)$^+$.

Example 96B 7,9-dimethyl-1,2,3,4,6,7-hexahydro-5H-pyrazolo[3,4-h]-1,6-naphthyridin-5-one To a stirring solution of 2,2,6,6-tetramethylpiperidine (1.66 mL, 9.8 mmol) in anhydrous THF (20 mL) was added n-butyllithium (2.5 M solution in hexane, 3.92 mL, 9.8 mmol) at −20° C. The solution was stirred at −20° C. for 30 min, and a solution of Example 96A (1.0 g, 3.92 mmol) in 10 mL of anhydrous THF was added dropwise. The resulting dark red mixture was stirred at the same temperature for 30 min. The reaction was quenched with water, and the mixture was concentrated. The residue was partitioned between ethyl acetate and brine. The formed solid material in the bi-phase mixture was collected by filtration, washed with EtOAc and water.

The obtained crude product was recrystallized from methanol to give Example 96. Yield: 343 mg (40%). MS (DCI): m/z 219 (M+H)+; 1H NMR (300 MHz, DMSO-d6): δ 1.71-1.79 (m, 2H), 2.33-2.37 (m, 5H), 3.20-3.25 (m, 2H), 3.65 (s, 3H), 6.04 (br s, 1H), 11.06 (br s, 1H).

Example 97

1-{[cyclohexyl(methyl)amino]methyl}-3-methyl-3,4,6,7,8,9-hexahydro-5H-pyrazolo[3,4-c]isoquinolin-5-one The title compound was prepared according to procedure for Example 53 substituting cyclohexanone for acetone. Yield: 34%. MS (DCI/NH3) m/z 329 (M+H)+; 1H NMR (500 MHz, CD3OD): δ 1.23-1.32 (m, 1H), 1.38-1.48 (m, 2H), 1.58-1.69 (m, 2H), 1.71-1.77 (m, 1H), 1.79-1.84 (m, 2H), 1.85-1.90 (m, 2H), 1.94-2.01 (m, 2H), 2.13-2.22 (m, 2H), 2.50 (t, J=5.95 Hz, 2H), 2.92 (s, 3H), 2.95-3.03 (m, 2H), 3.43-3.52 (m, 1H), 3.92 (s, 3H), 4.42 (d, J=14.65 Hz, 1H), 4.80 (d, J=14.65 Hz, 1H); Anal. Calcd for $C_{19}H_{28}N_4O \cdot 1.6$ HCl: C, 59.00; H, 7.71; N, 14.48. Found: C, 59.07; H, 7.36; N, 14.20.

Example 98

3-methyl-1-[1-(2-phenylethyl)piperidin-4-yl]-3,4,6,7,8,9-hexahydro-5H-pyrazolo[3,4-c]isoquinolin-5-one The title compound was prepared according to procedure for Example 73 substituting phenylacetaldehyde for formaldehyde. Yield: 34%. MS (DCI/NH3) m/z 391 (M+H)+; 1H NMR (500 MHz, CD3OD): δ 1.78-1.89 (m, 5H), 2.11-2.20 (m, 2H), 2.22-2.29 (m, 2H), 2.46-2.54 (m, 2H), 2.98 (q, J=5.59 Hz, 2H), 3.08-3.14 (m, 2H), 3.18-3.26 (m, 2H), 3.36-3.42 (m, 2H), 3.77 (d, J=12.51 Hz, 2H), 3.83 (s, 3H), 7.27-7.30 (m, 1H), 7.31-7.33 (m, 1H), 7.33-7.36 (m, 2H), 7.36-7.38 (m, 1H); Anal. Calcd for $C_{24}H_{30}N_4O \cdot 2.1$ HCl: C, 61.71; H, 6.93; N, 11.99. Found: C, 61.89; H, 6.75; N, 11.81.

Example 99

3-methyl-1-[(2S)-1-methylpiperidin-2-yl]-3,4,6,7,8,9-hexahydro-5H-pyrazolo[3,4-c]isoquinolin-5-one The title compound was prepared according to procedure for Example 26 substituting Example 54 for Example 25. The TFA salt was treated with 1.0 M soln of HCl in ether to yield the HCl salt. Yield: 54 mg, 58%. MS (DCI/NH3) m/z 301 (M+H)+; 1H NMR (400 MHz, CD3OD): δ 1.72-1.85 (m, 3H), 1.86-1.95 (m, 3H), 1.96-2.08 (m, 3H), 2.22-2.32 (m, 2H), 2.49-2.57 (m, 2H), 2.73-2.76 (m, 3H), 2.78-2.87 (m, 1H), 2.98-3.09 (m, 1H), 3.55-3.66 (m, 1H), 3.92 (s, 3H), 4.60 (d, J=11.66 Hz, 1H).

Example 100

3-methyl-1-{[methyl(propyl)amino]methyl}-3,4,6,7,8,9-hexahydro-5H-pyrazolo[3,4-c]isoquinolin-5-one The title compound was prepared according to procedure for Example 53 substituting propionaldehyde for acetone. Yield: 50%. MS (DCI/NH3) m/z 259 (M+H)+; 1H NMR (500 MHz, CD3OD): δ 1.04 (t, J=7.48 Hz, 3H), 1.78-1.92 (m, 6H), 2.50 (t, J=6.10 Hz, 2H), 2.88-2.96 (m, 2H), 2.98 (s, 3H), 3.15-3.26 (m, 1H), 3.33-3.43 (m, 1H), 3.92 (s, 3H), 4.54 (d, J=14.95 Hz, 1H), 4.73 (d, J=14.65 Hz, 1H).

Example 101

1-{[(cyclopropylmethyl)(methyl)amino]methyl}-3-methyl-3,4,6,7,8,9-hexahydro-5H-pyrazolo[3,4-c]isoquinolin-5-one The title compound was prepared according to procedure for Example 53 substituting cyclopropanecarboxaldehyde for acetone. Yield: 49%. MS (DCI/NH3) m/z 301 (M+H)+; 1H NMR (500 MHz, CD3OD): δ 0.47-0.52 (m, 2H), 0.78-0.84 (m, 2H), 1.21-1.29 (m, 1H), 1.80-1.90 (m, 4H), 2.51 (t, J=5.95 Hz, 2H), 2.95 (t, J=5.80 Hz, 2H), 3.04 (s, 3H), 3.17 (dd, J=13.27, 7.48 Hz, 1H), 3.32-3.37 (m, 1H), 3.92 (s, 3H), 4.53 (d, J=14.65 Hz, 1H), 4.84 (d, J=14.65 Hz, 1H).

Example 102

3-methyl-1-[(2R)-pyrrolidin-2-yl]-3,4,6,7,8,9-hexahydro-5H-pyrazolo[3,4-c]isoquinolin-5-one The title compound was prepared according to procedure for Examples 24B-24E and Example 25 substituting (R)-1-benzyl 2-methyl pyrrolidine-1,2-dicarboxylate for Example 24A. MS (DCI/NH3) m/z 273 (M+H)+; 1H NMR (500 MHz, CD3OD): δ 1.79-1.91 (m, 4H), 2.16-2.30 (m, 3H), 2.46-2.59 (m, 3H), 2.88-3.01 (m, 2H), 3.39-3.49 (m, 1H), 3.53-3.60 (m, 1H), 3.89 (s, 3H), 5.18 (t, J=6.90 Hz, 1H).

Example 103

3-methyl-1-[(2R)-1-methylpyrrolidin-2-yl]-3,4,6,7,8,9-hexahydro-5H-pyrazolo[3,4-c]isoquinolin-5-one The title compound was prepared according to procedure for Example 26 substituting Example 102 for Example 25. The TFA salt was treated with 1.0 M solution of HCl in ether to yield the HCl salt. Yield: 33 mg (56%). MS (DCI/NH3) m/z 287 (M+H)+; 1H NMR (500 MHz, CD3OD): δ 1.79-1.91 (m, 4H), 2.10-2.24 (m, 2H), 2.26-2.34 (m, 1H), 2.49-2.55 (m, 2H), 2.70-2.76 (m, 1H), 2.80-2.88 (m, 1H), 2.93-2.96 (m, 1H), 2.96 (s, 3H), 3.33-3.39 (m, 1H), 3.81-3.87 (m, 1H), 3.91 (s, 3H), 4.98 (t, J=8.39 Hz, 1H).

Example 104

1-[(2R)-1-(cyclopropylmethyl)pyrrolidin-2-yl]-3-methyl-3,4,6,7,8,9-hexahydro-5H-pyrazolo[3,4-c]isoquinolin-5-one The title compound was prepared according to procedure for Example 26, substituting Example 102 for Example 25, and cyclopropanecarboxaldehyde for formaldehyde. The TFA salt was treated with 1.0 M solution of HCl in ether to yield the HCl salt. Yield: 41 mg (56%). MS (DCI/NH3) m/z 327 (M+H)+; 1H NMR (500 MHz, CD3OD): δ 0.33-0.44 (m, 2H), 0.63-0.71 (m, 2H), 1.05-1.16 (m, 1H), 1.77-1.91 (m, 4H), 2.04-2.13 (m, 1H), 2.19-2.26 (m, 1H), 2.26-2.35 (m, 1H), 2.47-2.56 (m, 2H), 2.67-2.76 (m, 1H), 2.78-2.88 (m, 1H), 2.90-3.01 (m, 1H), 3.09-3.19 (m, 2H), 3.35-3.43 (m, 1H), 3.91 (s, 3H), 3.96-4.03 (m, 1H), 5.04 (t, J=8.54 Hz, 1H).

Example 105

3-methyl-1-(1-propylpiperidin-3-yl)-3,4,6,7,8,9-hexahydro-5H-pyrazolo[3,4-c]isoquinolin-5-one The title compound was prepared according to procedure for Example 26 substituting Example 63 for Example 25, and substituting propionaldehyde for formaldehyde. The TFA salt was treated with 1.0 M solution of HCl in ether to yield the HCl salt. Yield: 16 mg (12%). MS (DCI/NH$_3$) m/z 329 (M+H)$^+$; $^1$H NMR (500 MHz, C$_5$D$_5$N): δ 0.78 (t, J=7.32 Hz, 3H), 1.67-1.72 (m, 2H), 1.73-1.77 (m, 2H), 1.79-1.84 (m, 1H), 1.87-1.93 (m, 1H), 1.94-2.03 (m, 2H), 2.32 (d, J=13.43 Hz, 1H), 2.65-2.78 (m, 2H), 2.84 (t, J=5.80 Hz, 2H), 2.94-3.04 (m, 2H), 3.10-3.18 (m, 1H), 3.27-3.42 (m, 2H), 3.59 (d, J=7.63 Hz, 1H), 3.92 (d, J=10.98 Hz, 1H), 3.99 (s, 3H), 4.43-4.60 (m, 1H), 5.22 (br s, 1H)

Example 106

1-(3-{[(cyclopropylmethyl)amino]methyl}phenyl)-3-methyl-3,4,6,7,8,9-hexahydro-5H-pyrazolo[3,4-c]isoquinolin-5-one The title compound was prepared as TFA salt according to the procedure for related examples. MS (DCI): m/z 363 (M+H)$^+$.

Example 107

1-(3-{[bis(cyclopropylmethyl)amino]methyl}phenyl)-3-methyl-3,4,6,7,8,9-hexahydro-5H-pyrazolo[3,4-c]isoquinolin-5-one The title compound was prepared as TFA salt according to the procedure for related examples. MS (DCI): m/z 417 (M+H)$^+$.

Example 108

1-{3-[(cyclobutylamino)methyl]phenyl}-3-methyl-3,4,6,7,8,9-hexahydro-5H-pyrazolo[3,4-c]isoquinolin-5-one The title compound was prepared as TFA salt according to the procedure for related examples. MS (DCI): m/z 363 (M+H)$^+$.

Example 109

1-{3-[(dicyclobutylamino)methyl]phenyl}-3-methyl-3,4,6,7,8,9-hexahydro-5H-pyrazolo[3,4-c]isoquinolin-5-one The title compound was prepared as TFA salt according to the procedure for related examples. MS (DCI): m/z 417 (M+H)$^+$.

Example 110

1-{3-[(cyclopentylamino)methyl]phenyl}-3-methyl-3,4,6,7,8,9-hexahydro-5H-pyrazolo[3,4-c]isoquinolin-5-one The title compound was prepared as TFA salt according to the procedure for related examples. MS (DCI): m/z 377 (M+H)$^+$.

Example 111

3-methyl-1-{3-[(propylamino)methyl]phenyl}-3,4,6,7,8,9-hexahydro-5H-pyrazolo[3,4-c]isoquinolin-5-one The title compound was prepared as TFA salt according to the procedure for related examples. MS (DCI): m/z 351 (M+H)$^+$.

Example 112

1-{3-[(cycloheptylamino)methyl]phenyl}-3-methyl-3,4,6,7,8,9-hexahydro-5H-pyrazolo[3,4-c]isoquinolin-5-one The title compound was prepared as TFA salt according to the procedure for related examples. MS (DCI): m/z 405 (M+H)$^+$.

Example 113

1-{3-[(cyclohexylamino)methyl]phenyl}-3-methyl-3,4,6,7,8,9-hexahydro-5H-pyrazolo[3,4-c]isoquinolin-5-one The title compound was prepared as TFA salt according to the procedure for related examples. MS (DCI): m/z 391 (M+H)$^+$.

Example 114

1-{3-[(isopropylamino)methyl]phenyl}-3-methyl-3,4,6,7,8,9-hexahydro-5H-pyrazolo[3,4-c]isoquinolin-5-one The title compound was prepared as TFA salt according to the procedure for related examples. MS (DCI): m/z 351 (M+H)$^+$.

Example 115

1-{3-[(isobutylamino)methyl]phenyl}-3-methyl-3,4,6,7,8,9-hexahydro-5H-pyrazolo[3,4-c]isoquinolin-5-one The title compound was prepared as TFA salt according to the procedure for related examples. MS (DCI): m/z 365 (M+H)$^+$.

Example 116 benzyl 3-(3-methyl-5-oxo-4,5,6,7,8,9-hexahydro-3H-pyrazolo[3,4-c]isoquinolin-1-yl)azetidine-1-carboxylate The title compound was prepared as TFA salt according to the procedure for related examples. MS (DCI): m/z 393 (M+H)$^+$.

Example 117

3-methyl-1-(1-methylazetidin-3-yl)-3,4,6,7,8,9-hexahydro-5H-pyrazolo[3,4-c]isoquinolin-5-one The title compound was prepared as TFA salt according to the procedure for related examples. MS (DCI): m/z 273 (M+H)$^+$.

Example 118

3-methyl-1-(1-propylazetidin-3-yl)-3,4,6,7,8,9-hexahydro-5H-pyrazolo[3,4-c]isoquinolin-5-one The title compound was prepared as TFA salt according to the procedure for related examples. MS (DCI): m/z 301 (M+H)$^+$.

Example 119

1-(1-isopropylazetidin-3-yl)-3-methyl-3,4,6,7,8,9-hexahydro-5H-pyrazolo[3,4-c]isoquinolin-5-one The title compound was prepared as TFA salt according to the procedure for related examples. MS (DCI): m/z 301 (M+H)$^+$.

Example 120

1-(1-cyclopentylazetidin-3-yl)-3-methyl-3,4,6,7,8,9-hexahydro-5H-pyrazolo[3,4-c]isoquinolin-5-one The title compound was prepared as TFA salt according to the procedure for related examples. MS (DCI): m/z 327 (M+H)$^+$.

Example 121

1-(1-cyclohexylazetidin-3-yl)-3-methyl-3,4,6,7,8,9-hexahydro-5H-pyrazolo[3,4-c]isoquinolin-5-one The title compound was prepared as TFA salt according to the procedure for related examples. MS (DCI): m/z 341 (M+H)$^+$.

Example 122

1-(1-cycloheptylazetidin-3-yl)-3-methyl-3,4,6,7,8,9-hexahydro-5H-pyrazolo[3,4-c]isoquinolin-5-one The title compound was prepared as TFA salt according to the procedure for related examples. MS (DCI): m/z 355 (M+H)$^+$.

Example 123

1-[1-(cyclopropylmethyl)azetidin-3-yl]-3-methyl-3,4,6,7,8,9-hexahydro-5H-pyrazolo[3,4-c]isoquinolin-5-one The title compound was prepared as TFA salt according to the procedure for related examples. MS (DCI): m/z 313 (M+H)$^+$.

Example 124

1-(1-isobutylazetidin-3-yl)-3-methyl-3,4,6,7,8,9-hexahydro-5H-pyrazolo[3,4-c]isoquinolin-5-one The title compound was prepared as TFA salt according to the procedure for related examples. MS (DCI): m/z 315 (M+H)$^+$.

Example 125 benzyl 2-(3-ethyl-5-oxo-4,5,6,7,8,9-hexahydro-3H-pyrazolo[3,4-c]isoquinolin-1-yl)pyrrolidine-1-carboxylate The title compound was prepared as TFA salt according to the procedure for related examples. MS (DCI): m/z 421 (M+H)$^+$.

Example 126

3-ethyl-1-pyrrolidin-2-yl-3,4,6,7,8,9-hexahydro-5H-pyrazolo[3,4-c]isoquinolin-5-one The title compound was prepared as TFA salt according to the procedure for related examples. MS (DCI): m/z 287 (M+H)$^+$.

Example 127 benzyl 4-[(3-methyl-5-oxo-4,5,6,7,8,9-hexahydro-3H-pyrazolo[3,4-c]isoquinolin-1-yl)methyl]benzyl-carbamate The title compound was prepared as TFA salt according to the procedure for related examples. MS (DCI): m/z 457 (M+H)$^+$.

Example 128 benzyl 2-[5-oxo-3-(2,2,2-trifluoroethyl)-4,5,6,7,8,9-hexahydro-3H-pyrazolo[3,4-c]isoquinolin-1-yl]pyrrolidine-1-carboxylate The title compound was prepared as TFA salt according to the procedure for related examples. MS (DCI): m/z 475 (M+H)$^+$.

Example 129

1-(1-cyclobutylpyrrolidin-2-yl)-3-ethyl-3,4,6,7,8,9-hexahydro-5H-pyrazolo[3,4-c]isoquinolin-5-one The title compound was prepared as TFA salt according to the procedure for related examples. MS (DCI): m/z 341 (M+H)$^+$.

Example 130

1-[1-(cyclopropylmethyl)pyrrolidin-2-yl]-3-ethyl-3,4,6,7,8,9-hexahydro-5H-pyrazolo[3,4-c]isoquinolin-5-one The title compound was prepared as TFA salt according to the procedure for related examples. MS (DCI): m/z 341 (M+H)$^+$.

Example 131

1-(1-cyclopentylpyrrolidin-2-yl)-3-ethyl-3,4,6,7,8,9-hexahydro-5H-pyrazolo[3,4-c]isoquinolin-5-one The title compound was prepared as TFA salt according to the procedure for related examples. MS (DCI): m/z 355 (M+H)$^+$.

Example 132

1-(1-cyclohexylpyrrolidin-2-yl)-3-ethyl-3,4,6,7,8,9-hexahydro-5H-pyrazolo[3,4-c]isoquinolin-5-one The title compound was prepared as TFA salt according to the procedure for related examples. MS (DCI): m/z 369 (M+H)⁺.

Example 133

1-(1-cycloheptylpyrrolidin-2-yl)-3-ethyl-3,4,6,7,8,9-hexahydro-5H-pyrazolo[3,4-c]isoquinolin-5-one The title compound was prepared as TFA salt according to the procedure for related examples. MS (DCI): m/z 383 (M+H)⁺.

Example 134

3-ethyl-1-(1-isopropylpyrrolidin-2-yl)-3,4,6,7,8,9-hexahydro-5H-pyrazolo[3,4-c]isoquinolin-5-one The title compound was prepared as TFA salt according to the procedure for related examples. MS (DCI): m/z 329 (M+H)⁺.

Example 135

3-ethyl-1-[1-(1-ethylpropyl)pyrrolidin-2-yl]-3,4,6,7,8,9-hexahydro-5H-pyrazolo[3,4-c]isoquinolin-5-one The title compound was prepared as TFA salt according to the procedure for related examples. MS (DCI): m/z 357 (M+H)⁺.

Example 136

1-{4-[(cyclobutylamino)methyl]benzyl}-3-methyl-3,4,6,7,8,9-hexahydro-5H-pyrazolo[3,4-c]isoquinolin-5-one The title compound was prepared as TFA salt according to the procedure for related examples. MS (DCI): m/z 376 (M+H)⁺.

Example 137

1-{4-[(dicyclobutylamino)methyl]benzyl}-3-methyl-3,4,6,7,8,9-hexahydro-5H-pyrazolo[3,4-c]isoquinolin-5-one The title compound was prepared as TFA salt according to the procedure for related examples. MS (DCI): m/z 431 (M+H)⁺.

Example 138

1-{4-[(cyclopentylamino)methyl]benzyl}-3-methyl-3,4,6,7,8,9-hexahydro-5H-pyrazolo[3,4-c]isoquinolin-5-one The title compound was prepared as TFA salt according to the procedure for related examples. MS (DCI): m/z 391 (M+H)⁺.

Example 139

1-{4-[(cyclohexylamino)methyl]benzyl}-3-methyl-3,4,6,7,8,9-hexahydro-5H-pyrazolo[3,4-c]isoquinolin-5-one The title compound was prepared as TFA salt according to the procedure for related examples. MS (DCI): m/z 405 (M+H)⁺.

Example 140

1-[(2R)-pyrrolidin-2-yl]-3-(2,2,2-trifluoroethyl)-3,4,6,7,8,9-hexahydro-5H-pyrazolo[3,4-c]isoquinolin-5-one The title compound was prepared as TFA salt according to the procedure for related examples. MS (DCI): m/z 341 (M+H)⁺.

Example 141

1-[(2R)-1-isopropylpyrrolidin-2-yl]-3-(2,2,2-trifluoroethyl)-3,4,6,7,8,9-hexahydro-5H-pyrazolo[3,4-c]isoquinolin-5-one The title compound was prepared as TFA salt according to the procedure for related examples. MS (DCI): m/z 383 (M+H)⁺.

Example 142

1-[(2R)-1-cyclobutylpyrrolidin-2-yl]-3-(2,2,2-trifluoroethyl)-3,4,6,7,8,9-hexahydro-5H-pyrazolo[3,4-c]isoquinolin-5-one The title compound was prepared as TFA salt according to the procedure for related examples. MS (DCI): m/z 395 (M+H)⁺.

Example 143

1-[(2R)-1-(cyclopropylmethyl)pyrrolidin-2-yl]-3-(2,2,2-trifluoroethyl)-3,4,6,7,8,9-hexahydro-5H-pyrazolo[3,4-c]isoquinolin-5-one The title compound was prepared as TFA salt according to the procedure for related examples. MS (DCI): m/z 395 (M+H)⁺.

Example 144

1-[(2R)-1-cyclopentylpyrrolidin-2-yl]-3-(2,2,2-trifluoroethyl)-3,4,6,7,8,9-hexahydro-5H-pyrazolo[3,4-c]isoquinolin-5-one The title compound was prepared as TFA salt according to the procedure for related examples. MS (DCI): m/z 409 (M+H)⁺.

Example 145

1-[(2R)-1-cyclohexylpyrrolidin-2-yl]-3-(2,2,2-trifluoroethyl)-3,4,6,7,8,9-hexahydro-5H-pyrazolo[3,4-c]isoquinolin-5-one The title compound was prepared as TFA salt according to the procedure for related examples. MS (DCI): m/z 423 (M+H)⁺.

Example 146

1-[(2R)-1-cycloheptylpyrrolidin-2-yl]-3-(2,2,2-trifluoroethyl)-3,4,6,7,8,9-hexahydro-5H-pyrazolo[3,4-c]isoquinolin-5-one The title compound was prepared as TFA salt according to the procedure for related examples. MS (DCI): m/z 437 (M+H)+.

Example 147

2-{5-oxo-1-[(2R)-pyrrolidin-2-yl]-4,5,6,7,8,9-hexahydro-3H-pyrazolo[3,4-c]isoquinolin-3-yl}ethyl ethylcarbamate The title compound was prepared as TFA salt according to the procedure for related examples. MS (DCI): m/z 374 (M+H)+.

Example 148

2-{1-[(2R)-1-isopropylpyrrolidin-2-yl]-5-oxo-4,5,6,7,8,9-hexahydro-3H-pyrazolo[3,4-c]isoquinolin-3-yl}ethyl ethylcarbamate The title compound was prepared as TFA salt according to the procedure for related examples. MS (DCI): m/z 415 (M+H)+.

Example 149

2-{5-oxo-1-[(2R)-1-propylpyrrolidin-2-yl]-4,5,6,7,8,9-hexahydro-3H-pyrazolo[3,4-c]isoquinolin-3-yl}ethyl ethylcarbamate The title compound was prepared as TFA salt according to the procedure for related examples. MS (DCI): m/z 415 (M+H)+.

Example 150

2-{1-[(2R)-1-cyclobutylpyrrolidin-2-yl]-5-oxo-4,5,6,7,8,9-hexahydro-3H-pyrazolo[3,4-c]isoquinolin-3-yl}ethyl ethylcarbamate The title compound was prepared as TFA salt according to the procedure for related examples. MS (DCI): m/z 428 (M+H)+.

Example 151

2-{1-[(2R)-1-(cyclopropylmethyl)pyrrolidin-2-yl]-5-oxo-4,5,6,7,8,9-hexahydro-3H-pyrazolo[3,4-c]isoquinolin-3-yl}ethyl ethylcarbamate The title compound was prepared as TFA salt according to the procedure for related examples. MS (DCI): m/z 428 (M+H)+.

Example 152

2-{1-[(2R)-1-cyclopentylpyrrolidin-2-yl]-5-oxo-4,5,6,7,8,9-hexahydro-3H-pyrazolo[3,4-c]isoquinolin-3-yl}ethyl ethylcarbamate The title compound was prepared as TFA salt according to the procedure for related examples. MS (DCI): m/z 442 (M+H)+.

Example 153

2-{1-[(2R)-1-cyclohexylpyrrolidin-2-yl]-5-oxo-4,5,6,7,8,9-hexahydro-3H-pyrazolo[3,4-c]isoquinolin-3-yl}ethyl ethylcarbamate The title compound was prepared as TFA salt according to the procedure for related examples. MS (DCI): m/z 456 (M+H)+.

Example 154

2-{1-[(2R)-1-cycloheptylpyrrolidin-2-yl]-5-oxo-4,5,6,7,8,9-hexahydro-3H-pyrazolo[3,4-c]isoquinolin-3-yl}ethyl ethylcarbamate The title compound was prepared as TFA salt according to the procedure for related examples. MS (DCI): m/z 470 (M+H)+.

Example 155

3-{5-oxo-1-[(2R)-pyrrolidin-2-yl]-4,5,6,7,8,9-hexahydro-3H-pyrazolo[3,4-c]isoquinolin-3-yl}propanenitrile The title compound was prepared as TFA salt according to the procedure for related examples. MS (DCI): m/z 312 (M+H)+.

Example 156

3-{1-[(2R)-1-isopropylpyrrolidin-2-yl]-5-oxo-4,5,6,7,8,9-hexahydro-3H-pyrazolo[3,4-c]isoquinolin-3-yl}propanenitrile The title compound was prepared as TFA salt according to the procedure for related examples. MS (DCI): m/z 354 (M+H)+.

Example 157

3-{1-[(2R)-1-cyclobutylpyrrolidin-2-yl]-5-oxo-4,5,6,7,8,9-hexahydro-3H-pyrazolo[3,4-c]isoquinolin-3-yl}propanenitrile The title compound was prepared as TFA salt according to the procedure for related examples. MS (DCI): m/z 366 (M+H)+.

Example 158

3-{1-[(2R)-1-(cyclopropylmethyl)pyrrolidin-2-yl]-5-oxo-4,5,6,7,8,9-hexahydro-3H-pyrazolo[3,4-c]isoquinolin-3-yl}propanenitrile The title compound was prepared as TFA salt according to the procedure for related examples. MS (DCI): m/z 366 (M+H)+.

Example 159

3-{1-[(2R)-1-cyclopentylpyrrolidin-2-yl]-5-oxo-4,5,6,7,8,9-hexahydro-3H-pyrazolo[3,4-c]isoquinolin-3-yl}propanenitrile The title compound was prepared as TFA salt according to the procedure for related examples. MS (DCI): m/z 380 (M+H)+.

Example 160

3-{1-[(2R)-1-cyclohexylpyrrolidin-2-yl]-5-oxo-4,5,6,7,8,9-hexahydro-3H-pyrazolo[3,4-c]isoquinolin-3-yl}propanenitrile The title compound was prepared as TFA salt according to the procedure for related examples. MS (DCI): m/z 394 (M+H)$^+$.

Example 161

3-{1-[(2R)-1-cycloheptylpyrrolidin-2-yl]-5-oxo-4,5,6,7,8,9-hexahydro-3H-pyrazolo[3,4-c]isoquinolin-3-yl}propanenitrile The title compound was prepared as TFA salt according to the procedure for related examples. MS (DCI): m/z 408 (M+H)$^+$.

Example 162

3-(3-hydroxybenzyl)-1-pyrrolidin-2-yl-3,4,6,7,8,9-hexahydro-5H-pyrazolo[3,4-c]isoquinolin-5-one The title compound was prepared as TFA salt according to the procedure for related examples. MS (DCI): m/z 365 (M+H)$^+$.

Example 163

3-(3-hydroxypropyl)-1-[(2R)-pyrrolidin-2-yl]-3,4,6,7,8,9-hexahydro-5H-pyrazolo[3,4-c]isoquinolin-5-one The title compound was prepared as TFA salt according to the procedure for related examples. MS (DCI): m/z 451 (M+H)$^+$.

Example 164

3-[3-(cyclopentylamino)propyl]-1-[(2R)-pyrrolidin-2-yl]-3,4,6,7,8,9-hexahydro-5H-pyrazolo[3,4-c]isoquinolin-5-one The title compound was prepared as TFA salt according to the procedure for related examples. MS (DCI): m/z 384 (M+H)$^+$.

Example 165

3-(3-hydroxybenzyl)-1-[(2R)-1-methylpyrrolidin-2-yl]-3,4,6,7,8,9-hexahydro-5H-pyrazolo[3,4-c]isoquinolin-5-one The title compound was prepared as TFA salt according to the procedure for related examples. MS (DCI): m/z 379 (M+H)$^+$.

Example 166

3-(3-hydroxybenzyl)-1-[(2R)-1-isopropylpyrrolidin-2-yl]-3,4,6,7,8,9-hexahydro-5H-pyrazolo[3,4-c]isoquinolin-5-one The title compound was prepared as TFA salt according to the procedure for related examples. MS (DCI): m/z 407 (M+H)$^+$.

Example 167

1-[(2R)-1-(cyclopropylmethyl)pyrrolidin-2-yl]-3-(3-hydroxybenzyl)-3,4,6,7,8,9-hexahydro-5H-pyrazolo[3,4-c]isoquinolin-5-one The title compound was prepared as TFA salt according to the procedure for related examples. MS (DCI): m/z 419 (M+H)$^+$.

Example 168

1-[(2R)-1-cyclopentylpyrrolidin-2-yl]-3-(3-hydroxybenzyl)-3,4,6,7,8,9-hexahydro-5H-pyrazolo[3,4-c]isoquinolin-5-one The title compound was prepared as TFA salt according to the procedure for related examples. MS (DCI): m/z 433 (M+H)$^+$.

Example 169

1-[(2R)-1-cyclohexylpyrrolidin-2-yl]-3-(3-hydroxybenzyl)-3,4,6,7,8,9-hexahydro-5H-pyrazolo[3,4-c]isoquinolin-5-one The title compound was prepared as TFA salt according to the procedure for related examples. MS (DCI): m/z 447 (M+H)$^+$.

Example 170

1-[(2R)-1-cycloheptylpyrrolidin-2-yl]-3-(3-hydroxybenzyl)-3,4,6,7,8,9-hexahydro-5H-pyrazolo[3,4-c]isoquinolin-5-one The title compound was prepared as TFA salt according to the procedure for related examples. MS (DCI): m/z 461 (M+H)$^+$.

Example 171

3-[3-(dimethylamino)propyl]-1-pyrrolidin-2-yl-3,4,6,7,8,9-hexahydro-5H-pyrazolo[3,4-c]isoquinolin-5-one The title compound was prepared as TFA salt according to the procedure for related examples. MS (DCI): m/z 344 (M+H)$^+$.

Example 172

3-[3-(methylamino)propyl]-1-pyrrolidin-2-yl-3,4,6,7,8,9-hexahydro-5H-pyrazolo[3,4-c]isoquinolin-5-one The title compound was prepared as TFA salt according to the procedure for related examples. MS (DCI): m/z 330 (M+H)$^+$.

Example 173

3-[3-(ethylamino)propyl]-1-pyrrolidin-2-yl-3,4,6,7,8,9-hexahydro-5H-pyrazolo[3,4-c]isoquinolin-5-one The title compound was prepared as TFA salt according to the procedure for related examples. MS (DCI): m/z 344 (M+H)$^+$.

Example 174

3-[3-(isopropylamino)propyl]-1-pyrrolidin-2-yl-3,4,6,7,8,9-hexahydro-5H-pyrazolo[3,4-c]isoquinolin-5-one The title compound was prepared as TFA salt according to the procedure for related examples. MS (DCI): m/z 358 (M+H)$^+$.

Example 175

3-[3-(cyclopropylamino)propyl]-1-pyrrolidin-2-yl-3,4,6,7,8,9-hexahydro-5H-pyrazolo[3,4-c]isoquinolin-5-one The title compound was prepared as TFA salt according to the procedure for related examples. MS (DCI): m/z 356 (M+H)$^+$.

Example 176

3-[3-(cyclobutylamino)propyl]-1-pyrrolidin-2-yl-3,4,6,7,8,9-hexahydro-5H-pyrazolo[3,4-c]isoquinolin-5-one The title compound was prepared as TFA salt according to the procedure for related examples. MS (DCI): m/z 370 (M+H)$^+$.

Example 177

3-[3-(cyclohexylamino)propyl]-1-pyrrolidin-2-yl-3,4,6,7,8,9-hexahydro-5H-pyrazolo[3,4-c]isoquinolin-5-one The title compound was prepared as TFA salt according to the procedure for related examples. MS (DCI): m/z 398 (M+H)$^+$.

Example 178

1-pyrrolidin-2-yl-3-(3-pyrrolidin-1-ylpropyl)-3,4,6,7,8,9-hexahydro-5H-pyrazolo[3,4-c]isoquinolin-5-one The title compound was prepared as TFA salt according to the procedure for related examples. MS (DCI): m/z 370 (M+H)$^+$.

Example 179

3-(3-piperidin-1-ylpropyl)-1-pyrrolidin-2-yl-3,4,6,7,8,9-hexahydro-5H-pyrazolo[3,4-c]isoquinolin-5-one The title compound was prepared as TFA salt according to the procedure for related examples. MS (DCI): m/z 384 (M+H)$^+$.

Example 180

3-(3-morpholin-4-ylpropyl)-1-pyrrolidin-2-yl-3,4,6,7,8,9-hexahydro-5H-pyrazolo[3,4-c]isoquinolin-5-one The title compound was prepared as TFA salt according to the procedure for related examples. MS (DCI): m/z 386 (M+H)$^+$.

Example 181

1-cyclobutyl-3-[3-(methylamino)propyl]-3,4,6,7,8,9-hexahydro-5H-pyrazolo[3,4-c]isoquinolin-5-one The title compound was prepared as TFA salt according to the procedure for related examples. MS (DCI): m/z 315 (M+H)$^+$.

Example 182

1-cyclobutyl-3-[3-(isopropylamino)propyl]-3,4,6,7,8,9-hexahydro-5H-pyrazolo[3,4-c]isoquinolin-5-one The title compound was prepared as TFA salt according to the procedure for related examples. MS (DCI): m/z 343 (M+H)$^+$.

Example 183

1-cyclobutyl-3-[3-(cyclopropylamino)propyl]-3,4,6,7,8,9-hexahydro-5H-pyrazolo[3,4-c]isoquinolin-5-one The title compound was prepared as TFA salt according to the procedure for related examples. MS (DCI): m/z 341 (M+H)$^+$.

Example 184

1-cyclobutyl-3-[3-(cyclobutylamino)propyl]-3,4,6,7,8,9-hexahydro-5H-pyrazolo[3,4-c]isoquinolin-5-one The title compound was prepared as TFA salt according to the procedure for related examples. MS (DCI): m/z 355 (M+H)$^+$.

Example 185

1-cyclobutyl-3-[3-(cyclopentylamino)propyl]-3,4,6,7,8,9-hexahydro-5H-pyrazolo[3,4-c]isoquinolin-5-one The title compound was prepared as TFA salt according to the procedure for related examples. MS (DCI): m/z 369 (M+H)$^+$.

Example 186

1-cyclobutyl-3-[3-(cyclohexylamino)propyl]-3,4,6,7,8,9-hexahydro-5H-pyrazolo[3,4-c]isoquinolin-5-one The title compound was prepared as TFA salt according to the procedure for related examples. MS (DCI): m/z 382 (M+H)$^+$.

Example 187

1-cyclobutyl-3-(3-piperidin-1-ylpropyl)-3,4,6,7,8,9-hexahydro-5H-pyrazolo[3,4-c]isoquinolin-5-one The title compound was prepared as TFA salt according to the procedure for related examples. MS (DCI): m/z 369 (M+H)$^+$.

Example 188

1-cyclobutyl-3-(3-morpholin-4-ylpropyl)-3,4,6,7,8,9-hexahydro-5H-pyrazolo[3,4-c]isoquinolin-5-one The title compound was prepared as TFA salt according to the procedure for related examples. MS (DCI): m/z 371 (M+H)$^+$.

Example 189

3-(1-cyclobutyl-5-oxo-4,5,6,7,8,9-hexahydro-3H-pyrazolo[3,4-c]isoquinolin-3-yl)propanenitrile The title compound was prepared as TFA salt according to the procedure for related examples. MS (DCI): m/z 297 (M+H)$^+$.

Example 190

3-(1-cyclobutyl-5-oxo-4,5,6,7,8,9-hexahydro-3H-pyrazolo[3,4-c]isoquinolin-3-yl)propanal The title compound was prepared as TFA salt according to the procedure for related examples. MS (DCI): m/z 300 (M+H)$^+$.

Example 191

1-cyclobutyl-3-(3-hydroxypropyl)-3,4,6,7,8,9-hexahydro-5H-pyrazolo[3,4-c]isoquinolin-5-one The title compound was prepared as TFA salt according to the procedure for related examples. MS (DCI): m/z 302 (M+H)$^+$.

Example 192

1-cyclobutyl-3-[4-(dimethylamino)benzyl]-3,4,6,7,8,9-hexahydro-5H-pyrazolo[3,4-c]isoquinolin-5-one The title compound was prepared as TFA salt according to the procedure for related examples. MS (DCI): m/z 377 (M+H)$^+$.

Example 193

3-isopropyl-1-(1-isopropylpyrrolidin-2-yl)-3,4,6,7,8,9-hexahydro-5H-pyrazolo[3,4-c]isoquinolin-5-one The title compound was prepared as TFA salt according to the procedure for related examples. MS (DCI): m/z 343 (M+H)$^+$.

Example 194

1-[1-(cyclopropylmethyl)pyrrolidin-2-yl]-3-isopropyl-3,4,6,7,8,9-hexahydro-5H-pyrazolo[3,4-c]isoquinolin-5-one The title compound was prepared as TFA salt according to the procedure for related examples. MS (DCI): m/z 355 (M+H)$^+$.

Example 195

1-(1-cyclobutylpyrrolidin-2-yl)-3-isopropyl-3,4,6,7,8,9-hexahydro-5H-pyrazolo[3,4-c]isoquinolin-5-one The title compound was prepared as TFA salt according to the procedure for related examples. MS (DCI): m/z 355 (M+H)$^+$.

Example 196

1-(1-cyclopentylpyrrolidin-2-yl)-3-isopropyl-3,4,6,7,8,9-hexahydro-5H-pyrazolo[3,4-c]isoquinolin-5-one The title compound was prepared as TFA salt according to the procedure for related examples. MS (DCI): m/z 369 (M+H)$^+$.

Example 197

1-(1-cyclohexylpyrrolidin-2-yl)-3-isopropyl-3,4,6,7,8,9-hexahydro-5H-pyrazolo[3,4-c]isoquinolin-5-one The title compound was prepared as TFA salt according to the procedure for related examples. MS (DCI): m/z 383 (M+H)$^+$.

Example 198

3-[(1-cyclobutyl-5-oxo-4,5,6,7,8,9-hexahydro-3H-pyrazolo[3,4-c]isoquinolin-3-yl)methyl]benzonitrile The title compound was prepared as TFA salt according to the procedure for related examples. MS (DCI): m/z 359 (M+H)$^+$.

Example 199

1-cyclobutyl-3-{4-[(methylamino)methyl]benzyl}-3,4,6,7,8,9-hexahydro-5H-pyrazolo[3,4-c]isoquinolin-5-one The title compound was prepared as TFA salt according to the procedure for related examples. MS (DCI): m/z 377 (M+H)$^+$.

Example 200

1-cyclobutyl-3-{4-[(ethylamino)methyl]benzyl}-3,4,6,7,8,9-hexahydro-5H-pyrazolo[3,4-c]isoquinolin-5-one The title compound was prepared as TFA salt according to the procedure for related examples. MS (DCI): m/z 391 (M+H)$^+$.

Example 201

1-cyclobutyl-3-{4-[(dimethylamino)methyl]benzyl}-3,4,6,7,8,9-hexahydro-5H-pyrazolo[3,4-c]isoquinolin-5-one The title compound was prepared as TFA salt according to the procedure for related examples. MS (DCI): m/z 391 (M+H)$^+$.

Example 202

1-cyclobutyl-3-{4-[(cyclopropylamino)methyl]benzyl}-3,4,6,7,8,9-hexahydro-5H-pyrazolo[3,4-c]isoquinolin-5-one The title compound was prepared as TFA salt according to the procedure for related examples. MS (DCI): m/z 403 (M+H)$^+$.

Example 203

1-cyclobutyl-3-{4-[(cyclobutylamino)methyl]benzyl}-3,4,6,7,8,9-hexahydro-5H-pyrazolo[3,4-c]isoquinolin-5-one The title compound was prepared as TFA salt according to the procedure for related examples. MS (DCI): m/z 417 (M+H)$^+$.

Example 204

1-cyclobutyl-3-{4-[(cyclohexylamino)methyl]benzyl}-3,4,6,7,8,9-hexahydro-5H-pyrazolo[3,4-c]isoquinolin-5-one The title compound was prepared as TFA salt according to the procedure for related examples. MS (DCI): m/z 445 (M+H)$^+$.

Example 205

1-cyclobutyl-3-[4-(hydroxymethyl)benzyl]-3,4,6,7,8,9-hexahydro-5H-pyrazolo[3,4-c]isoquinolin-5-one The title compound was prepared as TFA salt according to the procedure for related examples. MS (DCI): m/z 364 (M+H)$^+$.

Example 206

1-cyclobutyl-3-{4-[(cyclopentylamino)methyl]benzyl}-3,4,6,7,8,9-hexahydro-5H-pyrazolo[3,4-c]isoquinolin-5-one The title compound was prepared as TFA salt according to the procedure for related examples. MS (DCI): m/z 431 (M+H)$^+$.

Example 207

1-cyclobutyl-3-{3-[(methylamino)methyl]benzyl}-3,4,6,7,8,9-hexahydro-5H-pyrazolo[3,4-c]isoquinolin-5-one The title compound was prepared as TFA salt according to the procedure for related examples. MS (DCI): m/z 377 (M+H)$^+$.

Example 208

1-cyclobutyl-3-{3-[(ethylamino)methyl]benzyl}-3,4,6,7,8,9-hexahydro-5H-pyrazolo[3,4-c]isoquinolin-5-one The title compound was prepared as TFA salt according to the procedure for related examples. MS (DCI): m/z 391 (M+H)$^+$.

Example 209

1-cyclobutyl-3-{3-[(cyclopropylamino)methyl]benzyl}-3,4,6,7,8,9-hexahydro-5H-pyrazolo[3,4-c]isoquinolin-5-one The title compound was prepared as TFA salt according to the procedure for related examples. MS (DCI): m/z 403 (M+H)$^+$.

Example 210

1-cyclobutyl-3-{3-[(cyclobutylamino)methyl]benzyl}-3,4,6,7,8,9-hexahydro-5H-pyrazolo[3,4-c]isoquinolin-5-one The title compound was prepared as TFA salt according to the procedure for related examples. MS (DCI): m/z 417 (M+H)$^+$.

Example 211

1-cyclobutyl-3-{[1-(cyclopropylmethyl)piperidin-3-yl]methyl}-3,4,6,7,8,9-hexahydro-5H-pyrazolo[3,4-c]isoquinolin-5-one The title compound was prepared as TFA salt according to the procedure for related examples. MS (DCI): m/z 395 (M+H)$^+$.

Example 212

1-cyclobutyl-3-[(1-isopropylpiperidin-3-yl)methyl]-3,4,6,7,8,9-hexahydro-5H-pyrazolo[3,4-c]isoquinolin-5-one The title compound was prepared as TFA salt according to the procedure for related examples. MS (DCI): m/z 383 (M+H)$^+$.

Example 213

1-cyclobutyl-3-[(1-isobutylpiperidin-3-yl)methyl]-3,4,6,7,8,9-hexahydro-5H-pyrazolo[3,4-c]isoquinolin-5-one The title compound was prepared as TFA salt according to the procedure for related examples. MS (DCI): m/z 397 (M+H)$^+$.

Example 214

1-cyclobutyl-3-[(1-cyclobutylpiperidin-3-yl)methyl]-3,4,6,7,8,9-hexahydro-5H-pyrazolo[3,4-c]isoquinolin-5-one The title compound was prepared as TFA salt according to the procedure for related examples. MS (DCI): m/z 395 (M+H)$^+$.

Example 215

1-cyclobutyl-3-[(1-cyclopentylpiperidin-3-yl)methyl]-3,4,6,7,8,9-hexahydro-5H-pyrazolo[3,4-c]isoquinolin-5-one The title compound was prepared as TFA salt according to the procedure for related examples. MS (DCI): m/z 409 (M+H)$^+$.

Example 216

1-cyclobutyl-3-[(1-cyclohexylpiperidin-3-yl)methyl]-3,4,6,7,8,9-hexahydro-5H-pyrazolo[3,4-c]isoquinolin-5-one The title compound was prepared as TFA salt according to the procedure for related examples. MS (DCI): m/z 423 (M+H)+.

Example 217

1-cyclobutyl-3-[(1-cycloheptylpiperidin-3-yl)methyl]-3,4,6,7,8,9-hexahydro-5H-pyrazolo[3,4-c]isoquinolin-5-one The title compound was prepared as TFA salt according to the procedure for related examples. MS (DCI): m/z 437 (M+H)+.

Example 218

1-cyclobutyl-3-[(1-tetrahydro-2H-pyran-4-ylpiperidin-3-yl)methyl]-3,4,6,7,8,9-hexahydro-5H-pyrazolo[3,4-c]isoquinolin-5-one The title compound was prepared as TFA salt according to the procedure for related examples. MS (DCI): m/z 425 (M+H)+.

Example 219

1-cyclobutyl-3-{[1-(pyridin-2-ylmethyl)piperidin-3-yl]methyl}-3,4,6,7,8,9-hexahydro-5H-pyrazolo[3,4-c]isoquinolin-5-one The title compound was prepared as TFA salt according to the procedure for related examples. MS (DCI): m/z 432 (M+H)+.

Example 220

1-cyclobutyl-3-{[1-(pyridin-3-ylmethyl)piperidin-3-yl]methyl}-3,4,6,7,8,9-hexahydro-5H-pyrazolo[3,4-c]isoquinolin-5-one The title compound was prepared as TFA salt according to the procedure for related examples. MS (DCI): m/z 432 (M+H)+.

Example 221

1-cyclobutyl-3-{[1-(pyridin-4-ylmethyl)piperidin-3-yl]methyl}-3,4,6,7,8,9-hexahydro-5H-pyrazolo[3,4-c]isoquinolin-5-one The title compound was prepared as TFA salt according to the procedure for related examples. MS (DCI): m/z 432 (M+H)+.

Example 222

3-isopropyl-1-pyrrolidin-2-yl-3,4,6,7,8,9-hexahydro-5H-pyrazolo[3,4-c]isoquinolin-5-one MS (DCI): m/z 301 (M+H)+.

Example 223 benzyl methyl[(3-methyl-5-oxo-4,5,6,7,8,9-hexahydro-3H-pyrazolo[3,4-c]isoquinolin-1-yl)methyl]carbamate The title compound was prepared according to procedure for related example. MS (DCI): m/z 381 (M+H)+.

Example 224

3-methyl-1-[(2S)-piperidin-2-yl]-3,4,6,7,8,9-hexahydro-5H-pyrazolo[3,4-c]isoquinolin-5-one The title compound was prepared as TFA salt according to procedure for related example. MS (DCI): m/z 287 (M+H)+.

Example 225

1-{[cyclobutyl(methyl)amino]methyl}-3-methyl-3,4,6,7,8,9-hexahydro-5H-pyrazolo[3,4-c]isoquinolin-5-one The title compound was prepared as HCl salt according to procedure for related example. MS (DCI): m/z 301 (M+H)+.

Example 226

1-{[cyclopentyl(methyl)amino]methyl}-3-methyl-3,4,6,7,8,9-hexahydro-5H-pyrazolo[3,4-c]isoquinolin-5-one The title compound was prepared as HCl salt according to procedure for related example. MS (DCI): m/z 315 (M+H)+.

Example 227

1-[(2S)-1-(cyclopropylmethyl)piperidin-2-yl]-3-methyl-3,4,6,7,8,9-hexahydro-5H-pyrazolo[3,4-c]isoquinolin-5-one The title compound was prepared as HCl salt according to procedure for related example. MS (DCI): m/z 341 (M+H)+.

Example 228

1-[(2S)-1-cyclobutylpiperidin-2-yl]-3-methyl-3,4,6,7,8,9-hexahydro-5H-pyrazolo[3,4-c]isoquinolin-5-one The title compound was prepared as HCl salt according to procedure for related example. MS (DCI): m/z 341 (M+H)+.

Example 229

1-[(2S)-1-isobutylpiperidin-2-yl]-3-methyl-3,4,6,7,8,9-hexahydro-5H-pyrazolo[3,4-c]isoquinolin-5-one The title compound was prepared as HCl salt according to procedure for related example. MS (DCI): m/z 343 (M+H)+.

Example 230

1-[(2S)-1-cyclopentylpiperidin-2-yl]-3-methyl-3,4,6,7,8,9-hexahydro-5H-pyrazolo[3,4-c]isoquinolin-5-one The title compound was prepared as HCl salt according to procedure for related example. MS (DCI): m/z 355 (M+H)+.

Example 231 benzyl (2R)-2-(3-methyl-5-oxo-4,5,6,7,8,9-hexahydro-3H-pyrazolo[3,4-c]isoquinolin-1-yl)pyrrolidine-1-carboxylate The title compound was prepared according to procedure for related example. MS (DCI): m/z 407 (M+H)+.

Example 232

3-methyl-1-[(2R)-1-tetrahydro-2H-pyran-4-ylpyrrolidin-2-yl]-3,4,6,7,8,9-hexahydro-5H-pyrazolo[3,4-c]isoquinolin-5-one The title compound was prepared as HCl salt according to procedure for related example. MS (DCI): m/z 357 (M+H)+.

Example 233 benzyl 3-(3-methyl-5-oxo-4,5,6,7,8,9-hexahydro-3H-pyrazolo[3,4-c]isoquinolin-1-yl)piperidine-1-carboxylate The title compound was prepared according to procedure for related example. MS (DCI): m/z 421 (M+H)+.

Example 234 benzyl 1-cyclopropyl-3-methyl-5-oxo-3,4,5,6,8,9-hexahydro-7H-pyrazolo[3,4-c]-2,7-naphthyridine-7-carboxylate The title compound was prepared according to procedure for related example. MS (DCI): m/z 379 (M+H)+.

Example 235 benzyl 4-(3-methyl-5-oxo-4,5,6,7,8,9-hexahydro-3H-pyrazolo[3,4-c]isoquinolin-1-yl)piperidine-1-carboxylate The title compound was prepared according to procedure for related example. MS (DCI): m/z 421 (M+H)+.

Example 236

1-(1-isopropylpiperidin-3-yl)-3-methyl-3,4,6,7,8,9-hexahydro-5H-pyrazolo[3,4-c]isoquinolin-5-one The title compound was prepared as HCl salt according to procedure for related example. MS (DCI): m/z 329 (M+H)+.

Example 237

1-[1-(cyclopropylmethyl)piperidin-3-yl]-3-methyl-3,4,6,7,8,9-hexahydro-5H-pyrazolo[3,4-c]isoquinolin-5-one The title compound was prepared as HCl salt according to procedure for related example. MS (DCI): m/z 341 (M+H)+.

Example 238

1-(1-cyclobutylpiperidin-3-yl)-3-methyl-3,4,6,7,8,9-hexahydro-5H-pyrazolo[3,4-c]isoquinolin-5-one The title compound was prepared as HCl salt according to procedure for related example. MS (DCI): m/z 341 (M+H)+.

Example 239

1-(1-cyclopentylpiperidin-3-yl)-3-methyl-3,4,6,7,8,9-hexahydro-5H-pyrazolo[3,4-c]isoquinolin-5-one The title compound was prepared as HCl salt according to procedure for related example. MS (DCI): m/z 355 (M+H)+.

Example 240

3-methyl-1-[1-(2-phenylethyl)piperidin-3-yl]-3,4,6,7,8,9-hexahydro-5H-pyrazolo[3,4-c]isoquinolin-5-one The title compound was prepared as HCl salt according to procedure for related example. MS (DCI): m/z 391 (M+H)+.

Example 241

3-methyl-1-(1-tetrahydro-2H-pyran-4-ylpiperidin-3-yl)-3,4,6,7,8,9-hexahydro-5H-pyrazolo[3,4-c]isoquinolin-5-one The title compound was prepared as HCl salt according to procedure for related example. MS (DCI): m/z 371 (M+H)+.

Example 242

1-[1-(cyclopentylmethyl)piperidin-3-yl]-3-methyl-3,4,6,7,8,9-hexahydro-5H-pyrazolo[3,4-c]isoquinolin-5-one The title compound was prepared as HCl salt according to procedure for related example. MS (DCI): m/z 369 (M+H)+.

Example 243

3-methyl-1-(1-propylpiperidin-4-yl)-3,4,6,7,8,9-hexahydro-5H-pyrazolo[3,4-c]isoquinolin-5-one The title compound was prepared as HCl salt according to procedure for related example. MS (DCI): m/z 329 (M+H)+.

Example 244

1-(1-isopropylpiperidin-4-yl)-3-methyl-3,4,6,7,8,9-hexahydro-5H-pyrazolo[3,4-c]isoquinolin-5-one The title compound was prepared as HCl salt according to procedure for related example. MS (DCI): m/z 329 (M+H)$^+$.

Example 245

1-[1-(cyclopropylmethyl)piperidin-4-yl]-3-methyl-3,4,6,7,8,9-hexahydro-5H-pyrazolo[3,4-c]isoquinolin-5-one The title compound was prepared as HCl salt according to procedure for related example. MS (DCI): m/z 341 (M+H)$^+$.

Example 246

1-(1-cyclobutylpiperidin-4-yl)-3-methyl-3,4,6,7,8,9-hexahydro-5H-pyrazolo[3,4-c]isoquinolin-5-one The title compound was prepared as HCl salt according to procedure for related example. MS (DCI): m/z 341 (M+H)$^+$.

Example 247

1-cyclopropyl-3,6-dimethyl-4,6,7,8-tetrahydrocyclopenta[d]pyrazolo[3,4-b]pyridin-5(3H)-one compound with 1-cyclopropyl-3,7-dimethyl-4,6,7,8-tetrahydrocyclopenta[d]pyrazolo[3,4-b]pyridin-5(3H)-one (1:1)

The title compound was prepared according to procedure for related example. MS (DCI): m/z 244 (M+H)$^+$.

Example 248

1-[(2S)-1-isopropylpiperidin-2-yl]-3-methyl-3,4,6,7,8,9-hexahydro-5H-pyrazolo[3,4-c]isoquinolin-5-one

Example 249

1-(1-cyclobutylpyrrolidin-3-yl)-3,4-dimethyl-3,4,6,7,8,9-hexahydro-5H-pyrazolo[3,4-c]isoquinolin-5-one MS (DCI): m/z 341 (M+H)$^+$.

What is claimed:
1. A compound which is 7,9-dimethyl-1,2,3,4,6,7-hexahydro-5H-pyrazolo[3,4-h]-1,6-naphthyridin-5-one.

* * * * *